United States Patent
Bi et al.

(10) Patent No.: US 11,261,153 B2
(45) Date of Patent: *Mar. 1, 2022

(54) ORGANIC AMINE SALT COMPOUNDS HAVING CO$_2$-DONATING ANIONS AND THEIR USE AS FOAMING AGENT

(71) Applicant: SHANDONG UNIVERSITY OF TECHNOLOGY, Shandong (CN)

(72) Inventors: Gehua Bi, Shandong (CN); Yusui Bi, Shandong (CN)

(73) Assignee: Shandong University of Technology, Shandong (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/063,889

(22) PCT Filed: May 11, 2017

(86) PCT No.: PCT/CN2017/083949
§ 371 (c)(1),
(2) Date: Nov. 8, 2018

(87) PCT Pub. No.: WO2017/206693
PCT Pub. Date: Dec. 7, 2017

(65) Prior Publication Data
US 2019/0016673 A1    Jan. 17, 2019

(30) Foreign Application Priority Data
Jun. 2, 2016 (CN) .......................... 201610392162.3

(51) Int. Cl.
| C07C 213/04 | (2006.01) |
| C08J 9/08 | (2006.01) |
| C07C 271/02 | (2006.01) |
| C08G 18/16 | (2006.01) |
| C08G 18/48 | (2006.01) |
| C08G 18/20 | (2006.01) |
| C07C 211/14 | (2006.01) |
| C08G 18/24 | (2006.01) |
| C07C 269/06 | (2006.01) |

(Continued)

(52) U.S. Cl.
CPC .......... *C07C 271/02* (2013.01); *C07C 211/14* (2013.01); *C07C 213/04* (2013.01); *C07C 269/06* (2013.01); *C08G 18/165* (2013.01); *C08G 18/2036* (2013.01); *C08G 18/242* (2013.01); *C08G 18/246* (2013.01); *C08G 18/4018* (2013.01); *C08G 18/42* (2013.01); *C08G 18/48* (2013.01); *C08G 18/4804* (2013.01); *C08G 18/4829* (2013.01); *C08G 18/7671* (2013.01); *C08J 9/08* (2013.01); *C08J 2203/02* (2013.01); *C08J 2203/14* (2013.01); *C08J 2203/142* (2013.01); *C08J 2203/204* (2013.01); *C08J 2325/06* (2013.01); *C08J 2327/06* (2013.01); *C08J 2375/04* (2013.01)

(58) Field of Classification Search
CPC ................ C08J 9/08; C07C 215/00–90; C07C 217/00–94; C07C 213/04; C07C 215/05–10; C08G 18/3271–3296
See application file for complete search history.

(56) References Cited

U.S. PATENT DOCUMENTS

| 2,186,392 A | * | 1/1940 | Reynhart | ............... C07C 215/08 |
| | | | | 564/477 |
| 4,500,656 A | * | 2/1985 | Rasshofer | .......... C08G 18/3296 |
| | | | | 521/164 |

(Continued)

FOREIGN PATENT DOCUMENTS

| CN | 101939350 A | 1/2011 |
| CN | 102471514 A | 5/2012 |

(Continued)

OTHER PUBLICATIONS

Machine Translation of JP2003342340A. Dec. 2, 2003. (Year: 2003).*
Machine Translation of PL185458B1. May 30, 2003. (Year: 2003).*
Nakamura, H. et al. Use of volatile buffers in high performance hydrophobic interaction chromatography of proteins. Analytical Sciences, 1990, 6, 137-138. (Year: 1990).*
Definition of valence. IUPAC Compendium of Chemical Terminology. 2014. (Year: 2014).*
Buffers. Jove. https://www.jove.com/science-education/11153/buffers. As viewed on Jun. 1, 2021 (Year: 2021).*

(Continued)

*Primary Examiner* — Stephen E Rieth

(57) ABSTRACT

An organic amine salt compounds of general formula $A^{n-}[B^{m+}]_p$ (I) is disclosed, wherein $A^{n-}$ is a CO$_2$-donating anion with a valence of −n, wherein n=1, 2 or 3; each $B^{m+}$ comprises: ammonium ion, hydrazinium ion and/or organic amine B cation; wherein $$m = 1\text{-}10;\ 0 < p \le \frac{n}{m};$$

and wherein $A^{n-}$ is one or more selected from a group consisting of following anions: (a) carbamate orcarbazate; (b) carbonate; (c) formate; (d) bicarbonate; (e) organic monocarbonate; (f) organic poly-carbamate; (g) orthoformate; or (h) organic poly-carbonate. The compound of general formula (I) has at least one of hydroxyalkyl group linked to N atom, i.e., has alkanolamine residue. They can be used as polyurethane foaming agent, and most of them can be used as polystyrene foaming agent or polyvinyl choride foaming agent.

9 Claims, 6 Drawing Sheets

(51) Int. Cl.
  *C08G 18/40* (2006.01)
  *C08G 18/42* (2006.01)
  *C08G 18/76* (2006.01)

(56) References Cited

U.S. PATENT DOCUMENTS

| | | | |
|---|---|---|---|
| 4,645,630 A | | 2/1987 | Rasshofer et al. |
| 5,872,156 A | * | 2/1999 | Inazawa .................. C08J 9/122 |
| | | | 521/128 |
| 2009/0203810 A1 | | 8/2009 | Haas et al. |
| 2012/0041088 A1 | * | 2/2012 | Ishida ................ C08G 18/3265 |
| | | | 521/129 |
| 2012/0202902 A1 | | 8/2012 | Wissemborski et al. |
| 2019/0016673 A1 | | 1/2019 | Bi et al. |

FOREIGN PATENT DOCUMENTS

| | | | |
|---|---|---|---|
| CN | 104559044 A | | 4/2015 |
| CN | 104945599 A | | 9/2015 |
| JP | 2003342340 A | * | 12/2003 |
| PL | 185458 B1 | * | 5/2003 |
| WO | WO-9837116 A1 | * | 8/1998 ......... C08G 18/4879 |

OTHER PUBLICATIONS

International Search Report (PCT/ISA/210) dated Aug. 15, 2017, by the State Intellectual Property Office of the P.R. China Patent Office as the International Searching Authority for International Application No. PCT/CN2017/083949.

Written Opinion (PCT/ISA/237) dated Aug. 15, 2017, by the State Intellectual Property Office of the P.R. China Patent Office as the International Searching Authority for International Application No. PCT/CN2017/083949.

International Search Report (PCT/ISA/210) dated Aug. 15, 2017, by the State Intellectual Property Office of the P.R. China Patent Office as the International Searching Authority for International Application No. PCT/CN2017/083948.

Written Opinion (PCT/ISA/237) dated Aug. 15, 2017, by the State Intellectual Property Office of the P.R. China Patent Office as the International Searching Authority for International Application No. PCT/CN2017/083948.

Ren et al., "One-Pack Epoxy Foaming with CO2 as Latent Blowing Agent," ACS Macro Lett. (2015), vol. 4, pp. 693-697.

Volatile Buffer Systems flyer (2021), 3 pages.

N,N,N',N'-Tetrakis(2-hydroxypropyl)ethylenediamine flyer (2021), 4 pages.

* cited by examiner

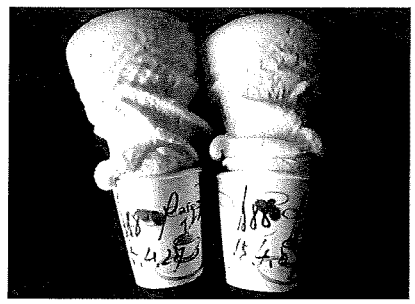
Fig. 10  Fig. 11
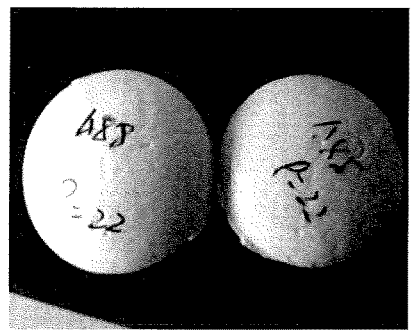
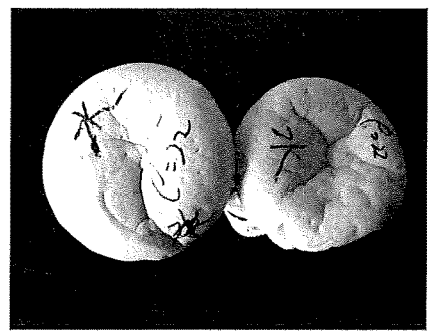
Fig. 12  Fig. 13
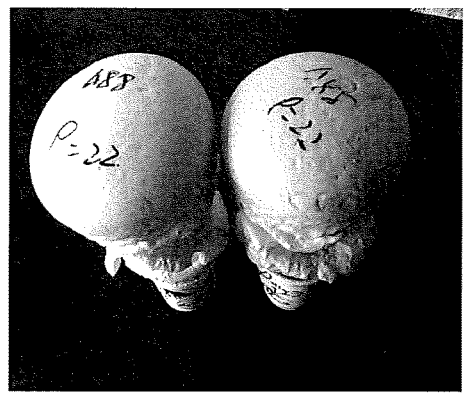
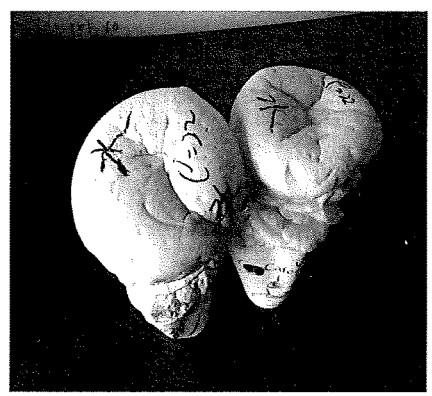
Fig. 14  Fig. 15
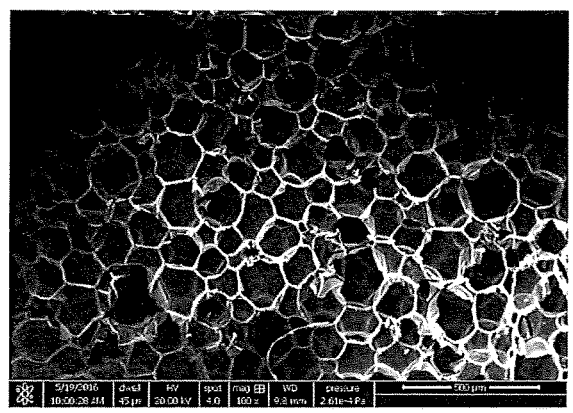
Fig. 16

ORGANIC AMINE SALT COMPOUNDS HAVING $CO_2$-DONATING ANIONS AND THEIR USE AS FOAMING AGENT

FIELD OF THE INVENTION

The present invention relates to organic amine salt compounds having $CO_2$-donating anions and their use as foaming agent, more specifically, to provide new organic amine salt compounds which not only have $CO_2$-donating anions but also have hydroxyalkyl or hydroxyalkyl alkoxy groups as solubilizing groups or have $C_2$-$C_{14}$ hydrocarbyl groups (such as 2-chloroethyl, 3-chloropropyl or phenethyl) as solubilizing groups, and their use in foamed materials such as polyurethane foams or PVC foamed materials or polystyrene expanded materials.

BACKGROUND OF THE INVENTION

The polyurethane rigid foams as new polymer materials are high-quality insulation materials due to their lighter weight, higher strength and very low thermal conductivity, such that they are widely used in industry fields such as heat-insulation for refrigerated storage, especially heat-insulation for refrigerated storage of chemical weapons, construction energy-saving, solar energy, automobiles, refrigerators and refrigerating cabinets and so on. The most important raw material in the production of polyurethane rigid foams is foaming agent. At present, these foaming agents besides cyclopentane are chlorofluorocarbons, and due to their destroying to the atmospheric ozone layer, many governments in the world have signed an international convention of "Montreal Protocol", to restrict, phase-out and even prohibit its production and use, and China is also a signatory country of the Protocol.

At present, HCFC-141b (monofluorodichloroethane) and cyclopentane are still used as second generation of chlorofluorocarbon foaming agents in China, but the use of HCFC-141b are already prohibited in developed countries of Europe and North America. In t 2013, the Chinese government will decide to freeze the consumption amount of HCFC-141b on the consumption level in 2009 and 2010, to reduce 20% of consumption amount in 2015, and to make a promise to completly prohibit its production and use in 2025. At present, pentafluoropropane (HFC-245fa) and pentafluorobutane (HFC-365) as third generation of foaming agents are used in the developed countries in Europe and North America, and these countries will prohibit the use of third generation of foaming agents before 2019, due to high GWP (greenhouse warming potential value) of the second or third generation of foaming agents. Therefor, Honeywell Company has developed a fourth generation of physical foaming agent, i.e. monochlorotrifluoropropylene (LBA), the price of this product is expensive and its GWP is more than 1, although it has ODP (ozone destructive potential value) of zero and is more environmentally friendly than third generation of foaming agents. In brief, these physical foaming agents, except cyclopentane, still can not meet environmental requirements, as they contain chlorine and fluorine elements and should be eliminated.

It was disclosed in the prior art to directly use $CO_2$ as polyurethane foaming agent, but, in view of the escapement of $CO_2$ gas and the poor solubility of it in the raw materials such as MDI and also polyester polyol and/or polyether polyol, $CO_2$ gas can not be uniformly dispersed in the foaming composition, and the foaming process is not easy to control.

Additionally, it was disclosed in the prior art to directly use small amount of water as polyurethane foaming agent, but, in view of the hydrogen bonding of water molecule and the poor solubility of water in polyester polyol and/or polyether polyol, water molecules exist in the foaming composition (such as polyether polyol component) in a form of droplets, and these droplets will cause local excess reaction and foaming in the foamed material. If water is used as foaming agent, the resultant polyurethane foam material contain many urea bonds, which significantly deteriorate strength and heat-insulating property of foam materials. In addition, if the amount of water used as the foaming agent is slightly increased, the properties and dimensional stability of the polyurethane foam are significantly affected. If water is the only foaming agent, polyurethane foams suffer from shrinkage, scorching, and poor thermal insulation.

In sum, the foaming agents such as water of prior art can not be dispersed in foaming composition in a molecular level, which will cause nonuniform distribution of cells and size uniformity of cells and influence strength properties and thermal insulating properties of the resulting foam material.

SUMMARY OF THE INVENTION

In order to overcome the technical problems in the prior art, the invention aims to provide polyurethane foaming agents not containing chlorofluorocarbons and not destroying atmospheric ozone layer and the preparation thereof.

The object of the present invention is to provide new organic amine salt compounds which not only have $CO_2$-donating anions but also have hydroxyalkyl or hydroxyalkyl alkoxy groups as solubilizing groups or have $C_2$-$C_{14}$ hydrocarbyl groups (such as 2-chloroethyl, 3-chloropropyl or phenethyl) as solubilizing groups, and their use in foamed materials such as polyurethane foams or PVC foamed materials or polystyrene expanded materials.

These new organic amine salt compounds are suitable to be used as foaming agent. They generate $CO_2$ gas during foaming process. The inventors of the present application surprisingly discovered that some types of anions used as $CO_2$ donators and having a valence of –n are easily decomposed under elevated temperature to generate $CO_2$ gas, and even when foaming is performed at a relatively low temperature, the below-described anions having a valence of –n as a $CO_2$ donor can be activated by the NCO groups contained in the isocyanate monomers such as MDI and TDI to rapidly release $CO_2$ gas. Additionally, due to solubilizing groups of the foaming agents of present invention, the foaming agents can sufficiently dissolve in foaming raw materials (such as polyether polyol or polyester polyol) or have good miscibility with the foaming raw materials, and hence during foaming, the foaming agents of present invention can uniformly dispersed in a foaming composition so as to foam uniformly, thus the distribution of cells in polyurethane foam is uniform and sizes of cells are also uniform. In addition, the foaming agent compounds of present invention contain hydroxy and/or amino groups, the decomposition products produced after decomposed to release $CO_2$ gas still contain hydroxy and/or amino groups; and if the molecular weight of the decomposition product(s) is low, the product(s) is suitable to be used as a chain-extending agent or cross-linking agent so as to react with isocyanate to form polyurethane polymer, whereas, if the molecular weight of the decomposition product(s) is higher (for example, number-average molecular weight of 100-3000), the product(s) can substitute a part of polyester polyol or polyether polyol in the foaming composition, for example, on the base of the foaming compositions of prior art, to decrease properly the amount of polyester polyol or polyether polyol. Those skilled in the art can calculate the amount of the foaming agent as well as the amount of polyester polyol and/or polyether polyol according to average hydroxyl value of the foaming agent and average hydroxyl value of polyester polyol or polyether polyol. In particular, in the process of foaming using polyols and polyisocyanates, if the organic amine salt compound of present invention is used as foaming agent, the organic amine salt compounds function as "foaming points" and also function as "chain-extending points" and/or "cross-linking points", which significantly enhance the mechanical strength of cells, and the resulting polyurethane foam has good dimensional stability. Therefore, the present invention has been completed based on the above three aspects.

In the present application, "$CO_2$-donating anion" is referred to an anion which can decompose and release $CO_2$ under heating or during foaming.

According to the first embodiment of the present invention, provided are organic amine salt compounds (i.e., organic alkanolamine salt compounds) having the following general formula (I) or a organic amine salt compound mixture comprising such compounds (i.e., an organic alkanolamine salt compound mixture):

$$A^{n-}[B^{m+}]_p \quad (I)$$

in the above formula, $A^{n-}$ is a $CO_2$-donating anion with a valence of $-n$, wherein $n=1$, 2 or 3; each $B^{m+}$ independently is or comprises ammonium ion of +1 valence ($^+NH_4$), hydrazinium ion of +1 valence ($H_3{}^+N$—$NH_2$), hydrazinium ion of +2 valence ($H_3{}^+N$—$NH_3{}^+$), and/or, one or more of organic amine B cations having m of —$^+NR^3R^4H$ groups and/or —$NR^3H$— groups;

wherein $m=1$-10, preferably $m=1$-5, more preferably $$m = 1\text{-}2;\ 0 < p \le \frac{n}{m};$$

and wherein $A^{n-}$ is one or more anions selected from following anions:
(a) carbamate or carazate (or hydrozino formate): $R^1R^2N$—$COO^-$ or $R^1R^2N$—$NH$—$COO^-$;
(b) carbonate: $CO_3{}^{2-}$;
(c) formate: $HCOO^-$;
(d) bicarbonate: $HO$—$COO^-$;
(e) organic mono carbonate: $R^aO$—$COO^-$, wherein $R^a$ is $C_1$-$C_{26}$ hydrocarbyl (preferably $C_1$-$C_{10}$ hydrocarbyl, more preferably $C_1$-$C_3$ hydrocarbyl) optionally substituted by hydroxyl or amino or halogen, or $C_1$-$C_{26}$ acyl (preferably $C_1$-$C_{10}$ acyl, more preferably $C_1$-$C_2$ acyl);
(f) organic poly-carbamates: $^-OOC$—$N(R^1)$—$R^b$—$N(R^2)$—$COO^-$, or $R^{b\prime}(—N(R^1)—COO^-)_3$,
wherein, $R^b$ is $C_1$-$C_{16}$ hydrocarbylene (preferably $C_2$-$C_{10}$ hydrocarbylene, more preferably $C_2$-$C_6$ hydrocarbylene) optionally substituted by hydroxyl or amino or halogen, and $R^{b\prime}$ is trivalent $C_2$-$C_{20}$ hydrocarbylene (preferably trivalent $C_3$-$C_{15}$ hydrocarbylene) optionally substituted by hydroxyl or amino or halogen;
(g)

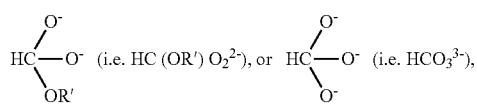

(i.e. $HC(OR')O_2{}^{2-}$), or (i.e. $HCO_3{}^{3-}$), wherein R' is H, $C_1$-$C_{26}$ hydrocarbyl (preferably $C_1$-$C_{10}$ hydrocarbyl, more preferably $C_1$-$C_3$ hydrocarbyl) optionally substituted by hydroxyl or amino or halogen, or $C_1$-$C_{26}$ acyl (preferably $C_1$-$C_{10}$ acyl, more preferably $C_1$-$C_7$ acyl); or
(h) organic poly-carbonates: $^-OOC$—$OR^cO$—$COO^-$,
wherein, $R^c$ is $C_1$-$C_{26}$ hydrocarbylene (preferably $C_2$-$C_{10}$ hydrocarbylene, more preferably $C_2$-$C_6$ hydrocarbylene) optionally substituted by hydroxyl or amino or halogen;

wherein, $R^1$, $R^2$, $R^3$ or $R^4$ is each independently chosen from: H, R, $C_1$-$C_7$ aliphatic hydrocarbyl group (preferably $C_1$-$C_4$ alkyl, more preferably $C_2$-$C_3$ alkyl) optionally substituted by hydroxyl or amino or halogen (for example hydroxyethyl or hydroxyisopropyl), $C_3$-$C_7$ cycloaliphatic hydrocarbyl group (for example, cyclobutyl or cyclohexyl) optionally substituted by hydroxyl or amino or halogen, or, $C_6$-$C_{10}$ aromatic hydrocarbyl group (preferably phenyl or methoxyphenyl) optionally substituted by hydroxyl or amino or halogen;

provided that: the compound of above general formula (I) has at least one (e.g. 1 or 2) R group linked to N atom (that is, at least one N—R group), or at least one (e.g. 1 or 2) of $R^1$, $R^2$, $R^3$ or $R^4$ group in the compound of above general formula (I) is R group linked to N atom (that is, N—R group);

wherein the R group is one or more groups selected from following groups:
(1a) $H[OCH(R_{1a})CH(R_{2a})]_q$—, for example $H(OCH_2CH_2)_q$—, $H(OCH_2CH(CH_3))_q$—, $H(OCH(CH_3)CH_2)_q$—, $H(OCH_2CH(C_6H_5))_q$—, $H(OCH(C_6H_5)CH_2)_q$—, $H(OCH_2CH(CH_2Cl))_q$—, $H(OCH(CH_2Cl)CH_2)_q$— or $H(OCH_2CH(CBr_3))_q$—;
(2a) $H[OCH(R_{1a})CH(R_{2a})CH(R_{3a})]_q$—; or
(3a) $H[OCH(R_{1a})CH(R_{2a})CH(R_{3a})CH(R_{4a})]_q$—;

wherein the value or average value of q is $q=1$-50; $R_{1a}$, $R_{2a}$, $R_{3a}$ or $R_{4a}$ each independently is selected from the following groups: H, $C_1$-$C_7$ aliphatic hydrocarbyl group optionally substituted by hydroxyl or amino or halogen, $C_3$-$C_7$ cycloaliphatic hydrocarbyl group optionally substituted by hydroxyl or amino or halogen, or, $C_6$-$C_{10}$ aromatic hydrocarbyl group optionally substituted by hydroxyl or amino or halogen.

According to the second embodiment of present invention, provided is organic amine salt compounds (i.e., organic alkanolamine salt compounds) having the following general formula (I) or an organic amine salt compound mixture comprising such compounds (i.e., organic alkanolamine salt compound mixture):

$$A^{n-}[B^{m+}]_p \quad (I)$$

in the above formula, $A^{n-}$ is a $CO_2$-donating anion with a valence of $-n$, wherein $n=1$, 2 or 3;

$B^{m+}$ is or comprises ammonium ion with a valence of +1 ($^+NH_4$), and/or, one or more of organic amine B cations (i.e., cations formed by one or more organic amines B) having m of —$^+NR^3R^4H$ groups and/or —$NR^3H$— groups (that is, m of primary amine, secondary amine and/or tertiary amine groups which can form cations by binding $^+H$ ions); wherein $m=1$-10, such as 1, 2, 3, 4, 5, 6, 7, 8, 9 or 10;

$$0 < p \le \frac{n}{m};$$

wherein $A^{n-}$ is one or more anions selected from following anions:
(a) carbamate: $R^1R^2N$—$COO^-$;
(b) carbonate: $CO_3{}^{2-}$;

(c) formate: HCOO⁻;
(d) bicarbonate: HO—COO⁻;
(e) organic monocarbonate: R$^a$O—COO⁻, wherein R$^a$ is C$_1$-C$_{26}$ hydrocarbyl (preferably C$_1$-C$_{10}$ hydrocarbyl, more preferably C$_1$-C$_3$ hydrocarbyl) optionally substituted by hydroxyl or amino or halogen, or C$_1$-C$_{26}$ acyl (preferably C$_1$-C$_{10}$ acyl, more preferably C$_1$-C$_2$ acyl);
(f) organic poly-carbamate: ⁻OOC—N(R$^1$)—R$^b$—N(R$^2$)—COO⁻, or R$^{b'}$(—N(R$^1$)—COO⁻)$_3$,
wherein, R$^b$ is C$_1$-C$_{16}$ hydrocarbylene (preferably C$_2$-C$_{10}$ hydrocarbylene, more preferably C$_2$-C$_6$ hydrocarbylene, such as —CH$_2$—CH$_2$—) optionally substituted by hydroxyl or amino or halogen, R$^{b'}$ is trivalent C$_2$-C$_{20}$ hydrocarbylene (preferably trivalent C$_3$-C$_{15}$ hydrocarbylene, such as —CH$_2$—CH(CH$_2$—)—CH$_2$—, etc.) optionally substituted by hydroxyl or amino or halogen;
(g)

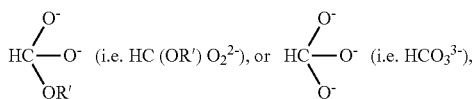

wherein R' is H, C$_1$-C$_{26}$ hydrocarbyl (preferably C$_1$-C$_{10}$ hydrocarbyl, more preferably C$_1$-C$_3$ hydrocarbyl) optionally substituted by hydroxyl or amino or halogen, or C$_1$-C$_{26}$ acyl (preferably C$_1$-C$_{10}$ acyl, more preferably C$_1$-C$_7$ acyl); or
(h) organic poly-carbonate: ⁻OOC—OR$^c$O—COO⁻,
wherein, R$^c$ is C$_1$-C$_{26}$ hydrocarbylene (preferably C$_2$-C$_{10}$ hydrocarbylene, more preferably C$_2$-C$_6$ hydrocarbylene) optionally substituted by hydroxyl or amino or halogen;
wherein, R$^1$, R$^2$, R$^3$ or R$^4$ is independently chosen from: H, R, C$_1$-C$_7$ aliphatic hydrocarbyl group (preferably C$_1$-C$_4$ alkyl, more preferably C$_2$-C$_3$ alkyl) optionally substituted by hydroxyl or amino or halogen (for example hydroxyethyl or hydroxyisopropyl), C$_3$-C$_7$ cycloaliphatic hydrocarbyl group (for example, cyclobutyl or cyclohexyl) optionally substituted by hydroxyl or amino or halogen, or, C$_6$-C$_{10}$ aromatic hydrocarbyl group (preferably phenyl or methylphenyl) optionally substituted by hydroxyl or amino or halogen;
provided that: the compound of above general formula (I) has at least one (e.g. 1 or 2) R group linked to N atom (that is, at least one N—R group), or at least one (e.g. 1 or 2) of R$^1$, R$^2$, R$^3$ or R$^4$ group in the compound of above general formula (I) is R group linked to N atom (that is, N—R group);
wherein the R group is one or more groups selected from following groups:
 (1a) H[OCH(R$_{1a}$)CH(R$_{2a}$)]$_q$—, for example H(OCH$_2$CH$_2$)$_q$—, H(OCH$_2$CH(CH$_3$))$_q$—, H(OCH(CH$_3$)CH$_2$)$_q$—, H(OCH$_2$CH(C$_6$H$_5$))$_q$—, H(OCH(C$_6$H$_5$)CH$_2$)$_q$—, H(OCH$_2$CH(CH$_2$Cl))$_q$—, H(OCH(CH$_2$Cl)CH$_2$)$_q$— or H(OCH$_2$CH(CBr$_3$))$_q$—;
 (2a) H[OCH(R$_{1a}$)CH(R$_{2a}$)CH(R$_{3a}$)]$_q$—; or
 (3a) H[OCH(R$_{1a}$)CH(R$_{2a}$)CH(R$_{3a}$)CH(R$_{4a}$)]$_q$—;
wherein the value or mean value of q is q=1-50, preferably 1-20, more preferably 1-5, more preferably q=1-4, more preferably q=1-3, particularly preferably q=1-2.5, more particularly preferably q=1.5-2.0, calculated as average value of q, or even q is 5-50, more preferably 10-20; R$_{1a}$, R$_{2a}$, R$_{3a}$ or R$_{4a}$ is selected independently of each other from C$_1$-C$_7$ aliphatic hydrocarbon group optionally substituted by hydroxyl or amino or halogen, C$_3$-C$_7$ cycloaliphatic hydrocarbon group (such as cyclobutyl or cyclohexyl) optionally substituted by hydroxyl or amino or halogen, C$_6$-C$_{10}$ aromatic hydrocabon group (such as phenyl or methylphenyl) optionally substituted by hydroxyl or amino or halogen.

According to the third embodiment of present invention, provided is organic amine salt compounds (i.e., organic alkanolamine salt compounds) having the following general formula (I) or a organic amine salt compound mixture comprising such compounds (i.e., organic alkanolamine salt compound mixture), that is to say, to provide alkanolamine salt compounds of following general formula (I) having hydrazino group:

in the above formula, A$^{n-}$ is a CO$_2$-donating anion with a valence of –n, wherein n=1, 2 or 3;
each B$^{m+}$ is independently or comprises: ammonium ion of +1 valence (⁺NH$_4$), hydrazinium ion of +1 valence (H$_3$⁺N—NH$_2$), hydrazinium ion of +2 valence (H$_3$⁺N—NH$_3$⁺), and/or, one or more organic amine B cations having m of —⁺NR$^3$R$^4$H groups and/or —⁺NR$^3$H— groups; and also, at least one of A$^{n-}$ and B$^{m+}$ comprises hydrazine or comprises hydrazino or substituted hydrazino;
wherein m=1-10, preferably m=1-5, more preferably $$m = 1\text{-}2; 0 < p \leq \frac{n}{m};$$

and
wherein A$^{n-}$ is one or more anions selected from following anions:
(a) carbamate or carbazate (hydrozino formate): R$^1$R$^2$N—COO⁻ or R$^1$R$^2$N—NH—COO⁻;
(b) carbonate: CO$_3$$^{2-}$;
(c) formate: HCOO⁻;
(d) bicarbonate: HO—COO⁻;
(e) organic mono carbonate: R$^a$O—COO⁻, wherein R$^a$ is C$_1$-C$_{26}$ hydrocarbyl (preferably C$_1$-C$_{10}$ hydrocarbyl, more preferably C$_1$-C$_3$ hydrocarbyl) optionally substituted by hydroxyl or amino or halogen, or C$_1$-C$_{26}$ acyl (preferably C$_1$-C$_{10}$ acyl, more preferably C$_1$-C$_2$ acyl);
(f) organic poly-carbamate: ⁻OOC—N(R$^1$)—R$^b$—N(R$^2$)—COO⁻, or R$^{b'}$(—N(R$^1$)—COO⁻)$_3$,
herein, R$^b$ is C$_1$-C$_{16}$ hydrocarbylene (preferably C$_2$-C$_{10}$ hydrocarbylene, more preferably C$_2$-C$_6$ hydrocarbylene) optionally substituted by hydroxyl or amino or halogen, and R$^{b'}$ is trivalent C$_2$-C$_{20}$ hydrocarbylene (preferably trivalent C$_3$-C$_{15}$ hydrocarbylene) optionally substituted by hydroxyl or amino or halogen;
(g)

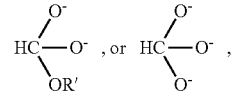

wherein R' is H, C$_1$-C$_{26}$ hydrocarbyl (preferably C$_1$-C$_{10}$ hydrocarbyl, more preferably C$_1$-C$_3$ hydrocarbyl) optionally substituted by hydroxyl or amino or halogen, or C$_1$-C$_{26}$ acyl (preferably C$_1$-C$_{10}$ acyl, more preferably C$_1$-C$_7$ acyl); or
(h) organic poly-carbonate: ⁻OOC—OR$^c$O—COO⁻,
wherein, R$^c$ is C$_1$-C$_{26}$ hydrocarbylene (preferably C$_2$-C$_{10}$ hydrocarbylene, more preferably C$_2$-C$_6$ hydrocarbylene) optionally substituted by hydroxyl or amino or halogen;
wherein, R$^1$, R$^2$, R$^3$ or R$^4$ is independently chosen from: H, R, C$_1$-C$_7$ aliphatic hydrocarbyl group (preferably C$_1$-C$_4$ alkyl, more preferably C$_2$-C$_3$ alkyl) optionally substituted by hydroxyl or amino or halogen (for example hydroxyethyl or hydroxyisopropyl), $C_3$-$C_7$ cycloaliphatic hydrocarbyl group (for example, cyclobutyl or cyclohexyl) optionally substituted by hydroxyl or amino or halogen, or, $C_6$-$C_{10}$ aromatic hydrocarbyl group (preferably phenyl or methoxyphenyl) optionally substituted by hydroxyl or amino or halogen;

provided that: the compound of above general formula (I) has at least one (e.g. 1 or 2) R group linked to N atom (that is, at least one N—R group), or at least one (e.g. 1 or 2) of $R^1$, $R^2$, $R^3$ or $R^4$ group in the compound of above general formula (I) is R group linked to N atom (that is, N—R group);

wherein the R group is one or more selected from a group consisting of following groups:

(1a)   $H[OCH(R_{1a})CH(R_{2a})]_q$—, for example $H(OCH_2CH_2)_q$—, $H(OCH_2CH(CH_3))_q$—, $H(OCH(CH_3)CH_2)_q$—, $H(OCH_2CH(C_6H_5))_q$—, $H(OCH(C_6H_5)CH_2)_q$—, $H(OCH_2CH(CH_2Cl))_q$—, $H(OCH(CH_2Cl)CH_2)_q$— or $H(OCH_2CH(CBr_3))_q$—;

(2a) $H[OCH(R_{1a})CH(R_{2a})CH(R_{3a})]_q$—; or (3a) $H[OCH(R_{1a})CH(R_{2a})CH(R_{3a})CH(R_{4a})]_q$—;

wherein the value or average value of q is q=1-50; $R_{1a}$, $R_{2a}$, $R_{3a}$ or $R_{4a}$ each independently is selected from the following groups: H, $C_1$-$C_7$ aliphatic hydrocarbyl group optionally substituted by hydroxyl or amino or halogen, $C_3$-$C_7$ cycloaliphatic hydrocarbyl group optionally substituted by hydroxyl or amino or halogen, or, $C_6$-$C_{10}$ aromatic hydrocarbyl group optionally substituted by hydroxyl or amino or halogen.

Preferably, when $A^{n-}$ is (a) carbamate or carbazate, at least one (for example 1 or 2) of $R^1$, $R^2$, $R^3$ or $R^4$ in the compound of general formula (I) is R group linked to N atom, and the compound of general formula (I) has at least one (e.g., 1 or 2) R group linked to N atom and at least one (e.g., 1 or 2) hydrazino group or substituted hydrazino group; or when $A^{n-}$ is (b), (c), (d), (e), (f), (g) or (h), the compound of general formula (I) comprises organic amine B and the organic amine B has at least one (e.g., 1 or 2) R group linked to N atom and at least one (e.g., 1 or 2) hydrazino or substituted hydrazino group.

In the present application, "at least one of $A^{n-}$ and $B^{m+}$ comprises hydrazine or comprises hydrazino or substituted hydrazino group" refers to that the compound of general formula (I) comprises at least one hydrazine ion or comprises at least one hydrazino or substituted hydrazino group; more specifically, if $A^{n-}$ is one or more anions selected from (b), (c), (d), (e), (f), (g) or (h), $B^{m+}$ is or comprises: hydrazine ion of +1 valence ($H_3^+N$—$NH_2$), hydrazine ion of +2 valence ($H_3^+N$—$NH_3^+$), or one or more organic amine B cations having hydrazino or substituted hydrazino group (for example the hydrazino or substituted hydrazino group corresponds to —$^+NR^3R^4H$ group or —$^+NR^3H$— group) (i.e., organic amine B has hydrazino or substituted hydrazino group); or if $A^{n-}$ is (a) amino-carbamate $R^1R^2N$—NH—$COO^-$, $B^{m+}$ is or comprises ammonium ion of +1 valence ($^+NH_4$), hydrazine ion of +1 valence ($H_3^+N$—$NH_2$), hydrazine ion of +2 valence ($H_3^+N$—$NH_3^+$), and one or more organic amine B cations having m of —$^+NR^3R^4H$ groups and/or —$^+NR^3H$— groups, said organic amine B has or does not has hydrazino or substituted hydrazino group.

According to the fourth embodiment of present invention, provided are organic amine salt compounds of following general formula (I):

$A^{n-}[B^{m+}]_p$   (I)

in the above formula, $A^{n-}$ is a $CO_2$-donating anion with a valence of –n, wherein n=1 or 2;

each $B^{m+}$ independently is or comprises ammonium ion of +1 valence ($^+NH_4$), hydrazinium ion of +1 valence ($H_3^+N$—$NH_2$), hydrazinium ion of +2 valence ($H_3^+N$—$NH_3^+$), and/or, one or more organic amine B cations having m of —$^+NR^3R^4H$ groups and/or —$^+NR^3H$— groups;

wherein m=1-10, preferably m=1-5, more preferably

and
wherein $A^{n-}$ is one or more anions selected from following anions:

(a) carbamate or carbazate (hydrozino formate): $R^1R^2N$—$COO^-$ 或 $R^1R^2N$—NH—$COO^-$;

(b) carbonate: $CO_3^{2-}$;

(c) formate: $HCOO^-$; or (d) bicarbonate: HO—$COO^-$;

wherein, $R^1$, $R^2$, $R^3$ or $R^4$ is each independently chosen from: H, R, $C_1$-$C_7$ aliphatic hydrocarbyl group (preferably $C_1$-$C_4$ alkyl, more preferably $C_2$-$C_3$ alkyl) optionally substituted by hydroxyl or amino or halogen (for example hydroxyethyl or hydroxyisopropyl), $C_3$-$C_7$ cycloaliphatic hydrocarbyl group (for example, cyclobutyl or cyclohexyl) optionally substituted by hydroxyl or amino or halogen, or, $C_6$-$C_{10}$ aromatic hydrocarbyl group (preferably phenyl or methylphenyl) optionally substituted by hydroxyl or amino or halogen;

provided that: when $A^{n-}$ is (a) carbamate or carbazate, at least one of $R^1$, $R^2$, $R^3$ or $R^4$ group in the compound of above general formula (I) is R group linked to N atom, or the compound of above general formula (I) has at least one R group linked to N atom; or when $A^{n-}$ is (b), (c) or (d), the compound of general formula (I) comprises organic amine B and said organic amine B has at least one R group linked to N atom;

wherein the R group is one or more groups selected from following groups:

(1a)   $H[OCH(R_{1a})CH(R_{2a})]_q$—, for example $H(OCH_2CH_2)_q$—, $H(OCH_2CH(CH_3))_q$—, $H(OCH(CH_3)CH_2)_q$—, $H(OCH_2CH(C_6H_5))_q$—, $H(OCH(C_6H_5)CH_2)_q$—, $H(OCH_2CH(CH_2Cl))_q$—, $H(OCH(CH_2Cl)CH_2)_q$— or $H(OCH_2CH(CBr_3))_q$—;

(2a) $H[OCH(R_{1a})CH(R_{2a})CH(R_{3a})]_q$—; or (3a) $H[OCH(R_1a)CH(R_{2a})CH(R_{3a})CH(R_{4a})]_q$—;

wherein the value or average value of q is q=1-50; $R_{1a}$, $R_{2a}$, $R_{3a}$ or $R_{4a}$ each independently is selected from the following groups: H, $C_1$-$C_7$ aliphatic hydrocarbyl group optionally substituted by hydroxyl or amino or halogen, $C_3$-$C_7$ cycloaliphatic hydrocarbyl group optionally substituted by hydroxyl or amino or halogen, or, $C_6$-$C_{10}$ aromatic hydrocarbyl group optionally substituted by hydroxyl or amino or halogen.

Preferably, in the present application, organic amine compound B having at least one N—R group is formed by substituting on at least one N atom of each molecule of organic amine compound (M), ammonia or hydrazine by one or more of above-mentioned R groups.

In the present application, it is preferred that, when $A^{n-}$ is (b), (c), (d), (e), (f), (g) or (h), the compound of the general formula (I) has on average 1-5.5 R groups per molecule, preferably 1.3-5 R groups, more preferably 1.5-2 R groups, and also these R groups are present in the organic amine compound B having at least one N—R group; or when $A^{n-}$ is (a) carbamate or carbazate, the compound of general formula (I) has on average 1-5.5 R groups per molecule, preferably 1.3-5 R groups, more preferably 1.5-2 R groups, and also these R groups are present in the organic amine compound B or in the anion (a).

It is preferred in the present application that, R is hydroxypropyl, i.e., HO—$CH_2$—$CH_2$($CH_3$)— or HO—$CH_2$($CH_3$)—$CH_2$—, hydroxyethyl and/or hydroxychloropropyl.

It is preferred in the present application that, in the compound of the general formula (I) or in the mixture comprising such compounds, the mole ratio of the compound of the general formula (I) having one R group (for example monoalkanolamine salt) to the compound of the general formula (I) having two R groups (for example di-alkanol amine salt) is 1:0 to 1:2.5, preferably 1:0.3 to 1:2, preferably 1:0.5 to 1:1.

In the present application, $A^{n-}$ [$B^{m+}$], can also be represent as chemical formula or general formula ABp. They are alkanolamine salt compounds. Accordingly, they are in a form of ionic compounds in presence of water.

It is preferred in the present application that A or $A^{n-}$ is one or more anions selected from following anions:
 (a) carbamate or carbazate (i.e., hydrozino formate): $R^1R^2N$—$COO^-$ or $R^1R^2N$—NH—$COO^-$;
 (b) carbonate: $CO_3^{2-}$; or
 (d) bicarbonate: HO—$COO^-$.

It is preferred in the present application that, $$0.5 \leq p \leq \frac{n}{m}.$$

Preferably, m=1 or 2 or 3.

It is preferred in the present application that substituted hydrazino group refers to hydrazino group substituted by above-mentioned substituents $R^1$, $R^2$, $R^3$ or $R^4$.

In the present application, in general, pH of a compound of the general formula (I) wherein $A^{n-}$ is formate (c) or a mixture comprising such compound is 5.5-6.5. The pH of other compounds of general formula (I), except for compounds of general formula (I) wherein $A^{n-}$ is formate (c) (its pH=5.5-6.5), is 7.5-10, preferably 7.8-9.5, more preferably 8-9. The content of alkali metals or alkaline earth metals in the compound of the general formula (I) or the mixture comprising such compound is preferably 0-200 ppm (by mass), more preferably below 100 ppm, still more preferably below 10 ppm, most preferably is below detection limit or is 0 ppm.

It is preferred in the present application that: the water content in the compound (s) of the general formula (I) or in a compound mixture comprising such compounds is 0-40 wt %, preferably 5-35 wt %, more preferably 10-30 wt %, more preferably 15-25 wt %. Correspondingly, in the present application, the compound of general formula (I) or mixture thereof contains 22-96 wt %, preferably 25-95 wt %, preferably 27-90 wt %, preferably 30-85 wt %, preferably 40-80 wt %, more preferably 45-75 wt % of salt of monoalkanolamine (for example monoethanolamine and/or monopropanolamine) or salt of dialkanolamine (for example diethanolamine and/or dipropanolamine) (i.e., the sum of both salts: salt of monoalkanolamine+salt of di-alkanolamine), based on the total weight of the compound(s) of the general formula (I) or the compound mixture. Or alternatively, the compound of the general formula (I) or the compound mixture comprising such compound contains 15-90 wt %, preferably 17-88 wt %, preferably 20-85 wt %, preferably 25-80 wt %, more preferably 30-70 wt % of monoalkanolamine (for example monoethanolamine and/or mono-isopropanolamine) or dialkanolamine (for example diethanolamine and/or di-isopropanolamine) (i.e., the sum of both alkanolamines: mono alkanolamine+di-alkanolamine), based on the total weight of the compound of the general formula (I) or the compound mixture.

Preferably, the compound of the general formula (I) contain, on average, 1.5-5 of R groups per molecule.

In the present application, hydrazine ion refers to: hydrazine ion of +1 valence ($H_3^+N$—$NH_2$) or hydrazine ion of +2 valence ($H_3^+N$—$NH_3^+$). That is to say, hydrazine ion is or comprises: hydrazine ion of +1 valence ($H_3^+N$—$NH_2$) and hydrazine ion of +2 valence ($H_3^+N$—$NH_3^+$).

In the present application, the compound of the general formula (I) has at least one above-mentioned R group per molecule.

In the present application, the R group may be the same as or different from the following groups: $C_1$-$C_7$ aliphatic hydrocarbyl group (preferably $C_1$-$C_4$ alkyl) optionally substituted by hydroxyl or amino or halogen, $C_3$-$C_7$ cycloaliphatic hydrocarbyl group (cyclobutyl or cyclohexyl) optionally substituted by hydroxyl or amino or halogen, or, $C_6$-$C_{10}$ aromatic hydrocarbyl group (preferably phenyl or methylphenyl) optionally substituted by hydroxyl or amino or halogen.

In the present application, —$^+NR^3R^4H$ group refers to —$NR^3R^{4+}H$ group, and —$^+NR^3H$— group refers to —$NR^3$($^+H$)— group. In general, organic amine B has ≥m (for example from m to m+3) of primary amine, secondary amine and/or tertiary amine groups, and optionally has quaternary ammonium group(s). For example, $CH_3CH_2^+NH_2H$ (i.e. ethylamine cation, $CH_3CH_2NH_2^+H$) is formed by bonding of ethylamine and a $^+H$ ion, wherein $B^{1+}$=$CH_3CH_2^+NH_2H$ or $CH_3CH_2NH_2^+H$, m=1, B=ethylamine. In the above general formula, primary amine, secondary amine and/or tertiary amine group is respectively selected from —$NR^3R^4$ group and —$NR^3$— group.

The organic amine compounds B are organic amines which have m to m+3 of primary amine, secondary amine and/or tertiary amine groups and optionally have quaternary ammonium group. Preferably, the organic amine compounds B are organic amine compounds having 2-200 carbon atoms (preferably 3-50, more preferably 3-20, more preferably 3-12 carbon atoms). In general, the compounds B each have the above-mentioned R group (s).

In the present application, the organic amine compounds B, or the organic amine compounds having ≥m (for example from m to m+3) of primary amine, secondary amine and/or tertiary amine groups and optionally quaternary ammonium group (s), can form $B^{m+}$ by bonding of them with m of $^+H$ ion.

Preferrably, $A^{n-}$ is a combination or mixture of two or more of anions selected from above-mentioned anions (a)-(h), and/or $B^{m+}$ is a combination or mixture of two or more of above-mentioned organic amine cations, and thus the compounds of general formula (I) are a mixture.

In present application, p of $B^{m+}$ may be the same or different, or p of B may be the same or different. It is preferred that p of $B^{m+}$ are different or p of B are different from each other.

The present invention thereby provide a foaming agent which comprises an organic amine salt compound of the general formula (I) or a mixture of organic amine salt compounds of the general formula (I), or, which consists of or consists mainly of an organic amine salt compound of the general formula (I) or a mixture of organic amine salt compounds of general formula (I).

Additionally, provided is an embodiment wherein $A^{n-}$ is one or more anions selected from the following anions: (a), (c), (d), (e), (f) or (h).

In general, in the formula (I), a single $A^{n-}$ anion having a valency of +2 or +3 can form a salt with one or more of $B^{m+}$ respectively. Whereas, a single organic amine ion $B^{m+}$ having a plurality (i.e. two or more) of $—N^+R^3R^4H$ groups and/or $—N^+R^3H—$ groups can form a salt with one or more of $A^{n-}$ anions.

With respect to (c) $HCOO^-$, ammonium formate, hydrazinium formate or formic acid organic amine salts as such are a stable compound, and their decomposition temperature is usually more than 100° C., for example, the melting point of ammonium formate is as high as 116° C. However, it is discovered that when ammonium formate, hydrazinium formate or formic acid organic amine salts is used as polyurethane foaming agent, they become unstable upon contacting with isocyanate (such as MDI), due to the following aspects: ammonium formate, hydrazinium formate or formic acid organic amine salts reacts with NCO group to form unstable anhydride group, and the latter promptly decomposes to release carbon dioxide gas and also carbon monoxide gas. Therefore, attention should be paid to ventilation and explosion protection in practical applications.

Also, for the same reason, the following anions become unstable upon contacting with isocyanate (such as MDI): (e) $R^aO—COO^-$; (f) $^-OOC—N(R^1)—R^b—N(R^2)—COO^-$ or $R^{b'}(—N(R^1)—COO^-)_3$; or (h) $^-OOC—OR^cO—COO^-$;

Preferably, (e) $R^aO—COO^-$ is anion or acid radical formed by hydrocarbyl hydrogen carbonate (for example, methyl hydrogen carbonate or ethyl hydrogencarbonate).

Preferably, (f) $^-OOC—N(R^1)—R^b—N(R^2)—COO^-$ or $R^{b'}(—N(R^1)—COO^-)_3$ is anion or acid radical formed by hydrocarbylene di (carbamic acid) or hydrocarbylene tri (carbamic acid) respectively.

Preferably, (h) $^-OOC—OR^cO—COO^-$ is anion or acid radical formed by hydrocarbylene di (carbonic acid) (for example, ammonium ethylenedi (carbonate) $NH_4OOC—OCH_2CH_2O—COONH_4$).

When the compounds of general formula (I) are used as foaming agent to prepare thermal insulation polyurethane foams, especially closed-cell type polyurethane foams, taking the foaming efficiency, the odor of foaming agent, the insulating property of foams, the dimensional stability of foam cells and the dimensional stability of polyurethane foam product into account, it is prefered that q is 1-5, more preferably q is 1-4, more preferably q is 1-3, particularly preferably q is 1-2.5, more particularly preferably q is 1.5-2.0, calculated as average value of q. Accordingly, it is more preferred that B is a mixture of two or more of above-mentioned compounds. It is more preferred that B comprises at least one N—H group (N—H covalent bond, namely, H linked to N atom).

$R^1$, $R^2$, $R^3$ or $R^4$ is each independently chosen from: H, R, $C_1$-$C_4$ aliphatic hydrocarbyl group (for example methyl or ethyl or propyl) optionally substituted by hydroxyl or amino or halogen, cyclobutyl or cyclohexyl optionally substituted by hydroxyl or amino or halogen, or, phenyl or methylphenyl optionally substituted by hydroxyl or amino or halogen.

Preferably, $R_{1a}$, $R_{2a}$, $R_{3a}$ or $R_{4a}$ each independently is selected from the following groups: H, $C_1$-$C_3$ aliphatic hydrocarbyl group optionally substituted by hydroxyl or amino or halogen, $C_3$-$C_6$ cycloaliphatic hydrocarbyl group optionally substituted by hydroxyl or amino or halogen, or, $C_6$-$C_7$ aromatic hydrocarbyl group (such as phenyl or methylphenyl) optionally substituted by hydroxyl or amino or halogen.

More preferably, $R_{1a}$, $R_{2a}$, $R_{3a}$ or $R_{4a}$ each independently is selected from the following groups: H, methyl, or ethyl optionally substituted by hydroxyl or amino or halogen, propyl or isopropyl optionally substituted by hydroxyl or amino or halogen, cyclohexyl optionally substituted by hydroxyl or amino or halogen, or, phenyl or methylphenyl optionally substituted by hydroxyl or amino or halogen.

More preferably, $R_{1a}$, $R_{2a}$, $R_{3a}$ or $R_{4a}$ each independently is selected from the following groups: H, methyl, chloromethyl, bromomethyl, ethyl, cyclohexyl, or phenyl.

In general, the organic amine salt compounds of the general formula (I) contain alkanolamine compound or alkanolamine compound residue. That is to say, the organic amine salt compound of the general formula (I) is one or more of organic amine salt compounds which have $CO_2$-donating anion $A^{n-}$ and contain alkanolamine compound or alkanolamine compound residue.

Preferably, $A^{n-}$ is one or more anions selected from a group consisting of following anions:
(a) $R^1R^2N—COO^-$ or $R^1R^2N—NH—COO^-$; wherein $R^1$ and $R^2$ each independently is hydrogen, methyl, ethyl, hydroxymethyl, hydroxyethyl or hydroxypropyl;
(b) $CO_3^{2-}$;
(c) $HCOO^-$;
(d) $HO—COO^-$; or
(g)

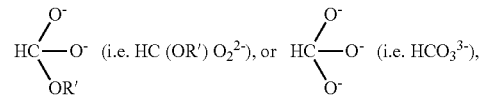

wherein R' is H, $C_1$-$C_{26}$ hydrocarbyl (preferably $C_1$-$C_{10}$ hydrocarbyl, more preferably methyl, ethyl or propyl) optionally substituted by hydroxyl or amino or halogen, or $C_1$-$C_{26}$ acyl (preferably $C_1$-$C_{10}$ acyl, more preferably formyl, acetyl or propionyl).

In the present application, "optionally" represent "carry out" or "not carry out", or represent "substituted" or "not substituted". While "optional" represents "presence" or "absence".

In general, in the compounds of the general formula (I), 50-100% of ammonia, hydrazine or amino and/or amine groups (i.e. $—N^+R^3R^4H$ groups and/or $—N^+R^3H—$ groups) in organic amine compound (B) are neutralized by anion $A^{n-}$, that is to say, the salt-forming rate of amino and/or amine groups is 50-100%. Preferably, 65-100% of ammonia, hydrazine or amino and/or amine groups in organic amine compound (B) are neutralized by anion $A^{n-}$. More preferably, 75-100% of ammonia, hydrazine or amino and/or amine groups in organic amine compound (B) are neutralized by anion $A^{n-}$. More preferably, 75-90% of ammonia, hydrazine or amino and/or amine groups in organic amine compound (B) are neutralized by anion $A^{n-}$.

The pH of other compound of the general formula (I), except for compounds of the general formula (I) wherein $A^{n-}$ is formate (c) (its pH=5.5-6.5), is in general 7.5-10, preferably 7.8-9.5, more preferably 8-9. For example, when 50-95% of ammonia, hydrazine or the amino and/or amine groups (i.e. $—N^+R^3R^4H$ group and/or $—N^+R^3H—$ group) in the organic amine compound (B) are neutralized by anion $A^{n-}$, the compound of general formula (I) is relatvely stable.

When 100% of ammonia, hydrazine or the amino and/or amine groups in the organic amine compound (B) are neutralized by anion $A^{n-}$, the general formula (I) became to the following general formula:

$$A^{n-} \cdot \frac{n}{m}(B^{m+})(I').$$

In the present application, for brevity and clarity, the organic amine ion having m (wherein m=1-10, such as 1, 2, 3, 4, 5, 6, 7, 8, 9 or 10) of —$N^+R^3R^4H$— group (s) and/or —$N^+R^3H$— group (s) may be assumed to be organic amine ion having +m valency.

Preferably, with respect to organic amine ion ($B^{m+}$) having m (for example m=1 or m=2-10, such as 3, 4 or 5) of —$N^+R^3R^4H$ groups and/or —$N^+R^3H$— groups, the compound (B) is formed from organic amine compound (M) having at least one (preferably at least two) N—H covalent bond (namely having at least one active hydrogen bound to N atom), ammonia and/or hydrazine used as starting material. Namely, the N—R group in the B or $B^{m+}$ is formed by substitution on at least one of the N atoms of each molecule of the organic amine compound (M), ammonia and/or hydrazine by one or more of above-mentioned R groups. That is to say, compound (B) is an organic amine compound having N—R group (or N—H covalent bond). Preferably, organic amine compound (B) having N—R group (s) is formed by substitution on at least one of the N atoms of the organic amine compound (M), ammonia or hydrazine by one or more of above-mentioned R groups.

Preferably at least one of $R^1$ and $R^2$ is H, more preferably $R^1$ is H and $R^2$ is H or R group (for example hydroxyethyl or hydroxypropyl or hydroxy-chloropropyl).

Preferably, organic amine compound (M), i.e., organic amine compound (M) having at least one N—H (namely N—H covalent bond or having at least one active hydrogen H bound to N atom), is selected from following organic amine compounds:

$C_1$-$C_{24}$ hydrocarbyl amines (primary amines), for example methylamine, ethylamine, propylamine, butylamine, pentylamine, hexylamine, heptylamine, octylamine, nonylamine, decylamine, laurylamine, myristylamine, hexadecylamine, octadecylamine, eicosyl amine, tetracosyl amine, unsubstituted or substituted (such as halogen substituted) aniline, unsubstituted or substituted (such as halogen substituted) benzyl amine, cyclohexyl amine, methyl cyclohexyl amine, cyclohexyl methylamine, N-methyl cyclohexyl amine or N-methyl benzyl amine, and so on;

di ($C_1$-$C_{16}$ hydrocarbyl) amines (secondary amines, monoamines having one secondary amine group), for example dimethylamine, diethylamine, methyl ethyl amine, dipropyl amine, methyl propyl amine, ethyl propyl amine, dibutyl amine, ethyl butyl amine, dipentyl amine, dihexyl amine, diheptyl amine, dioctyl amine, dinonyl amine, didecylamine, di-(dodecyl) amine, di-(myristyl) amine, di-(hexadecyl) amine, di-(octadecyl) amine, di-(eicosyl) amine or di-(tetracosyl) amine, and so on;

$C_2$-$C_{14}$ hydrocarbylene diamines optionally substituted on the $C_2$-$C_{14}$ hydrocarbylene by hydroxy group (wherein either of the two amino groups independently is primary amine group or secondary amine group), for example ethylene diamine, N-methyl ethylene diamine, N,N'-dimethyl ethylene diamine, 1,3-propylene diamine, N-methyl,N'-ethyl-1,3-propylene diamine, butanediamine (including its various isomers, such as 1,2 or 1,3- or 1,4-butanediamine), pentanediamine (including its various isomers), hexanediamine (including its various isomers), 3-hydroxymethyl hexamethylene diamine, heptanediamine (including its various isomers), 3-hydroxymethyl heptamethylene diamine, octanediamine (including its various isomers), 3,5-dihydroxyl octamethylenediamine, nonamethylene diamine (including its various isomers), decamethylene diamine (including its various isomers), 3,6-dihydroxyl decamethylene diamine, dodecane diamine, tetradecane diamine, p- or m-phenylene diamine, 3,3'-dichloro-4,4'-diphenylmethane diamine (MOCA), or piperazine, and so on;

$C_4$-$C_{16}$ polyalkylene polyamines optionally substituted on the $C_2$-$C_{14}$ alkylene by hydroxy, for example diethylene triamine, triethylene tetra-amine, tetraethylene penta-amine, pentaethylene hexa-amine, dipropylene triamine, tripropylene tetra-amine, tetrapropylene penta-amine, pentapropylene hexa-amine, dibutylene triamine, tri butylene tetra-amine, tetrabutylene penta-amine, triethylenediamine, dimethyl diethylenetriamine, tri (2-hydroxy-1,3-propylene) tetramine or tetra (2-hydroxy-1,3-propylene) penta-amine, and so on;

$C_3$-$C_{18}$ organic triamines (optionally substituted by hydroxy) having three primary amine groups or $C_5$-$C_{18}$ organic tetramines (optionally substituted by hydroxy) having four primary amine groups, for example 1,3,5-triamino cyclohexane, 1,3,5-tri (aminoethyl) cyclohexane, 1,3,5-tri (aminopropyl)-1,3,5-hexahydro triazine, 1,3,5-tri (methylaminopropyl)-1,3,5-hexahydro triazine, or, melamine, pentaerythrityl tetramine, and so on; or $C_2$-$C_{10}$ alkanolamines, for example monoethanolamine, diethanolamine, monopropanolamine, dipropanolamine, monoisopropanolamine, diisopropanolamine, monobutanolamine, or dibutanolamine, and so on. It is more preferred that (M) is selected from:

methylamine, ethylamine, propylamine, butyl amine, pentyl amine, hexyl amine, unsubstituted or substituted (such halogen substituted) aniline, unsubstituted or substituted (such as halogen substituted) benzyl amine, cyclohexyl amine, or methyl cyclohexyl amine;

dimethylamine, diethylamine, methyl ethyl amine, dipropyl amine, or methyl propyl amine;

ethylene diamine, N-methyl-ethylene diamine, N,N'-dimethyl ethylene diamine, 1,3-propylene diamine, N-methyl, N'-ethyl-1,3-propylene diamine, butanediamine (including its various isomers, such as 1,2 or 1,3- or 1,4-butanediamine), pentanediamine (including its various isomers), hexane diamine (including its various isomers), 3-hydroxymethyl-hexanediamine, p- or m-phenylene diamine, 3,3'-dichloro-4,4'-diphenylmethane diamine (MOCA), or piperazine;

diethylene triamine, triethylenetetraamine, or tetraethylenepentamine;

1,3,5-triamino cyclohexane, 1,3,5-tri (aminoethyl) cyclohexane, 1,3,5-tri (aminopropyl)-1,3,5-hexahydro triazine, 1,3,5-tri (methylaminopropyl)-1,3,5-hexahydro triazine, or, melamine, pentaerythrityl tetramine;

or monoethanolamine, monopropanol amine, monoisopropanolamine, or monobutanolamine.

In general, if $B^{m+}$ is organic amine ion having m (for example 2-10, such as 3, 4, or 5) of —$N^+R^3R^4H$ groups and/or —$N^+R^3H$— groups other than ammonium ion of +1 valency ($^+NH_4$) or hydrazine ion (i.e., $B^{m+}$ is not ammonium ion of +1 valency ($^+NH_4$) or hydrazine ion, that is to say if B is not ammonia or hydrazine), then compound B is formed by reaction of above-mentioned organic amine compound (M), ammonia and/or hydrazine as starting material or as initiator with epoxides (such as ethylene oxide, propylene oxide, epichlorohydrin, epibromohydrin, butylene oxide, epoxychlorobutane, or styrene oxide, or a mixture of two or more thereof).

More specifically, the salt formed by compound B and $A^{n-}$, or the salt formed by B and A, or briefly the compound B, is obtained by the reaction of the salt formed from above-mentioned organic amine compound (M), ammonia and/or hydrazine and of one or more anions of (a), (b), (c), (d), (e), (f) or (h), as starting material or as initiator, with epoxides (such as ethylene oxide, propylene oxide, epichlorohydrin, epibromohydrin, butylene oxide, epoxychlorobutane, or styrene oxide, or a mixture of two or more of these epoxides).

Additionally, when $A^{n-}$ is any one of (a), (b), (c), (d), (e), (f) or (h) and $B^{m+}$ is organic amine ion having m (for example 1 or 2-10, such as 3, 4, or 5) of —$N^+R^3R^4H$ groups and/or —$N^+R^3H$— groups (i.e., $B^{m+}$ is not ammonium ion of +1 valency ($^+NH_4$) or hydrazinium ion, that is to say when B is not ammonia or hydrazine), the compounds of the general formula (I) are obtained by the reaction of ammonium salt or hydrazine salt [such as ammonium carbamate, ammonium carbamate substituted by hydroxyalkyl or hydroxyalkyl alkoxy ($R^1R^2N$—$COO^{-+NH}_4$), hydrazinium carbamate, ammoniumcarbazate, hydrazinium carbazate, ammonium carbonate ($CO_3^{2-}(^+NH_4)_2$), hydrazinium carbonate, ammonium hydrazinium carbonate, ammonium bicarbonate, hydrazinium bicarbonate, hydrazinium formate or ammonium formate, or a mixture of two or more of them] or organic amine salts (such as organic amine salts of carbamic acid, hydroxyalkyl or hydroxyalkyl alkoxy substituted organic amine salts of carbamic acid, organic amine salts of carbazic acid, N-hydroxyalkyl or N-hydroxyalkyl alkoxy substituted organic amine salts of carbazic acid, organic amine salts of carbonic acid, organic amine salts of bicarbonate, or organic amine salts of formic acid, or a mixture of two or more of them) with epoxides (such as ethylene oxide, propylene oxide, epichlorohydrin, epibromohydrin, butylene oxide, or styrene oxide, or a mixture of two or more thereof) in a solvent (preferably protonic solvent or alcoholic solvent or DMF, such as water) optionally in the presence of catalyst (for example aqueous ammonia or organic amines such as ethylamine, diethylamine or triethylamine), wherein the ammonium salt or hydrazine salt or the organic amine salt is formed by one or more of anions selected from (a), (b), (c), (d), (e), (f) or (h) with ammonia or hydrazine or with one or more of above-mentioned organic amine compound (M) respectively. In general, the said solvent is one or more selected from, but not limited to, the following solvents: methanol, ethanol, ethylene glycol, polyethylene glycol of molecular weight less than 400, polypropylene glycol of molecular weight less than 300, glycerol, glycerol formate, or water.

Additionally, when $A^{n-}$ is (a) $R^1R^2N$—$COO^-$ anion and $B^{m+}$ is ammonium ion of +1 valence ($^+NH_4$) or hydrazinium ion (i.e., hydrazinium ion of +1 valence ($H_3^+N$—$NH_2$) or hydrazinium ion of +2 valence ($H_3^+N$—$NH_3^+$)), the compound of general formula (I) is $R^1R^2N$—$COO^{-+NH}_4$ or $R^1R^2N$—$COO^-H_3^+N$—$NH_2$ or ($R^1R^2N$—$COO^-$)$_2$ ($H_3^+N$—$NH_3^+$), wherein one or two of $R^1$ or $R^2$ is above-mentioned R group. As these compounds $R^1R^2N$—$COO^{-+NH}_4$ or $R^1R^2N$—$COO^-H_3^+N$—$NH_2$ or ($R^1R^2N$—$COO^-$)$_2$($H_3^+N$—$NH_3^+$) already have R group, they can be directly used as compound of general formula (I) or as foaming agent. Of course, these compounds $R^1R^2N$—$COO^{-+NH}_4$ or $R^1R^2N$—$COO^-H_3^+N$—$NH_2$ or ($R^1R^2N$—$COO^-$)$_2$($H_3^+N$—$NH_3^+$) can also further react with above-mentioned epoxide so as to obtain compound (s) of general formula (I) having alkanolamine compound or alkanolamine residue in its cation moiety. When $A^{n-}$ is (a) $R^1R^2N$—NH—$COO^-$ anion and $B^{m+}$ is ammonium ion of +1 valence ($^+NH_4$) or hydrazinium ion (i.e., hydrazinium ion of +1 valence ($H_3^+N$—$NH_2$) or hydrazinium ion of +2 valence ($H_3^+N$—$NH_3^+$)), the compound of general formula (I) is $R^1R^2N$—NH—$COO^{-+NH}_4$ or $R^1R^2N$—NH—$COO^-H_3^+N$—$NH_2$ or ($R^1R^2N$—NH—$COO^-$)$_2$ ($H_3^+N$—$NH_3^+$), wherein one or two of $R^1$ or $R^2$ is above-mentioned R group. As these compounds $R^1R^2N$—NH—$COO^{-+NH}_4$ or $R^1R^2N$—NH—$COO^-H_3^+N$—$NH_2$ or ($R^1R^2N$—NH—$COO^-$)$_2$ ($H_3^+N$—$NH_3^+$) already have R group, they can be directly used as compound of general formula (I) or as foaming agent. Of course, these compounds $R^1R^2N$—NH—$COO^{-+NH}_4$ or $R^1R^2N$—NH—$COO^-H_3^+N$—$NH_2$ or ($R^1R^2N$—NH—$COO^-$)$_2$($H_3^+N$—$NH_3^+$) can also further react with above-mentioned epoxide so as to obtain compound (s) of general formula (I) having alkanolamine compound or alkanolamine residue in its cation moiety.

In general, when $A^{n-}$ is (g) anion and $B^{m+}$ is organic amine ion having m (for example 2-10, such as 3, 4, or 5) of —$N^+R^3R^4H$ groups and/or —$N^+R^3H$— groups (i.e., $B^{m+}$ is not ammonium ion of +1 valency ($^+NH_4$) or hydrazinium ion, that is to say when B is not ammonia or hydrazine), the compounds of the general formula (I) are obtained by hydrolyzation of orthoformate compounds in solvent (preferably protonic solvent or alcoholic solvent or DMF) in the presence of organic amine (M) (which is organic alkanolamine) or of compound B having at least one of above-mentioned N—R group (which is organic alkanolamine) and also of water, optionally in presence of catalyst (for example, aqueous ammonia, or organic amine, such as ethylamine, diethylamine or triethylamine). It is preferred that the amount of water in hydrolyzation is sufficient to make at least two of ester groups of orthoformate compound be hydrolyzed, more preferably, the amount of water is sufficient to make three ester groups of orthoformate compound be hydrolyzed. The hydrolyzation catalysts for orthoformates are in general basic compounds, preferably organic amines. Preferably, organic amine compound B having at least one of above-mentioned N—R groups (i.e., at least one R group bound to N atom) is obtained by the reaction of ammonia, hydrazine or above-mentioned organic amine compound (M) with epoxides [such as ethylene oxide, propylene oxide, epichlorohydrin, epibromohydrin, butylene oxide (including its various isomers such as 1,2-butylene oxide, or 2,3-butylene oxide), epoxychlorobutane (including its various isomers such as 1,2-epoxy-4-chloro-butane or 2,3-epoxy-1-chloro-butane) or styrene oxide, or a mixture of two or more of these epoxides]. In the R group, average value of q (namely polymerization degree of epoxide) is defined as above. Average value of q can be selected according to the specific applications of the polyurethane foam material. When the compounds of the general formula (I) is used to prepare thermal insulation polyurethane foam material, especially closed-cell type polyurethane foam material, taking the foaming efficiency, the odor of foaming agent, the insulating property of foams, the dimensional stability of foam cells and the dimensional stability of polyurethane foam product into account, or when the compounds of the general formula (I) is used to prepare open-cell type or semi-open-cell type polyurethane foam material, taking the foaming efficiency, the odor of foaming agent, fineness of foam cells and the dimensional stability of polyurethane foam product into account, it is preferred that q=1-5, more preferably q=1.2-

4.5, more preferably q=1.3-4, particularly preferably q=1.5-3.5, calculated as average value of q.

Preferably, the orthoformate compound is one or more selected from following compounds: tri ($C_1$-$C_8$) hydrocarbyl orthoformates, preferably tri ($C_1$-$C_7$) hydrocarbyl orthoformate, for example, trimethyl orthoformate, triethyl orthoformate, methyl diethyl orthoformate, tripropyl orthoformate, methyl dipropyl orthoformate, tributyl orthoformate, triphenyl orthoformate, tribenzyl orthoformate, diethyl acetyl orthoformate, ethyl methyl acetyl orthoformate, tri (ethylene glycol) orthoformate, tri (diethylene glycol) orthoformate, tri (triethylene glycol) orthoformate, tri (tetraethylene glycol) orthoformate, tri (polyethylene glycol) (degree of polymerization=5-10) orthoformate, tri (propylene glycol) orthoformate, tri (dipropylene glycol) orthoformate, tri (tripropylene glycol) orthoformate, tri (tetrapropylene glycol) orthoformate, tri (polypropylene glycol) (degree of polymerization=5-10) orthoformate.

Preferably, the solvent used in hydrolyzation process of orthoformates is one or more selected from, but not limited to the following solvents: methanol, ethanol, ethylene glycol, polyethylene glycol of molecular weight less than 400, polypropylene glycol of molecular weight less than 300, formamide, glycerol, glycerol formate, or water.

In order to prepare the compound (s) of general formula (I), several preparation methods can be used to prepare them. Only as examples, several representative preparation methods are described now.

According to the fifth embodiment of present invention, the present invention still provides a method for preparing organic amine salt(s) having $CO_2$-donating anion or for preparing the compound (s) of above-mentioned general formula (I) wherein $A^{n-}$ is any one or more anions of (a), (b), (c), (d), (e), (f) or (h), said method comprises first material being reacted with second material in solvent (preferably protonic solvent or alcoholic solvent), optionally in the presence of catalyst (for example aqueous ammonia, or organic amines, such as ethylamine, diethylamine or triethylamine), wherein first material is one or more selected from following compounds:

$R^1R^2N$—$COONH_4$, organic amine compound (M) salts of $R^1R^2N$—COOH, hydrazine salt of $R^1R^2N$—COOH (e.g., hydrazinium carbamate), $R^1R^2N$—NH—$COONH_4$ (e.g., ammonium carbazate), hydrazine salt of $R^1R^2N$—NH—COOH (e.g., hydrazinium carbazate), or organic amine compound (M) salt of $R^1R^2N$—NH—COOH, wherein, $R^1$ or $R^2$ is independently chosen from: H, $C_1$-$C_7$ aliphatic hydrocarbyl group (preferably $C_1$-$C_4$ alkyl) optionally substituted by hydroxyl or amino or halogen, $C_3$-$C_7$ cycloaliphatic hydrocarbyl group (cyclobutyl or cyclohexyl) optionally substituted by hydroxyl or amino or halogen, or, $C_6$-$C_{10}$ aromatic hydrocarbyl group (preferably phenyl or methoxyphenyl) optionally substituted by hydroxyl or amino or halogen;

$(NH_4)_2CO_3$, hydrazinium carbonate, ammonium hydrazinium carbonate, or organic amine compound (M) salt of carbonic acid;

$HCOONH_4$, hydrazinium formate or organic amine compound (M) salts of formic acid;

HO—$COONH_4$ (i.e., ammonium bicarbonate), hydrazinium bicarbonate, or bicarbonate of organic amine compound (M);

$R^aO$—$COONH_4$, hydrazine salts of $R^aO$—COOH, or organic amine compound (M) salts of $R^aO$—COOH;

$NH_4$ OOC—N($R^1$)—$R^b$—N($R^2$)—$COONH_4$, $R^{b'}$(—N($R^1$)—COO$)_3$($NH_4)_3$, hydrazine salt of HOOC—N($R^1$)—$R^b$—N($R^2$)—COOH, organic amine compound (M) salt of HOOC—N($R^1$)—$R^b$—N($R^2$)—COOH, hydrazine salt of $R^{b'}$(—N($R^1$)—COOH$)_3$, or organic amine compound (M) salt of $R^{b'}$(—N($R^1$)—COOH$)_3$; or $NH_4OOC$—$OR^cO$—$COONH_4$, hydrazine salts of HOOC—$OR^cO$—COOH, or organic amine compound (M) salts of HOOC—$OR^cO$—COOH;

the second material is one or more selected from a group consisting of following compounds:

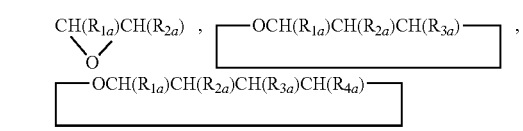

or styrene oxide;

wherein $R^1$, $R^{2'}$ $R^a$, $R^b$, $R^{b'}$, $R^c$ is defined as above, $R_{1a}$, $R_{2a}$, $R_{3a}$ or $R_{4a}$ is defined as above, and the organic amine compound (M) is defined as above.

Preferably, in the reaction for preparing compound (s) of general formula (I) wherein $A^{n-}$ is (a), (b), (c), (d), (e), (f) or (h), the mole ratio of the first material to the second material is in general 1:1.3-5, preferably 1:1.5-4.5, more preferably 1:1.6-4, for example 1:1.5 to 1:3.

Preferably, the first material is one or more selected from a group consisting of following compounds:

ammonium carbamate, organic amine (M) carbamate (referred simply to amine carbamate), hydrazinium carbamate, ammonium carbazate, hydrazinium carbazate, organic amine compound (M) salts of $H_2N$—NH—COOH, ammonium N-substituted carbamate ($R^1R^2N$—$COO^{-+}NH_4$, or referred to ammonium salt of $R^1R^2N$—COOH, wherein $R^1$ or $R^2$ can not simultaneously be H), organic amine (M) salts of N-substituted carbamic acid (i.e., the salts formed from $R^1R^2N$—COOH and M, or referred simply to amine carbamate, wherein $R^1$ or $R^2$ can not simultaneously be H), ammonium carbonate, organic amine M salts of carbonic acid (i.e., salt of $H_2CO_3$ and M, referred to amine carbonate), hydrazinium carbonate, ammonium hydrazinium carbonate, ammonium formate, organic amine M salts of formic acid (i.e., salts of formic acid and M, referred simply to amine formate), hydrazinium formate, ammonium bicarbonate, organic amine (M) bicarbonate (i.e., bicarbonate of M, referred to amine bicarbonate), hydrazinium bicarbonate, $R^aO$—$COONH_4$, M salts of $R^aO$—COOH, hydrazine salts of $R^aO$—COOH, $NH_4OOC$—N($R^1$)—$R^b$—N($R^2$)—$COONH_4$, $R^{b'}$(—N($R^1$)—$COONH_4)_3$, M salts of HOOC—N($R^1$)—$R^b$—N($R^2$)—COOH, hydrazine salts of HOOC—N($R^1$)—$R^b$—N($R^2$)—COOH, M salts of $R^{b'}$(—N($R^1$)—COOH$)_3$, hydrazine salts of $R^{b'}$(—N($R^1$)—COOH$)_3$, $NH_4OOC$—$OR^cO$—$COONH_4$, organic amine M salts of HOOC—$OR^cO$—COOH, or hydrazine salts of HOOC—$OR^cO$—COOH, wherein M is the above-mentioned organic amine compound (M).

In the present application, $^+MH$ is referred to cation formed by bonding of organic amine (M) with one or more of hydrogen ion ($H^+$).

Preferably, the second material is one or more selected from a group consisting of following compounds:

ethylene oxide, propylene oxide, epichlorohydrin, epibromohydrin, butylene oxide (including its various isomers such as 1,2-butylene oxide or 2,3-butylene oxide), epoxychlorobutane (including its various isomers such as 1,2-epoxy-4-chloro-butane or 2,3-epoxy-1-chloro-butane) or styrene oxide.

Preferably, the present invention still provide a method for preparing compound (s) of general formula (I) wherein $A^{n-}$ is any one or more anions of (a), (b), (c), (d), (e), (f) or (h), said method comprises: the reaction of ammonium salt or hydrazinium salt (such as ammonium carbamate, ammonium carbamate substituted on its amino group by hydroxyalkyl or hydroxyalkyl alkoxy, hydrazinium carbamate, ammonium carbazate, hydrazinium carbazate, ammonium carbonate, hydrazinium carbonate, ammonium hydrazinium carbonate, hydrazinium formate, ammonium formate, hydrazinium bicarbonate or ammonium bicarbonate, or a mixture of two or more of them) or organic amine salt (such as organic amine M salts of carbamic acid, organic amine M salts of carbamic acid substituted on its amino group by hydroxyalkyl or hydroxyalkyl alkoxy, organic amine M salts of carbazaic acid, organic amine M salts of N-hydroxyalkyl or N-hydroxyalkylalkoxy substituted carbazic acid, organic amine M salts of carbonic acid, organic amine M salts of formic acid or organic amine M bicarbonate, or a mixture of two or more of them) as first material with the above epoxides [such as ethylene oxide, propylene oxide, epichlorohydrin, epibromohydrin, butylene oxide (including its various isomers such as 1,2-butylene oxide, 2,3-butylene oxide), epoxychlorobutane (including its various isomers such as 1,2-epoxy-4-chlorobutane or 2,3-epoxy-1-chlorobutane oxide) or styrene oxide, or a mixture of two or more of these epoxides] as second material in a solvent (preferably protonic solvent or DMF, e.g. water) optionally in the presence of catalyst (for example aqueous ammonia or organic amines such as ethylamine, diethylamine or triethylamine), wherein the first material is formed by one or more of anions selected from (a), (b), (c), (d), (e), (f) or (h) with ammonia or hydrazine or with one or more of above-mentioned organic amine compound (M). Or alternatively, a method (it is not a preferred embodiment) includes addition reaction and neutralization, that is to say, the above method to prepare compound (s) of general formula (I) comprises: at first, ammonia, hydrazine or one or more of above-mentioned organic amine compound (M), are reacted with the above epoxides (such as ethylene oxide, propylene oxide, epichlorohydrin, epibromohydrin, butylene oxide (including its various isomers such as 1,2-butylene oxide, 2,3-butylene oxide), epoxychlorobutane (including its various isomers such as 1,2-epoxy-4-chlorobutane or 2,3-epoxy-1-chlorobutane) or styrene oxide, or a mixture of two or more of these epoxides) as second material, and then the resulting addition compounds are neutralized with one or more of corresponding acid compounds as the precursor of anion $A^{n-}$, i.e., one or more of acid compounds or acidic compounds (for example, $CO_2$, carbamic acid or formic acid) which can generate one or more anions of (a)-(g). Preferably, the resultant compounds are neutralized to pH no less than 7.5, more preferably no less than 7.8, more preferably no less than 8. The pH of ammonium formate (melting point 116° C.), hydrazinium formate or organic amine M salts of formic acid foaming agent is in a range of 5.5-6.5, more preferably is in a range of 5.5-6.0. The pH of the compound of the general formula (I) wherein $A^{n-}$ is formate (c) is 5.5-6.5, more preferably 5.5-6.0. According to the sixth embodiment of the present invention, the present invention still provide a method for preparing organic amine orthoformate compounds having $CO_2$-donating anion or for preparing compound of the general formula (I) wherein $A^{n-}$ is anion represented by (g), said method comprise: orthoformate compound (s) being hydrolyzed in solvent (preferably protonic solvent or alcoholic solvent, for example water) and in the presence of organic amine M (which is organic alkanolamine) or of compound B having at least one of above-mentioned N—R group (which is organic alkanolamine), optionally in the presence of catalyst (for example aqueous ammonia or organic amines such as ethylamine, diethylamine or triethylamine). It is preferred that the amount of water in hydrolyzation is sufficient to make at least two of ester groups of orthoformate compound be hydrolyzed, more preferably, the amount of water is sufficient to make three ester groups of orthoformate compound be hydrolyzed.

In the sixth embodiment according to the present invention, the organic amine compound (B) is obtained by the reaction of hydrazine and optional ammonia as starting material or as initiator with epoxide, wherein the epoxide is one or more epoxides selected from the following epoxides:

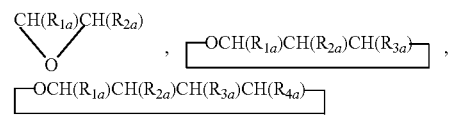

or styrene oxide.

It is preferred in the present application that at least one of $A^{n-}$ or $B^{m+}$ comprises hydrazino group or substituted hydrazino group when the compound of general formula (I) is hydrazino alkanolamine salt compound (i.e., the compound of general formula (I) according to the third embodiment). In the method according to the fifth embodiment for preparing the hydrazino alkanolamine salt compound (s) of general formula (I), at least one of the first materials comprises hydrazine or comprises hydrazino group. In the method according to the sixth embodiment for preparing the hydrazino alkanolamine salt compound (s) of general formula (I), at least one of the organic alkanolamine compound (B) comprises hydrazine or comprises hydrazino group.

It is preferred in the present application that, organic amine compound (B) having at least one of above-mentioned N—R groups (i.e., at least one R group bound to N atom) is obtained by reaction of ammonia, hydrazine and/or above-mentioned organic amine compound (M) with epoxides (such as ethylene oxide, propylene oxide, epichlorohydrin, epibromohydrin, butylene oxide (including its various isomers such as 1,2-butylene oxide, or 2,3-butylene oxide), epoxychlorobutane (including its various isomers such as 1,2-epoxy-4-chloro-butane or 2,3-epoxy-1-chloro-butane) or styrene oxide, or a mixture of two or more of these epoxides). In the R group, q is average value (namely polymerization degree of epoxide), defined as above. In the method for preparing compound (s) of general formula (I) wherein $A^{n-}$ is (g), the mole ratio of ammonia or organic amine compound (M) to epoxide is preferably 1.3-7, more preferably 1.5-4, more preferably 1.5-3. The compound of general formula (I) wherein $A^{n-}$ is (g) can be suitably used as foaming agent to prepare thermal insulation polyurethane foam material. That is to say, the present invention still provide a method for preparing compound of general formula (I) wherein $A^{n-}$ is anion represented by (g), said method comprise: ammonia or one or more of organic amine compound (M) is reacted with epoxide as second material to prepare organic amine compound B having at least one of above-mentioned N—R group (i.e., at least one R group bound to N atom); and then, orthoformate compound is hydrolyzed in solvent (preferably protonic solvent or alcoholic solvent, for example water) and in the presence of organic amine M (which is organic alkanolamine) or of compound B having at least one of above-mentioned N—R group (which is organic alkanolamine) and of water, optionally in the presence of catalyst (for example aqueous ammonia or organic amines such as ethylamine, diethylamine or triethylamine). It is preferred that the amount of water in hydrolyzation is sufficient to make at least two of ester groups of orthoformate compound be hydrolyzed, more preferably, the amount of water is sufficient to make three of ester groups of orthoformate compound be hydrolyzed.

Preferably, orthoformate compound is one or more compound selected from following: tri ($C_1$-$C_8$) hydrocarbyl orthoformate, preferably tri ($C_1$-$C_7$) hydrocarbyl orthoformate, for example, trimethyl orthofomnnate, triethyl orthoformate, methyl diethyl orthoformate, tripropyl orthoformate, methyl dipropyl orthoformate, tributyl orthoformate, triphenyl orthoformate, tribenzyl orthoformate, diethyl acetyl orthoformate, ethyl methyl acetyl orthoformate, di(ethylene glycol) orthoformate, propylene glycol orthoformate, or polyethylene glycol orthoformate; or alternatively R group in orthoformate conforms to characteristics of (1a), (2a) or (3a).

Preferably, in the present application, the solvent is one or more selected from the following solvents: methanol, ethanol, ethylene glycol, propylene glycol, polyethylene glycol of molecular weight less than 400, polypropylene glycol of molecular weight less than 300, glycerol, glycerol esters, or water.

The first material comprises hydrazine or hydrazino group or at least one of the first material comprises hydrazine or hydrazino group, when these materials are used to prepare hydrazino alkanolamine salt compound (s). Hydrazine is a toxic, flammable and explosive compound, hence one should read carefully the relevant use guidelines and comply strictly with the relevant requirements and provisions. According to the seventh embodiment of present invention, provided is an organic amine salt compound having $CO_2$-donating anion or a mixture thereof, wherein the salt compound or mixture is obtained by the method of the fifth or sixth embodiment. Preferably, the salt compound or mixture contains 22-96 wt %, preferably 25-95 wt %, preferably 27-90 wt %, preferably 30-85 wt %, preferably 40-80 wt %, more preferably 45-75 wt % of the salt of monoalkanolamine (for example monoethanolamine and/or monopropanolamine) and the salt of dialkanolamine (for example diethanolamine and/or dipropanolamine) (i.e., the sum of both alkanolamine salts), based on total weight of the salt compound or mixture. Or alternatively, it is preferred that the salt compound or mixture contains 15-90 wt %, preferably 17-88 wt %, preferably 20-85 wt %, preferably 25-80 wt %, more preferably 30-70 wt % of monoalkanolamine (for example monoethanolamine and/or monopropanolamine) or dialkanolamine (for example diethanolamine and/or dipropanolamine) (i.e., the sum of both alkanolamines), based on total weight of the salt compound or mixture.

According to the eighth embodiment of the present invention, provided is use of the organic amine salt compound of general formula (I) or the organic amine salt compound having $CO_2$-donating anion obtained by the method of the fifth embodiment or the sixth embodiment, as foaming agent, especially as polyurethane foaming agent, polystyrene foaming agent or polyvinyl choride foaming agent. These above-mentioned compounds in the present application can also be referred to a foaming agent of the present invention or a polyurethane foaming agent of the present invention.

Additionally, the present invention provides use of the foaming agent of present invention as polystyrene foaming agent or polyvinyl choride foaming agent, wherein $A^{n-}$ is one or more anions selected from the following anions:
 (a) $R^1R^2N$—$COO^-$ or $R^1R^2N$—$NH$—$COO^-$; wherein $R^1$ and $R^2$ each independently is H, methyl, ethyl, $H(OCH_2CH_2)_q$—, $H(OCH_2CH(CH_3))_q$—, $H(OCH(CH_3)CH_2)_q$—, $H(OCH_2CH(C_6H_5))_q$—, $H(OCH(C_6H_5)CH_2)_q$—, $H(OCH_2CH(CH_2Cl))_q$—, $H(OCH(CH_2Cl)CH_2)_q$— or $H(OCH_2CH(CBr_3))_q$—;
 (b) $CO_3^{2-}$; or
 (d) HO—$COO^-$.

Additionally, in view of the higher decomposition temperature of ammonium formate (melting point 116° C.) or organic amine (M) salts of formic acid, it is generally agreed that they are unsuitable to be used for polyurethane foaming. But based on numerous studies, the inventors of the present application surprisingly discover that the ammonium formate (melting point 116° C.) or the organic amine (M) salsts of formic acid can reacts with isocyanate group to form unstable anhydride compound when they contact with the isocyanate group, then the resultant compound rapidly decompose and release carbon dioxide gas and carbon monooxide gas, so it is necessary to take care of ventilation and explosion protection in practical situations. Additionally, hydrazinium formate has similar characteristics.

In the present application, when using ammonium formate and epoxide to prepare compound of general formula (I), it is preferred that, first, formic acid is reacted with aqueous ammonia to obtain ammonium formate aqueous solution, small amount of organic amine (for example methylamine, dimethylamine or trimethylamine, ethyl amine or diethylamine) is added thereto, thermal dehydration or concentration under reduced pressure or concentration under vaccum is carried out (for example to water content of 7-15 wt %, for example 10 wt % more or less), and then epoxide (such as ethylene oxide and/or propylene oxide) is added to carry out reaction, so as to obtain alkanolamine salt of formic acid (I). Here, addition of small amount of organic amine (for example methylamine, dimethylamine or trimethylamine, ethyl amine or diethylamine) can prevent crystallization and precipitation phenomena in foaming composition ("white material") when alkanolamine formate (I) is used to formulate foaming composition ("white material"). If hydrazinium formate and epoxide are used to prepare compound of general formula (I), the properties or application effects are obtained which are similar to or equivalent to those obtained when using ammonium formate and epoxide to prepare compound of general formula (I). Additionally, formic acid can also be used directly to react with alkanolamine compound to prepare compound of general formula (I).

In the present application, a catalysts such as methylamine, dimethylamine, alkanolamines, other amine catalysts, or bimetallic catalysts or pressurized heating can be used, when ammmonium bicarbonate as first material is reacted with the second material to prepare compound of general formula (I).

Additionally, an organic amine salt compound of following general formula (Ia): $A^{n-}[B^{m+}]p$ (Ia), which is obtained by neutralizing at least one alkanolamine compound (which is an organic amine compound (M) having at least one N—H) selected from $C_2$-$C_{12}$ alkanolamines (such as monoethanolamine, diethanolamine, triethanolamine, monopropanolamine, dipropanolamine, tripropanolamine, monoisopropanolamine, diisopropanolamine, triisopropanolamine, monobutanolamine, dibutanolamine, or tributanolamine) with corresponding acids as the precursor of anion $A^{n-}$ (e.g.

$CO_2$), can also be used directly as foaming agent, especially as polyurethane foaming agent, polystyrene foaming agent or polyvinyl choride foaming agent; despite these foaming agents are not preferred. It will generate CO gas in the foaming reaction in the case of formic acid or formate being selected as foaming agent, so it is necessary to carry out ventilation and explosion protection; if amine salt of formic acid is used as foaming agent, then the presence of isocyanate is necessary, because carbon dioxide and carbon monoxide are released only after it react with isocyanate. Those above-mentioned compounds in the present application can also refer to a foaming agent of the present invention. The polyurethane foaming agent may be used in polyurethane foaming composition. Of course, these compound foaming agents of general formula (Ia) are not preferred, because their pH value in general are below 8, even below 7.5, more even below 7.1, still more even pH=6-7. These organic amine salt compounds (Ia) (which are not prepared in situ by reaction of organic amine compound (M) with epoxide) are not preferred, when they are used to prepare thermal insulation polyurethane foam material, especially closed-cell type polyurethane foam material, taking into account foaming efficiency, odor of foaming agent, insulation property, dimensional stability of foam cells and dimensional stability of polyurethane foam material, or when they are used to prepare open cell type or semi-open cell type polyurethane foam material, taking into account foaming efficiency, odor of foaming agent, fineness of foam cells and dimensional stability of polyurethane foam material.

That is to say, if ammonia, hydrazine and/or organic amine are reacted with epoxide firstly to prepare alkanolamine and the resultant is then neutralized with acidic substance or acidic compound (e.g., carbon dioxide or carbamic acid) corresponding to anions of (a), (b), (c), (d), (e), (f), (g) or (h) to obtain organic amine salt compound of general formula (I), the pH (usually pH<7) of the resulting organic amine salt compound (i.e., alkanolamine salt), the content of $CO_2$ precursor (relevant to $CO_2$ amount released) and the activity in foaming reaction all are unsatisfactory (except the advantages in safety or cost with respect to a few compounds such as orthoformate or hydrazine). Hence, it is preferred to obtain compound of general formula (I) by the direct reaction of anion of (a), (b), (c), (d), (e), (f), (g) and/or (h) with ammonia, hydrazine and/or organic amine (M).

In addition, di-(hydroxyethyl amine) carbonate, di-(hydroxypropyl amine) carbonate, hydroxyethylamine bicarbonate, or hydroxypropylamine bicarbonate is particularly suitable as foaming agent in polystyrene foaming or polyvinyl choride foaming. These compounds belong to above compounds of general formula (I). Additionally, polyalkylenepolyamine carbonate compounds not belonging to above compounds of general formula (I), such as diethylenetriamine carbonate, triethylenetetramine carbonate, tetraethylenepentamine carbonate, dipropylenetriamine carbonate, tripropylenetetramine carbonate, tetrapropylenepentamine carbonate, are also suitable as foaming agent in polystyrene foaming or polyvinyl choride foaming.

In general, amine salt of formic acid foaming agent containing (c) formate ion can not be directly used in polystyrene foaming agent or polyvinyl choride foaming agent.

Additionally, the inventors of the present application surprisingly discover that miscibility of ammonium formate or hydrazinium formate with polymer polyols is much better, that is to say ammonium formate or hydrazinium formate can be directly dissolved in polymer polyols, hence, ammonium formate or hydrazinium formate can be used directly as polyurethane foaming agent, accordingly, the present application still provides use of ammonium formate or hydrazinium formate as foaming agent, especially as polyurethane foaming agent. The ammonium formate aqueous solution or hydrazinium formate aqueous solution does not crystallize and precipitate when ammonium formate aqueous solution or hydrazinium formate aqueous solution contains small amount (for example 0.5-15 wt %, such as 1-8 wt %, more preferably 2-6 wt %) of organic amines, for example methylamine, dimethylamine, trimethylamine or monoethanolamine.

The foaming agents of present invention (i.e., compounds of general formula (I), or the organic amine salt compounds having $CO_2$-donating anion, obtained by the methods of the fifth embodiment or the sixth embodiment) have the following characteristics:

1) without additionally adding basic compound, the pH value of foaming agent (i.e., compounds of general formula I) of present invention, except ammonium formate, hydrazinium formate or organic amine (M) salts of formic acid, is in the range of 7.5-10, preferably 7.8-9.5, more preferably 8-9; the pH value of ammonium formate (melting point 116° C.), hydrazinium formate or organic amine (M) salts of formic acid foaming agent is in the range of 5.5-6; or the pH value of compounds of general formula (I) wherein $A^{n-}$ is formate (c) is in a range of 5.5-6;

2) the content of alkali metals or alkaline earth metals is 0-200 ppm by mass, preferably below 150 ppm, more preferably below 100 ppm, more preferably below 50 ppm, more preferably below 20 ppm, more preferably below 10 ppm, more preferably below 5 ppm, most preferably is below detection limit or is 0 ppm;

3) the water content or the content of water as solvent is 0-40 wt %, preferably 5-35 wt %, more preferably 10-30 wt %, more preferably 15-25 wt %;

4) the thermal decomposition temperature is 36-120° C. and it releases $CO_2$ gas after being decomposed; wherein certain foaming agents of present invention having higher decomposition temperature may become less stable upon contacting with NCO group, and thus they can decompose and release $CO_2$ under the temperature of 45-70° C.;

5) it is preferred that the foaming agents of present invention contain at least one R group per molecule, said R group is for example $HOCH_2CH_2$—, $HOCH_2CH(CH_3)$—, $HOCH(CH_3)CH_2$—, $HOCH_2CH(C_6H_5)$—, $HOCH(C_6H_5)CH_2$—, $HOCH_2CH(CH_2Cl)$—, $HOCH(CH_2Cl)CH_2$—, $HOCH_2CH(CBr_3)$— or $HOCH(CBr_3)CH_2$—; further preferably, the foaming agent of present invention comprises more than one (preferably 2-5, such as 2 or 3) of compounds having general formula (I) and contains, on average, 1.5-5 of R groups per molecule, said R group is for example $HOCH_2CH_2$—, $HOCH_2CH(CH_3)$—, $HOCH(CH_3)CH_2$—, $HOCH_2CH(C_6H_5)$—, $HOCH(C_6H_5)CH_2$—, $HOCH_2CH(CH_2Cl)$—, $HOCH(CH_2Cl)CH_2$—, $HOCH_2CH(CBr_3)$— or $HOCH(CBr_3)CH_2$—;

6) 30-100%, preferably 50%-100%, more preferably 70%-100%, more preferably 85%-100% of N atoms in the foaming agent of present invention have N—H covalent bond.

7) in the foaming agent of present invention, the total content of compounds of general formula (I) and water is 70-100%, more preferably is 80-99.999%, more preferably is 85-99.0% (the foaming agent contains solvent (s), and may contain small amount of non-metallic impurity), based on the total weight of the foaming agent;

8) by infrared spectrum analysis, certain foaming agents of present invention have a stretching vibration single peak belonging to N—H of secondary amine salt in a range of 2932-2970 cm, a flexural vibration single peak belonging to N—H of secondary amine salt in a range of 1555-1566 cm$^{-1}$, and, additionally, a strong and wide stretching vibration peak belonging to OH of hydrogen bond in a range of 3200-3400 cm$^{-1}$, these indicate that the foaming agents have hydroxy and secondary amino group, and also contain water. Hence, the foaming agents of present invention comprise one or more of alkanolamine compounds and generally contain water.

More preferably, the compound of general formula (I) contains, on average, 1.5-5 of R groups per molecule.

In the present application, preferably, the R group is HOCH$_2$CH$_2$—, HOCH$_2$CH(CH$_3$)—, HOCH(CH$_3$)CH$_2$—, HOCH$_2$CH(C$_6$H$_5$)—, HOCH(C$_6$H$_5$)CH$_2$—, HOCH$_2$CH(CH$_2$Cl)—, HOCH(CH$_2$Cl)CH$_2$—, HOCH$_2$CH(CBr$_3$)— or HOCH(CBr$_3$)CH$_2$—.

According to the ninth embodiment of present invention, the present invention still provides a polyurethane foaming composition, the composition comprises: 0.01-100 wt % of above-mentioned compounds of general formula (I) (or organic amine salt compounds having CO$_2$-donating anion, obtained by the second or the third embodiment); 0-50 wt % of physical foaming agent; 0-5 wt % of water, and 0.0-99.99 wt % of polymer polyol (s); wherein the weight percentage is based on the total weight of the polyurethane foaming composition. Preferably, the composition comprises: 0.1-80 wt % (more preferably 1-70 wt %, more preferably 3-60 wt %, more preferably 5-50 wt %, more preferably 7-40 wt %, such as 10 wt % or 15 wt %) of compounds of general formula (I); 0-40 wt % of physical foaming agent; 0-4 wt % of water, and 20.0-99.9 wt % (more preferably 30-99 wt %, more preferably 40-97 wt %, more preferably 50-95 wt %, more preferably 60-93 wt %, such as 90 wt % or 85 wt %) of polymer polyol; wherein the weight percentage is based on the total weight of the polyurethane foaming composition. It is preferred that the foaming composition of present invention contains, in all, 0.5-4 wt %, more preferably 0.8-2.5 wt %, more preferably 1-2.2 wt % of water.

Preferably, the foaming composition further comprises: foam stabilizer, catalyst, flame retardant and the like. These auxiliaries are often used in the field of polyurethane.

Preferably, the polymer polyol is selected from: polyether polyol, polyester polyol, polyether-polyester polyol, polycarbonate diol, polycarbonate-polyester polyol, polycarbonate-polyether polyol, polybutadiene polyol or polysiloxane polyol. The average functionality of the polymer polyol is in general 2-16, preferably 2.5-10, more preferably 3-8.

Preferably, the physical foaming agent is at least one selected from n-pentane, isopentane, cyclopentane, other alkanes having a boiling point in a range of 0-100° C., HCFC-141b, HFC-245fa, HFC-365mfc, LBA, FEA-1100, other fluorochlorohydrocarbons having a boiling point in a range of 0-100° C., or esters such as methyl formate.

In general, the foaming composition of present invention is transparent or clear. It is preferred that the foaming composition for hard polyurethane foam is transparent or clear liquid or is semi-transparent or milk-white but homogeneous liquid, or the foaming composition for flexible polyurethane foam is transparent or milk-white homogeneous liquid. This indicates that the foaming agent of present invention can be dissolved or be uniformly dispersed in polymer polyol. In general, a transparent or clear system is formed by mixing of the foaming agent or foaming agent composition of present invention with most of polyetherpolyols. In general, a transparent or clear system is formed by mixing of the foaming agent or foaming agent composition of present invention with polyester polyol, but it is possible that a milk-white and homogeneous system is formed by mixing of the foaming agent or foaming agent composition of present invention with a few kinds of polyester polyols.

The polyurethane foaming composition (also referred to as "white material") of present invention has following characteristics: 1. it comprises alkanolamine salts or alkanolamine compounds (for example, the compound of general formula (I) releases CO$_2$ after thermal decomposition while leaving alkanolamine compounds); 2. it is a transparent or clear or semi-transparent or milk-white but homogeneous liquid; 3. it releases CO$_2$ in the case of being heated (for example under a temperature of 40-80° C.) or adding acid(s) such as mineral acid or organic acid stronger than carbonic acid, its peak decomposition temperature is in general 45-65° C.; 4. the color of the resultant material mixture rapidly (for example 0.2-4 seconds, such as 1-2 seconds) changes into milk white, when the foaming composition (i.e., "white material") contacts or mixs with isocyanate or polyisocyanate (for example MDI or TDI). In the present invention, the color of the foaming material rapidly changes into milk white, accompanied by its volume quickly expanding, but this process is not really the rising of foaming material mixture, after which the material mixture actually begins to rise. Comparatively speaking, when using water or using water and physical foaming agent as foaming agent, the color changing to milk white and the rising of foam take place at the same time, and both have a delay.

In spite of the fact that the foaming composition ("white material") can comprise small amount of water as auxiliary foaming agent, in present invention, the compounds of general formula (I) of present invention preferentially decompose to release CO$_2$, i.e., foaming preferentially, hence, small amount of water existed therein does not affect foaming process or does not affect properties of polyurethane foam product. That is to say, in certain cases, a small amount of water exists in the compounds of general formula (I) (i.e., foaming agent), the water exists therein in a form of single molecule which is bound to or associated with the compound of general formula (I), and the water is either advantageous for foaming or does not involve in foaming, i.e., does not consume NCO groups. The inventors of the present application discovered by research that a small amount of water (i.e., associated water) existed in the compounds of general formula (I) (i.e., the foaming agent) even does not take part in foaming reaction, that is to say it does not deplete NCO groups. This discovery is unexpected.

It is preferred that the polyurethane foaming composition ("white material") of present invention contains 1-5 wt % of water, when the polyurethane foaming composition (white material) of present invention comprises compound of general formula (I) wherein A$^{n-}$ is (f) HCOO$^-$ (formate radical), which is used to decrease amount of carbon monoxide (CO) released in the foaming process.

The present invention still provide polyurethane foam material which is formed by the mixing and reacting of above-mentioned polyurethane foaming composition with polyisocyanate monomer (such as MDI or TDI) and/or isocyanate terminated prepolymer. In general, the weight ratio of polyurethane foaming composition to polyisocyanate monomer and/or isocyanate terminated prepolymer is for example in a range of 0.5:1-2:1, preferably 0.5:1-1:1, with respect to the foaming composition for hard polyurethane foam, or in a range of 1:1-2:1, with respect to the foaming composition for flexible polyurethane foam. Preferably, said weight ratio should make equivalent ratio of active hydrogens in the foaming composition to —NCO groups contained in polyisocyanate monomer and/or isocyanate terminated prepolymer to be 0.6-1.2:1, more preferably 0.7-0.9:1, i.e., a slight excess of NCO relative to active hydrogen.

The present invention still provides use of polyurethane foam material in polyurethane spray coating, refrigerator and refrigerating cabinet insulation, container insulation, building insulation board, colour steel sheet, refrigerated warehouse plate, pipeline insulation, LNG transportation insulation, high resilience foam, low resilience foam and the like.

Preferably, the organic amine salt compounds of general formula (I) have at least two of active hydrogen, for example 2-10, preferably 3-6 of active hydrogen. The said active hydrogen is present in a form of primary amine group, secondary amine group or hydroxyl group. Accordingly, the organic amine salt compound of general formula (I) can relase $CO_2$ to participate in foaming and also take part in chain-extending and/or crosslinking to enhance strength (i.e., mechanical strength) of foam cells, such that the polyurethane foam as prepared by hand mixing materials in laboratory square mold) have good dimensional stability. Especially, if the density of polyurethane foam is less than 25 kg/m$^3$, it is generally believed that the polyurethane foam obtained by using only water as foaming agent in the prior art would encounter a serious shrinkage phenomena, but the polyurethane foam as prepared by hand mixing in laboratory square mold using the compounds of general formula (I) of present invention as foaming agent has excellent dimensional stability, especially there is hardly any macroscopic shrinkage phenomena in the foam material after being stored under the environmental condition or room temperature condition for at least 5 months. For example, according to China National Standards GB/T 8811-2008, except for change of storing time, the shrinkage ratio (length dimension change rate ($\varepsilon_L$) or width dimension change rate ($\varepsilon_w$) or thickness dimension change rate ($\varepsilon_r$)) of the polyurethane foam material prepared by present invention is in general below 7%, more preferably below 5%, further preferably below 3%, even more preferably below 1%, afte the polyurethane foam (density <25 kg/m$^3$) is stored under room temperature (23±2° C.) for 5 months.

The organic amine salt compounds of the general formula (I) of present invention can be specifically designed according to various application fields of polyurethane foam material prepared.

For example, the mole ratio of the first material to the second material in the reaction for preparing the compounds of the general formula (I), wherein $A''^-$ is one of (a)-(f) or (h), is in general 1:1.3-3.5, preferably 1:1.5-3, when the foaming composition ("white material") of present invention is to prepare polyurethane foam material used as thermal insulating material of refrigerator, refrigerating cabinet, refrigeration cargotainer or refrigeration truck, or is to prepare flexible polyurethane foam materials with high resilience rate or low resilience rate and the like. Additionally, the mole ratio of the first material to the second material is in general 1:2.8-5, preferably 1:3-4.5, more preferably 1:3.3-4 when the foaming composition ("white material") of present invention is used in spray-coating application.

Preferably, the reaction temperature for preparing the compounds of the general formula (I) is in a range of 0-200° C., for example 10° C., 20° C., 30° C., 40° C., 50° C., 60° C., 70° C., 80° C., 90° C., 100° C., 110° C., 120° C., 130° C., 130° C., 150° C., 160° C., 170° C., 180° C. or 190° C. The reaction pressure is in a range of 0.1-1.5 MPa, for example 0.3 MPa, 0.6 MPa, 0.9 MPa or 1.2 MPa. The reaction time is in a range of 0.5-20 hours, for example 0.5, 1, 2, 3, 4, 5, 6, 7, 8, 9, 10, 11, 12, 13, 14, or 15 hours.

The decomposition temperature of the compounds of the general formula (I) of the present invention is in general in a range of 45-120° C., preferably 50-70° C., or is in a range of 45-70° C. when contacting with isocyanate.

Advantageous technological effects or advantages of present invention

1. The compounds of the general formula (I) of the present invention or the foaming agents of the present invention have appropriate decomposition temperature, or have appropriate decomposition temperature when coming into contact with isocyanate. It has storage stability at room temperature, and on the other hand, it can releases carbon dioxide gas with a reasonable speed when the foaming reaction system is heated up during polyurethane foaming process, such that the resultant foam material has ideal characteristics, such as distribution density of cells, dimension uniformity of cells. The most preferred foaming agents in the present invention are carbamates or carbonates of the general formula (I), due to their appropriate decomposition temperature, appropriate carbon dioxide releasing speed, excellent distribution density of cells of the resulting foam, excellent size uniformity of cells of the resulting foam. The average cell diameter of the foam, formed under the same foaming conditions as those using a physical foaming agent, is significantly smaller than that of the foam obtained by using physical foaming agent such as water or cyclopentane, the number of cells in a unit volume of foam is far more than that of the foam obtained by using other foaming agents, thereby giving the resulting foam material a favorable thermal insulation property. The foaming agent of present invention (especially with respect to carbamate and/or carbonate) has higher pH value (ph>7.5), the content of acid radicals per unit weight is high (or the amount of $CO_2$ released is large), and this foaming agent has higher reactivity when it used as foaming agent, especially as polyurethane foaming agent.

2. The compounds of the general formula (I) of the present invention have a solubilizing group R, said compounds (I) can be dissolved or dispersed uniformly on molecular level in polymer polyols such as polyether polyol and/or polyester polyol, or in polyvinyl choride (PVC) resin or polystyrene (PS) resin, thereby ensuring uniformity of foaming and avoiding local excess foaming.

3. The compounds of general formula (I) of present invention comprise alkanolamine residue or alkanolamine compound. Because the decomposition products (i.e. alkanolamine compounds) produced after the compounds (I) as foaming agent being decomposed to release $CO_2$ gas still contain at least two active hydrogen, the decomposition products are suitable for use as chain-extending agent and/or cross-linking agent, which means that the compounds of general formula (I) of present invention not only can act as "foaming point" but also can act as "chain-extending point" or "cross-linking point", and thus enhance remarkably the mechanical strength of foam cells and make the polyurethane foam otained have good dimensional stability. The polyurethane foam product has hardly any obvious shrinkage phenomena and no cell collapsing phenomena after stored for several months and even for one year. Especially, the foam material still has good dimensional stability after placed under higher temperature (such as 40-60° C., even 40-70° C.) for a longer time (such as 10 days).

4. The compounds of the general formula (I) of present invention are not easy to volatilize, do not contain metal ion (metal ion is corrosive to metal substrate), and can wholly or mostly replace chlorofluorocarbon foaming agents, and thus have a significance for environmental protection, and the foaming effect is clearly superior to that obtained by using other foaming agents in the prior art.

5, When used in combination with cyclopentane as a foaming agent, the thermal insulation property of the foam can be significantly improved as compared with cyclopentane alone. When the compounds of general formula (I) are used in combination with chlorofluorocarbons such as HCFC-141b or HFC-365mfc as a blowing agent, the thermal insulation property of the foam can be significantly improved compared to the use of chlorofluorocarbons alone. At present, with respect to a certain foaming agent or specific chlorofluorocarbon foaming agent, it is usually to select specific polyether polyol having better miscibility or intermiscibility with the above-decribed foaming agent, however, if using the foaming agent of present invention, it is not necessary to select specific polyether polyol or polyester polyol, and the foaming agent of present invention has a wide application scope, such that various polyester polyol and/or polyether polyol can be used in the foaming composition.

6. The foaming agent of present invention has amino group, has self-catalysis function, and can reduce the use amount of polyurethane foaming catalyst and can at least reduce the amount of pre-catalyst or even dispense with the use of pre-catalyst.

7. Comparing to prior art, the polyurethane foaming agent provided by present invention does not contain chlorofluorocarbons or chlorine and fluorine elements, its ODP (ozone depletion potential) is 0, its GWP (global warming potential) equal to 1. It is the most environmentally friendly polyurethane foaming agent with excellent performances and particurly excellent low temperature performance, and the thermal conductivity measured at −160° C. is about 20% lower than the best physical foaming agent in the prior art, which makes the foam can be used for insulation of long-distance natural gas pipeline. Another advantage is that the combination use of the foaming agent with cyclopentane can greatly lower the coefficient of heat conductivity of the resulting foam material, which can greatly lower the power consumption of refrigerator or refrigerating cabinet and the like. The polyurethane foaming agent provided by the present invention can replace all existing halogen-containing hydrocarbon physical foaming agents, to meet the production and applications of polyurethane foam materials.

8. The dimensional change ratio or shrinkage ratio of the polyurethane foam material prepared by using the compounds of general formula (I) of the present invention (as prepared in laboratory square mold by hand mixing) is ≤4.5%, preferably ≤1.5%, more preferably ≤0.5% (according to Chinese National Standards GB/T 8811-2008, the storage time is determined according to the requirement in this standard or even is 5 months). Additionally, for example in the case of foam density of 34-42 kg/m$^3$, the coefficient of heat conductivity w/m·k (10° C.) is in a range of 0.01900-0.02200, preferably in a range of 0.01910-0.02150.

9. The compounds of the general formula (I) of the present invention or mixture thereof contain a small amount of water, the water exists therein in a form of single molecule which is bound to or associated with the alkanolamine salt compound of general formula (I), and thus the water existed therein in a form of single molecule is advantageous for foaming and can enhance properties of the resulting foam product. Although a small amount of water is also used as foaming agent or auxiliary foaming agent in the prior art, the water often exists therein in a form of water molecule clusters or water molecule groups (i.e., water droplets), especially, these water molecule clusters have different dimensions from each other, which makes the foaming of the foaming composition progress unevenly, especially results in local crimping of the foam and influences various properties of the foam product.

BRIEF DESCRIPTION OF DRAWINGS

FIG. 10, FIG. 12 and FIG. 14 are photographs of inventive polyurethane foams obtained by using compound A-4 as foaming agent.

FIG. 11, FIG. 13 and FIG. 15 are photographs of comparative polyurethane foams obtained by using water as foaming agent.

FIG. 16 is a SEM photograph of the polystyrene foam material of example 34.

DETAILED DESCRIPTION OF THE INVENTION

Figure 1:
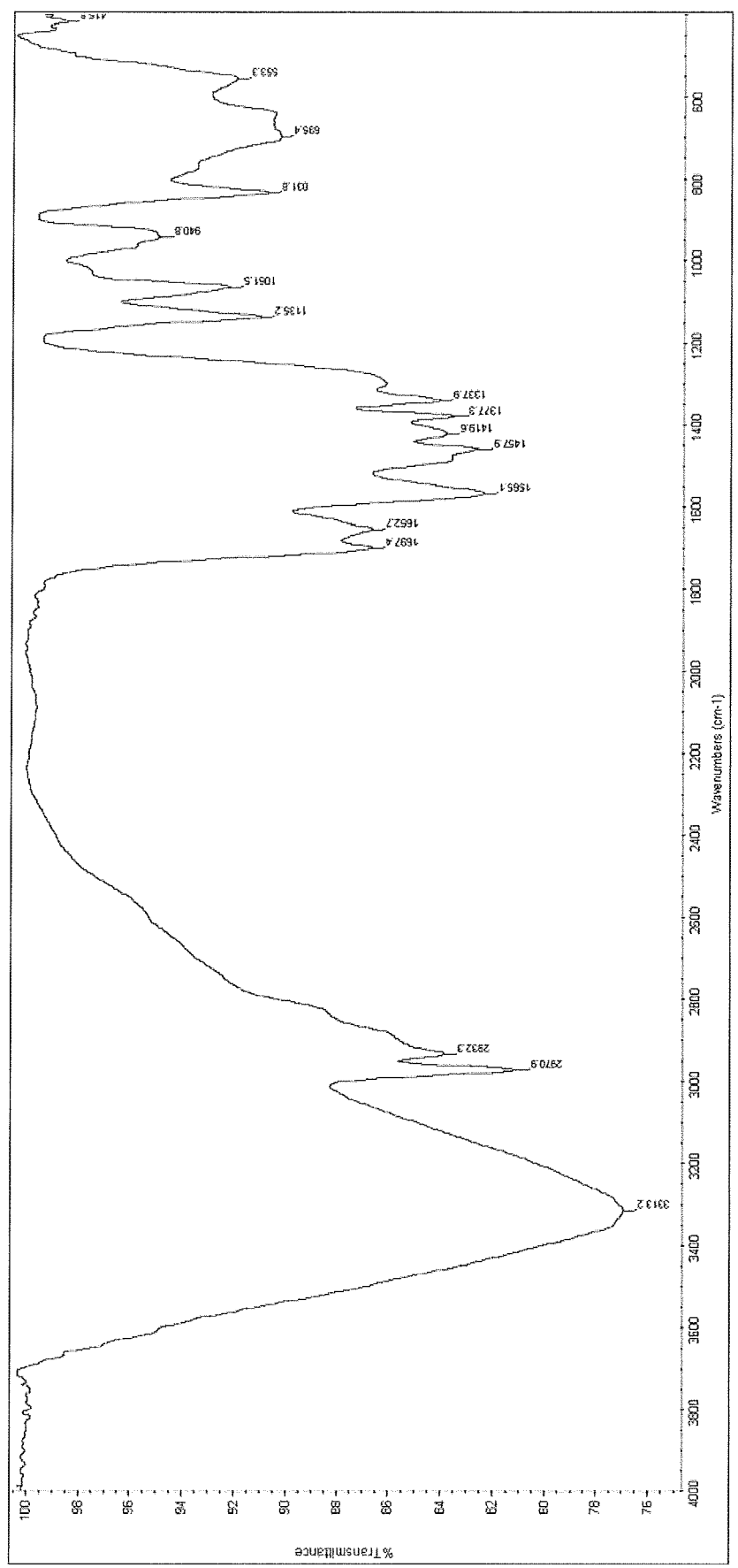
FIG. 1 is an infrared spectrogram of the product of example A-3.

The further description for the present invention is made by combination with the following examples.

In the present application, the polyether polyols or the polyester polyols usually used to prepare polyurethane foam or used in foaming composition are selected from following: polyether 4110, 450, 400A, MN500, SU380, SA380, 403, SA460, or G350; polyester CF6320, DM2003, YD6004, AKS7004, or CF6255. The usually used catalyst is selected from: 33LV (A-33): 33% dipropylene glycol solution of triethylenediamine, N,N-dimethylethanolamine, N,N-dimethyl benzylamine, 70% dipropylene glycol solution of di (dimethylaminoethyl) ether, 70% diethylene glycol solution of potassium octanoate, dibutyltin dilaurate, PT303, PT304, postassium acetate, PC-8 (N,N-dimethyl cyclohexylamine), PC-5, PC-41, monoethanolamine, diethanolamine, triethanolamine, JXP-508, JXP-509, TMR-2, TMR-3, or TMR-4. The usually used flame retardants: TCPP, TCEP, DMMP, ammonium chloride, aluminium hydroxide powder, DM1201, DM1301, tetrabromophthalate diol. The usually used silane surfactants: DC8545, AK-158, AK-8805, AK-8812, AK-8809, AK-8818, AK-8860, DCI990, DC5188, DC6070, DC3042, or DC3201. Non-silane surfactants: LK-221, or LK-443.

The safety instructions: for safety, in the case of using epoxide compound in the present invention, the reactor must be treated and protected with inert gases (such as nitrogen gas or argon gas) before and after the reactants being charged into the reactor in order to avoid explosion. Additionally, for safety, in the case of adding ethylene oxide, it is preferred that ethylene oxide is added batchwise to the reactor, whereas propylene oxide can be added to reactor all at once or also batchwise. The reactor is generally a pressure reactor equipped with a cooling device, unless otherwise stated. The epoxide compound should be slowly added to the reactor in batch, and even those relatively safe epoxides should also be slowly added to the reactor in batch and the reaction conditions such as reaction rate should be controlled to ensure safety. The hydrazine hydrate is also a flammable, explosive and toxic compound, and and must be used in accordance with relevant requirements and regulations.

The various properties of foam are tested according to Chinese National Standard GB/T 26689-2011 (the rigid polyurethane foamed plastics for refrigerators and refrigerating cabinets) in following examples. The dimension of the testing specimen is generally 10*10*2.5 cm.

The coefficient of heat conductivity is tested according to Chinese National Standards GB/T 10294-2008 or GB/T 10295-2008. The average temperature used is 10° C., and cold-hot-plate temperature difference is 15-20° C. The apparent (core) density of the foam is tested according to GB/T 6343-2009. The low temperature dimensional stability of the foam is tested according to GB/T 8811-2008 at the temperature of −30° C.±2° C. The compression strength of the foam is tested according to GB/T 8813-2008. The closed-cell ratio (i.e., closed-cell volume percentage) of the foam is tested according to GB/T 10799-2008.

With respect to the measuring method of the content of various alkanolamines (such as monoethanolamine, diethanolamine, triethanolamine, monopropanolamine, dipropanolamine or tripropanolamine) in the compounds of general formula (I) or the compound mixture comprising such compounds, gas chromatography can be used. The gas chromatograph is fitted with hydrogen flame ionization detector (FID), and the mass concentration of the compounds of general formula (I) is about 10 mg/mL, used as a standard solution. The gas phase chromatography conditions: HP-5 adsorption capillary column (30 m*0.32 mm i.d.*0.25 μm, 5% phenyl methyl-siloxane); the column temperature is regulated by temperature programming, its initial temperature is set at 80° C. and is maintained for 3 min., then the column temperature is increased to 250° C. at the heating rate of 25° C./min and then is maintained for 5 min.; the injection port temperature is 250° C.; the detector temperature is 260° C.; the carrier gas is high purity nitrogen gas, and its flow rate is 1.5 mL/min.; the combustible gas is hydrogen gas, and its flow rate is 30 mL/min.; the combustion-supporting gas is air, and its flow rate is 300 mL/min.; the makeup gas is nitrogen gas, and its flow rate is 25 mL/min.; the manner of sample injection is split stream sampling, the split ratio: 30:1, and the sample load is 1 μL.

A) Preparing the Compounds of the General Formula (I) from Ammonium Carbamate or Organic Amine (M) Salts of Carbamic Acid Example A-1

1.4 tons or ammonium carbamate (molecular weight 78.07), 0.7 ton of ethylene glycol and 0.9 ton of water are charged into a stainless steel autoclave equiped with a cooling water jacket (hereinafter referred to reactor, for short), the stirrer is turned on to make ammonium carbamate be dissolved slowly (not always dissolve completely), the reactor is purged with nitrogen gas, then the reactor is closed and the stirrer is started again. Propylene oxide (1.7 tons in total, molecular weight 58.08, boiling point 34° C.) is fed into the reactor, wherein the charging rate of propylene oxide should be controlled so as to keep the pressure in the reactor at no more than 0.6 MPa, the temperature is increased slowly with continual agitation, and the reaction system is allowed to react for 15 hours while the reaction temperature is controlled at below 70° C. After the completion of the reaction, the temperature of the reaction system is reduced slowly to 50° C., and then some unnecessary water and the unreacted propylene oxide are removed slowly from the reaction system by controlling the vacuum degree below 600 millimetres of mercury (preferably less than 500 mmHg) (for example to achieve the water content of below 20 wt %). The vacuum of the system is released, and the reaction product is discharged after cooling down to below 40° C. to obtain Compound A-1. The viscosity of the resulting reaction product is 200 Centipoise, pH=9. The decomposition temperature of the compound A-1 is in a range of 45-70° C. (decomposing very slowly from 45° C., peak decomposition temperature is 57-62° C.). The content of alkali metal ion and alkaline earth metal ion of the compound A-1 as determined by the atomic absorption spectrophotometer (Seiko Instruments, Inc.; SAS/727) is below the detection limit. According to the gas chromatographic analysis, the mole ratio of monopropanol amine to dipropanol amine is 1:0.06. The compound A-1 contains about 75 wt % of salts of both monopropanol amine and dipropanol amine. It also contains a portion of water. Additionally, the compound A-1 contains about 55 wt % of monopropanol amine and dipropanol amine (after heating the compound A-1 to release carbon dioxide).

The compound A-1 is a transparent or clear liquid which is relatively stable at room temperature or under ambient condition and is suitable for using as polyurethane foaming agent, and the comparison of its basic characteristics with HFC-245fa, LBA and pentafluorobutane is listed in the following table:

| | Compound A-1 | HFC245fa | pentafluorobutane | LBA |
|---|---|---|---|---|
| ODP | 0 | 0 | 0 | 0 |
| GWP | 1 | 1030.01 | 793.98 | 5.00 |
| Boiling point (° C.) | Begins to decompose slowly from 45° C. | 15.3 | 40.2 | 19.3 |

It is observed from above table that, compound A-1 has the GWP (Global Warming Potential) of 1 and relatively high decomposition temperature, and can overcome many shortcomings of some physical foaming agents with low boiling point (below 20° C.) such as HFC-245fa, LBA or pentafluorobutane, such as GWP far larger than 1, relatively low boiling point and volatile property. The compound A-1 of the present invention has the GWP of 1, has a higher boiling point and thus not easy to volatilize, and its ODP (ozone depletion potential value) is 0, so it does not destroy the atmospheric ozone layer; as well as the transportation and storage of the compound A-1 is convenient due to its lower volatility.

Example A-2

1.4 tons of ammonium carbamate, 0.7 ton of ethylene glycol and 0.9 ton of water are charged into a stainless steel reactor equiped with a cooling jacket, agitation is started to make ammonium carbamate be dissolved slowly (not always dissolve completly). The reaction system is treated and protected by nitrogen gas and then heated up, and the temperature is controlled to a range of 45-70° C. and the pressure is controlled to no more than 0.6 MPa. Then, 1.3 tons (in total) of ethylene oxide (molecular weight 44.05) is incorporated slowly and batchwise into the reaction system, and thereafter the reaction system is stirred for 5 hour under the temperature of 45-70° C. and the pressure below 0.6 MPa. The temperature of the reaction system is then reduced to 50° C., and the unnecessary water and the unreacted ethylene oxide are removed from the reaction system under reduced pressure of 600 mmHg (for example to achieve the water content of below 30 wt %). After cooling down to 40° C. or less, the product was released to obtain Compound A-2. Its viscosity is about 250, pH=9. The decomposition temperature of the compound A-2 is in a range of 45-70° C.

Example A-3 (Preferably in Present Invention)

1 kg of ammonium carbamate and 1 kg of water are charged to a transparent quartz glass reactor, agitation is started to dissolve ammonium carbamate (allowing the presence of some insoluble ammonium carbamate), and the reactor is purged with nitrogen gas. Then, 2 kg of propylene oxide is added to the reactor. Agitation is started, the reaction system is heated up slowly, and the reaction is carried out at the controlled temperature of 50-60° C. and controlled pressure of no more than 0.6 MPa. When the reaction goes up to about 2 hours, a fantastic phenomen bursts into view: the turbid and opaque mixture instantly become to a transparent or clear solution; and the reaction is allowed to proceed for 8 hours. The temperature of the reaction system is reduced to 50° C., and the unnecessary water and the unreacted propylene oxide are removed from the reaction system under a vacuum degree below 600 mmHg. After cooling to below 40° C., the resulting product is discharged. The reaction time is sufficient to ensure the reaction is conducted according to the mole ratio of the reactants. Compound A-3 is obtained. Its viscosity is 200 centipoise, pH=9.1, and its decomposition temperature is in a range of 45-70° C. Liquid chromatography analysis and gas chromatography analysis show that compound A-3 is a mixture comprises more than one of alkanolamines. The water content is 21.5 wt %. The infrared spectrum is shown in FIG. 1.

Example A-4 (Preferably in Present Invention)

Figure 2:
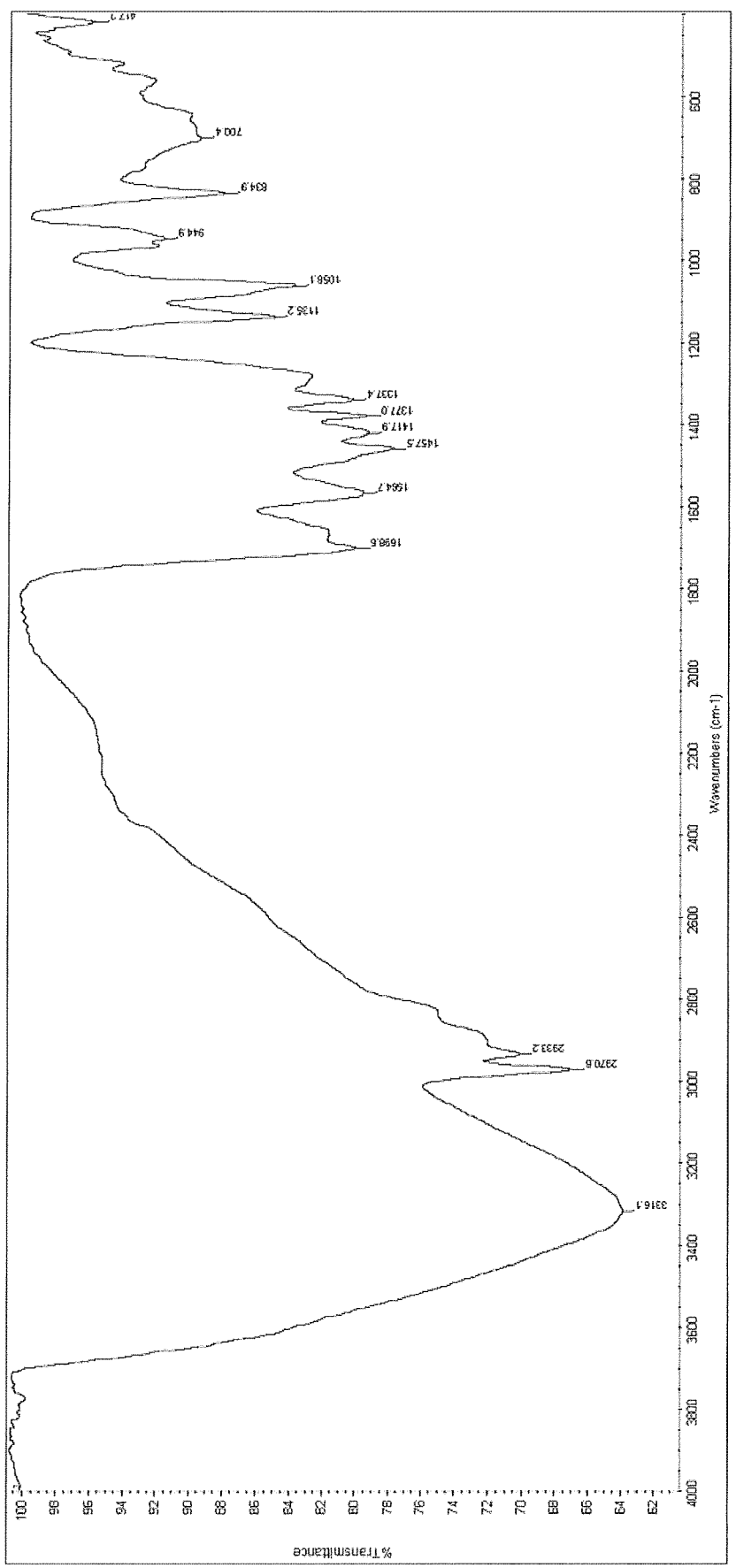
FIG. 2 is an infrared spectrogram of the product of example A-4.

1 ton of ammonium carbamate and 1 ton of water are charged to a stainless steel autoclave equiped with a cooling water jacket, agitation is started to dissolve ammonium carbamate (allowing the presence of some insoluble ammonium carbamate), and the reactor is purged with nitrogen gas. Then, 2.2 tons of propylene oxide are added batchwise to the reactor, the reactor is closed and agitation is started, and the reaction system is heated up slowly under constant stirring. The reaction is allowed to proceed for 10 hours at the controlled temperature of 45-70° C. and controlled pressure of no more than 0.6 MPa. Then the temperature of the reaction system is reduced to 50° C., and the unnecessary water is removed from the reaction system under a vacuum degree below 600 mmHg. After cooling to below 40° C., the resulting product is discharged to obtain compounds A-4. Its viscosity is 200 centipoise, pH=9, and its decomposition temperature is in a range of 45-70° C. It is indicated from the liquid chromatography analysis and the gas chromatographic analysis that compound A-4 is a mixture comprises more than one of alkanolamines. Its infrared spectrogram is showed in FIG. 2.

Example A-5 (Preferably in Present Invention)

7 kg of ammonium carbonate, 7 kg of ammonium carbamate and 12 kg of water are charged to a reactor, agitation is started to dissolve ammonium carbonate and ammonium carbamate (allowing the presence of some insoluble ammonium carbamate and ammonium carbonate), and the reactor is purged with nitrogen gas. 30 kg of propylene oxide is added batchwise to the reactor. The reaction system is heated up slowly with continual agitation, and the reaction is allowed to proceed for 10 hours under the controlled temperature of 45-70° C. and controlled pressure of not more than 0.6 MPa. Then the temperature of the reaction system is reduced to 50° C., and the unnecessary water and unreacted propylene oxide are removed from the system under a vacuum degree below 600 mmHg and a temperature below 50° C. After cooling to below 40° C., the vacuum is released, the the resulting product is discharged, so as to obtain compound A-5. Its viscosity is about 200 centipoise, pH=9, and its decomposition temperature is in a range of 45-70° C.

Example A-6 (Preferably in Present Invention)

16 kg of monoethanolamine carbamate and 10 kg of water are charged to a reactor, the reactor is purged with nitrogen gas, and agitation is started to dissolve the monoethanolamine carbamate. 12 kg of propylene oxide is added batchwise to the reactor, agitation is started, the pressure is controlled to no more than 0.6 MPa, and the reaction system is heated up slowly with continual agitation. The temperature of the reaction system is then increased to 70° C. and the system is allowed to react for 5 hours at this temperature. The temperature of the reaction system is then reduced to below 50° C., and the unnecessary water and unreacted propylene oxide are removed from the system under a vacuum degree below 600 mmHg. After cooling to below 40° C., the vacuum is released, and the the resulting product is discharged, so as to obtain compound A-6. Its viscosity is 230 centipoise, pH=9, and its decomposition temperature is in a range of 45-70° C.

Example A-7

20 kg of diethylene triamine carbamate and 10 kg of water are charged to a reactor, the reactor is purged with nitrogen gas, and agitation is started to dissolve the diethylene triamine carbamate. 15 kg of propylene oxide is added batchwise to the reactor under agitation while the pressure is controlled to not more than 0.6 MPa and the temperature is controlled in a range of 45-70° C. After the completion of the addition of propylene oxide, the reaction system is allowed to react for 5 hours at this temperature; the temperature of the reaction system is then reduced to below 50° C., and the unnecessary water and unreacted propylene oxide are removed from the reaction system under a vacuum degree below 600 mmHg. After cooling to below 40° C., the vacuum is released, and the resulting product is discharged, so as to obtain compound A-7. Its viscosity is about 350 centipoise, pH=9, and its decomposition temperature is in a range of 45-70° C.

Example A-8

1 ton of ammonium carbamate (molecular weight 78.07) and 1 ton of water are charged to a reactor, agitation is started to dissolve ammonium carbamate (allowing the presence of some insoluble ammonium carbamate), and the reactor is purged with nitrogen gas. 2.8 tons of epichlorohydrin (i.e., 3-chloro-1-epoxypropane, molecular weight 92.52, boiling point 117.9° C.) are added to the reactor and agitation is started. The reaction system is heated up slowly with continual agitation, and allowed to react for 10 hours at the controlled temperature of 45-70° C. and controlled pressure of no more than 0.6 MPa. Then the temperature of the reaction system is reduced to 50° C., and the unnecessary water and unreacted epichlorohydrin are removed from the reaction system under a vacuum degree below 600 mmHg. After cooling to below 40° C., the resulting product is discharged, so as to obtain compound A-8. Its viscosity is 450 centipoise, pH=9, and its decomposition temperature is in a range of 45-70° C.

Example A-9

0.65 ton of ammonium carbonate, 0.65 ton of ammonium carbamate and 1.2 tons of water are charged to a reactor, agitation is started to dissolve ammonium carbonate and ammonium carbamate (allowing the presence of some insoluble ammonium carbamate and ammonium carbonate), and the reactor is purged with nitrogen gas. 3.6 tons of styrene oxide (molecular weight 120.15) is added to the reactor. The reaction system is heated up slowly with continual agitation, and allowed to react for 10 hours at the controlled temperature 45-70° C. and controlled pressure of no more than 0.6 MPa. Then the temperature of the reaction system is reduced to 50° C., and the unnecessary water is removed from the reaction system under a vacuum degree below 600 mmHg and a temperature below 50° C. After cooling to below 40° C., the vacuum is released, the resulting product is discharged, so as to obtain compound A-9. Its viscosity is about 460 centipoise, pH=9, and its decomposition temperature is in a range of 45-70° C.

Example A-10

1 kg of hydrazinium carbamate and 0.9 kg of water are charged to a transparent quartz glass reactor, agitation is started to dissolve hydrazinium carbamate (allowing the presence of some insoluble hydrazinium carbamate) for 30 minutes, and the reactor is purged with nitrogen gas. 1.8 kg of propylene oxide is added to the reactor in batch. Agitation is started. The reaction system is heated up slowly, and allowed to react at the controlled temperature of 50-70° C. and controlled pressure of no more than 0.6 MPa. When the reaction goes up to about 2 hours, a fantastic phenomen bursts into view: the turbid and opaque mixture instantly become to a transparent or clear solution. The mixture is allowed to further react for 5 hours. The temperature of the reaction system is then reduced to 50° C., and a part of water and the unreacted propylene oxide are removed from the reaction system under a vacuum degree below 600 mmHg. After cooling to below 40° C., the resulting product is discharged. The reaction time is sufficient to ensure the reaction is conducted according to the mole ratio of the reactants, so as to obtain compound A-10. Its pH is 8.9, and its decomposition temperature is in a range of 45-70° C.

B) Preparing the Compounds of the General Formula (I) Containing $CO_3^{2-}$ Anion Example B-1

14 kg of a ammonium carbonate (molecular weight 96), 6 kg of ethylene glycol and 8 kg of water are charged to a reactor, agitation is started to dissolve ammonium carbonate (allowing the presence of some insoluble ammonium carbonate), and the reactor is purged with nitrogen gas. 20 kg of propylene oxide is added to the reactor, and agitation is started. The reaction system is heated up slowly with continual agitation, and allowed to react for 12 hours at the controlled temperature of less than 70° C. and conrolled pressure of no more than 0.6 MPa. After completion of the reaction, the temperature of the reaction system is reduced to 50° C. slowly, and the unnecessary water and unreacted propylene oxide are removed from the reaction system under a vacuum degree below 600 mmHg. After cooling to below 40° C., the vacuum is released, and the the resulting product is discharged, so as to obtain compounds B-1. Its viscosity is about 300 centipoise, pH=9, and the decomposition temperature is in a range of 45-70° C. It is indicated from the liquid chromatography analysis and the gas chromatographic analysis that the compounds B-1 is a mixture comprises more than one of alkanolamines. The content of alkali metal ion and alkaline earth metal ion of the compound B-1 as determined by the atomic absorption spectrophotometer (Seiko Instruments, Inc.; SAS/727) is below the detection limit. According to the gas chromatographic analysis, the mole ratio of monopropanol amine to dipropanol amine is 1:0.22. The compound B-1 contains about 78 wt % of the salts of both monopropanol amine and dipropanol amine. The compound B-1 contains about 56 wt % of monopropanol amine and dipropanol amine.

Example B-2

1.4 tons of ammonium carbonate and 1 ton of water are charged to a stainless steel autoclave equiped with a cooling water jacket, agitation is started to dissolve ammonium carbonate (allowing the presence of some insoluble ammonium carbonate), the reactor is purged with nitrogen gas, and then the autoclave is sealed. Under constant stirring, the temperature of the reaction system is controled at 45-70° C. and its pressure is controled at no more than 0.6 MPa, and 1.3 tons of ethylene oxide are added batchwise to the reactor and the reaction is then allowed to be conducted under the controlled temperature for 4 hours. Then the temperature of the reaction system is reduced to 50° C., and the unnecessary water and unreacted ethylene oxide are removed from the reaction system under a vacuum degree below 600mHg. After cooling to below 40° C., the vacuum is released, and the resulting product is discharged so as to obtain compounds B-2. Its viscosity is 300 centipoise, pH=9.1, and its decomposition temperature is in a range of 45-70° C. It is indicated from the liquid chromatography analysis and the gas chromatographic analysis that compound B-2 is a mixture comprises more than one of alkanolamines.

Example B-3

20 kg of ammonium carbonate and 18 kg of water are charged to a transparent quartz glass reactor, agitation is started to dissolve ammonium carbonate (allowing the presence of some insoluble ammonium carbonate), and the reactor is purged with nitrogen gas. With continual agitation, the temperature of the reaction system is controled at 45-70° C. and its pressure is controled at no more than 0.6 MPa, and 45 kg of propylene oxide is added to the reactor and the reaction is conducted at the controlled temperature. When the reaction goes up to about 2 hours, a fantastic phenomen bursts into view: the turbid and opaque mixture instantly become to a transparent or clear solution. The reaction is allowed to be further conducted for 8 hours. The temperature of the reaction system is then reduced to 50° C., and the unnecessary water and the unreacted propylene oxide are removed from the reaction system under a vacuum degree below 600 mmHg. After cooling to below 40° C., the vacuum is released, and the resulting product is discharged, so as to obtain compound B-3. Its viscosity is about 250 centipoise, pH=9.1, and its decomposition temperature is in a range of 45-70° C.

Example B-4

20 kg of aqueous ammonia (25 wt % concentration) is added to a reactor, the reactor is purged with nitrogen gas, and agitation is started. 16 kg of ethylene oxide is added batchwise to the reaction system while the pressure of the system is controlled to not more than 0.6 MPa and its temperature is not more than 120° C. After the addition, the reaction is performed under the controlled temperature for 1 hour. After the reaction is completed, the temperature is lowered to room temperature, and then unnecessary water and unreacted ethylene oxide are distilled off under reduced pressure. 4 kg of carbon dioxide (molecular weight 44) is incorporated until the pH is about 8 and the temperature is controlled below 80° C. The reaction system is cooled down to room temperature after the reaction is completed. Compounds B-4 is obtained. Its viscosity is about 400 centipoise, and its decomposition temperature is in a range of 45-75° C.

Example B-5

20 kg of aqueous ammonia (25 wt % concentration) and 5 kg of ethylene glycol are added to a reactor, the reactor is purged with nitrogen gas, and agitation is started. Then 20 kg of propylene oxide is added batchwise to the reaction system while the pressure of the system is controlled to not more than 0.6 MPa and its temperature is not more than 120° C. After addition, the system is allowed to react under the controlled temperature for 2 hours. After the reaction is completed, the temperature of the reaction system is lowered to ambient temperature, and the unnecessary water and unreacted propylene oxide are distilled off from the system at reduced pressure. 5 kg of carbon dioxide (molecular weight 44) is incorporated into the reactor untill the pH value of the system is about 8 and the temperature is controlled below 80° C. The reaction system is cooled down to room temperature after the reaction is completed. Compounds B-5 is obtained. Its viscosity is about 450 centipoise, and its decomposition temperature is in a range of 45-75° C.

Example B-6

Figure 3:
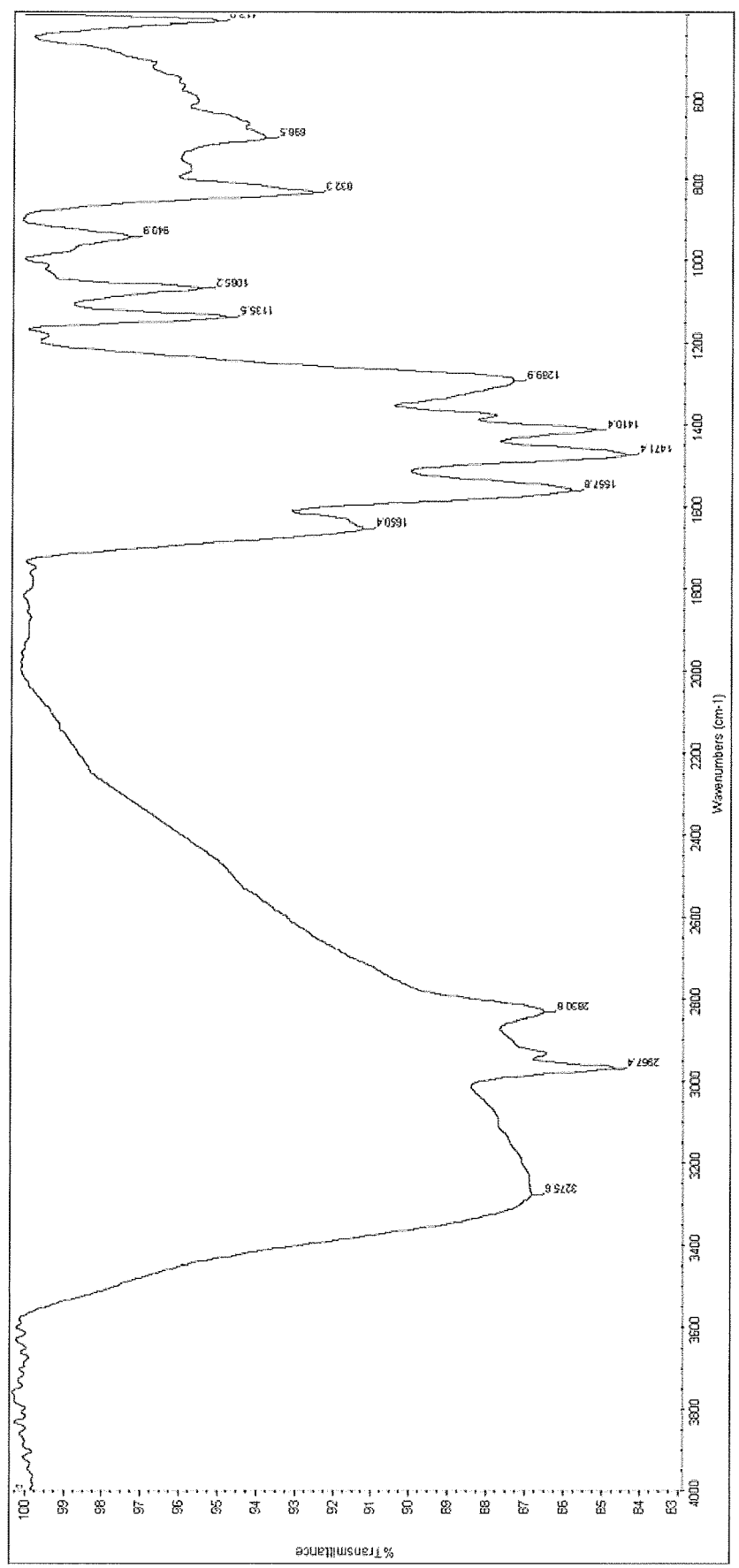
FIG. 3 is an infrared spectrogram of the product of example B-6.

10 kg of diethylenetriamine (molecular weight 103.17) and 15 kg of water are added to a reactor, the reactor is pureged with nitrogen gas, and agitation is started. 15 kg of propylene oxide is added batchwise to the reaction system while the pressure of the system is controlled to not more than 0.6 MPa and its temperature is not more than 120° C. After addition, the system is allowed to react under the controlled temperature for 1 hour. After the reaction is finished, the temperature of the reaction system is lowered to ambient temperature; and the unnecessary water and the unreacted propylene oxide are distilled off from the system at reduced pressure. 6 kg of carbon dioxide is incorporated into the reactor untill the pH value of the system is about 8 and the temperature is controlled below 80° C. The reaction system is cooled down to room temperature after the reaction is completed. Compounds B-6 is obtained. Its viscosity is about 500 centipoise, and its decomposition temperature is in a range of 45-70° C. The infrared spectrogram of the compounds is showed in FIG. 3.

Example B-7

10 kg of ethylene diamine (molecular weight 60.12) and 15 kg of water are added to a reactor, the reactor is purged with nitrogen gas, and agitation is started. 10 kg of ethylene oxide (molecular weight 44.05) is added batchwise to the reaction system while the pressure of the system is controlled to not more than 0.6 MPa and its temperature is not more than 120° C. After addition, the system is allowed to react under the controlled temperature for 1 hour. After the reaction is completed, the temperature of the reaction system is lowered to ambient temperature, and the unnecessary water and unreacted ethylene oxide are distilled off from the system at reduced pressure. 5 kg of carbon dioxide is incorporated into the reactor untill the pH value of the system is about 8 and the temperature is controlled below 80° C. The reaction system is cooled down to room temperature after the reaction is completed. Compounds B-7 is obtained. Its viscosity is about 500 centipoise, and its decomposition temperature is in a range of 45-70° C.

Example B-8

6 kg of ethylene diamine (molecular weight 60.12) and 3.4 kg of liquid ammonia are charged into a special pressure resistant mixing tank and mixed well. The resulting mixture is incorporated in a certain controlled flow rate by a pipeline into a mixing reactor, and slowly mixed with 9 kg of carbon dioxide gas while the the pressure therein is controlled at 0.6 MPa and the temperature therein is controlled below 60° C. After the reaction is completed, the temperature of the reaction mixture is lowered to ambient temperature. The resulting product and 10 kg of water are charged into an autoclave and the product is allowed to dissolve slowly (allowing the presence of some insoluble). The reactor is purged with nitrogen gas, 35 kg of propylene oxide is added batchwise to the autoclave while the pressure therein is controlled to not more than 0.6 MPa and the temperature is controlled to not more than 70° C., and once the addition is finished, the resultant mixture is allowed to react for 5 hours under the controlled temperature. After the reaction is finished, the temperature of the reaction mixture is lowered to ambient temperature. Then a part of water and unreacted propylene oxide are distilled off under reduced pressure, so as to obtain compounds B-8. Its pH=9.1, and its decomposition temperature is in a range of 45-70° C.

Example B-9

6 kg of diethylenetriamine (molecular weight 103.17) and 3 kg of liquid ammonia are charged into a special pressure resistant mixing tank and mixed well. The resulting mixture is incorporated in a certain controlled flow rate by a pipeline into a mixing reactor, and slowly mixed with 7.6 kg of carbon dioxide gas while the the pressure therein is controlled at 0.6 MPa and the temperature therein is controlled below 60° C. After the reaction is completed, the temperature of the reaction mixture is lowered to ambient temperature, and the resulting product and 10 kg of water are charged into an autoclave and the product is allowed to dissolve slowly (allowing the presence of some insoluble). The reactor is purged with nitrogen gas. 22 kg of ethylene oxide is added batchwise to the autoclave while the pressure therein is controlled to not more than 0.6 MPa and the temperature is controlled to not more than 70° C., and once the addition is finished, the resultant mixture is allowed to react for 5 hours under the controlled temperature. After the reaction is completed, the temperature of the reaction mixture is lowered to ambient temperature. A part of water and unreacted ethylene oxide are removed by distillation under reduced pressure, so as to obtain compounds B-9. Its pH is 8.8, and its decomposition temperature is in a range of 45-70° C.

Example B-10

6 kg of diethylenetriamine (molecular weight 103.17) and 3 kg of liquid ammonia are charged into a special pressure resistant mixing tank and mixed well. The resulting mixture is incorporated in a certain controlled flow rate by a pipeline into a mixing reactor, and slowly mixed with 7.6 kg of carbon dioxide gas while the the pressure therein is controlled at 0.6 MPa and the temperature therein is controlled below 60° C. After the reaction is completed, the temperature of the reaction mixture is lowered to ambient temperature, and the resulting product and 10 kg of water are charged into an autoclave and the product is allowed to dissolve slowly (allowing the presence of some insoluble). The reactor is purged with nitrogen gas. 9 kg of ethylene oxide and 14 kg of propylene oxide is added batchwise to the autoclave while the pressure therein is controlled to not more than 0.6 MPa and the temperature is controlled to not more than 70° C., and once the addition is finished, the resultant mixture is allowed to react for 5 hours under the controlled temperature. After the reaction is completed, the temperature of the reaction mixture is lowered to ambient temperature, and a part of water and the unreacted ethylene oxide and propylene oxide are distilled off under reduced pressure, so as to obtain compounds B-10. Its pH is 9.0, and its decomposition temperature is in a range of 45-70° C.

Example B-11

6 kg of ethylene diamine (molecular weight 60.12), 3 kg of methylamine (molecular weight 31.10) and 1.7 kg of liquid ammonia are charged into a special pressure resistant mixing tank and mixed well. The resulting mixture is incorporated in a certain controlled flow rate by a pipeline into a mixing reactor, and slowly mixed with 8.5 kg of carbon dioxide gas while the the pressure therein is controlled at 0.6 MPa and the temperature therein is controlled below 60° C. After the reaction is completed, the temperature of the reaction mixture is lowered to ambient temperature, and the resulting product and 10 kg of water are charged into an autoclave and the product is allowed to dissolve slowly (allowing the presence of some insoluble). The reactor is purged with nitrogen gas, and 31 kg of propylene oxide is added batchwise to the autoclave while the pressure therein is controlled to not more than 0.6 MPa and the temperature is controlled to not more than 70° C., and once the addition is finished, the resultant mixture is allowed to react for 5 hours under the controlled temperature. After the reaction is completed, the temperature of the reaction mixture is lowered to ambient temperature, and a part of water and unreacted propylene oxide are removed by distillation under reduced pressure, so as to obtain compounds B-11. Its pH is 9.0, and its decomposition temperature is in a range of 45-70° C.

Example B-12

0.9 kg of hydrazinium carbonate and 0.8 kg of water are charged to a transparent quartz glass reactor, agitation is started to dissolve hydrazinium carbonate (allowing the presence of some insoluble hydrazinium carbonate) for 30 minutes, and the reactor is purged with nitrogen gas. 1.8 kg of propylene oxide is added batchwise to the reactor; and then agitation is started. The reaction system is heated up slowly under constant stirring, and allowed to react at the controlled temperature of 50-70° C. and controlled pressure of not more than 0.6 MPa. When the reaction goes up to about 2 hours, a fantastic phenomen bursts into view: the turbid and opaque mixture instantly become to a transparent or clear solution. The mixture is allowed to further react for 5 hours. Then, the temperature of the reaction system is reduced to 50° C., and a part of water and the unreacted propylene oxide are removed from the reaction mixture under a vacuum degree below 600 mmHg. After cooling to below 40° C., the resulting product is discharged. The reaction time is sufficient to ensure the reaction is performed according to the mole ratio of the reactants, so as to obtain compounds B-12. Its pH is 8.9, and its decomposition temperature is in a range of 45-70° C.

Example B-13

0.9 kg of hydrazinium carbonate and 0.8 kg of water are charged to a transparent quartz glass reactor, agitation is started to dissolve hydrazinium carbonate (allowing the presence of some insoluble hydrazinium carbonate), and the reactor is purged with nitrogen gas. 1.3 kg of ethylene oxide is added batchwise to the reactor; and then agitation is started. The reaction system is heated up slowly under constant stirring, and the reaction is performed at the controlled temperature of 50-70° C. and controlled pressure of not more than 0.6 MPa. When the reaction goes up to about 2 hours, a fantastic phenomen bursts into view: the turbid and opaque mixture instantly become to a transparent or clear solution. The mixture is allowed to further react for 5 hours. Then, the temperature of the reaction system is reduced to 50° C., and a part of water and the unreacted ethylene oxide are removed from the reaction mixture under a vacuum degree of 600mHg. After cooling to below 40° C., the resulting product is discharged. The reaction time is sufficient to ensure the reaction is performed according to the mole ratio of the reactants. Compounds B-13 is obtained. Its pH=8.8, and its decomposition temperature is in a range of 45-70° C.

C) Preparing the Compounds of the General Formula (I) Containing Formate ($HCOO^-$)

Example C-1

15 kg of ammonium formate, 1 kg of methylamine catalyst, 10 kg of water and 5 kg of ethylene glycol are added to a reactor, the reactor is purged with nitrogen gas, and agitation is started. 12 kg of ethylene oxide is added batchwise to the reactor while the pressure is controlled to not more than 0.5 MPa and the temperature is not more than 120° C. The mixture is allowed to react for 5 hours. After the reaction is completed, the temperature of the reaction mixture is lowered. The unnecessary water and unreacted ethylene oxide are removed from the mixture under reduced pressure while the vacuum degree therein is controlled to below 600 mmHg and the temperature therein is controlled to below 100° C. The vacuum is released, and the temperature of the reaction mixture is lowered to below 50° C. Finally, the resulting product is discharged, so as to obtain compounds C-1. Its viscosity is about 200 centipoise, pH=8.5, and its decomposition temperature is higher than 100° C.

Example C-2

The example C-1 is repeated except that 15 kg of propylene oxide is used to replace 12 kg of ethylene oxide, and propylene oxide is added into the reactor in a manner of one shot but not in a manner of batchwise. Compounds C-2 is obtained. Its viscosity is about 350 centipoise, pH=8.6, and its decomposition temperature is higher than 100° C.

Example C-3

10 kg of methyl formate, 10 kg of ethyl formate, 13 kg of aqueous ammonia (25 wt % concentration), and 35 kg of diethanolamine are added to a reactor. Agitation is started, and then the reaction mixture is heated up slowly while the pressure of the reactor is controlled to not more than 0.5 MPa. The mixture is allowed to react for 15 hours while the temperature of the reaction mixture is maintained at 100° C. After the reaction is finished, the temperature of the reaction mixture is lowered. The vacuum degree inside the reactor is controlled to below 600 mmHg and the temperature is controlled to below 100° C., such that methanol and ethanol are removed from the mixture under reduced pressure. The vacuum is released, and the temperature of the reaction mixture is lowered to 50° C. or less. Finally, the resulting product is discharged, so as to obtain compound C-3. Its viscosity is about 400 centipoise, pH=9, and its decomposition temperature is higher than 100° C.

The above compounds C-1, C-2 or C-3 immediately releases carbon dioxide gas upon contacting with isocyanate, and also releases a small amount of carbon monoxide gas, thereby overcoming the drawbacks of general physical foaming agents such as methyl formate.

Example C-4 (not Belonging to the Compounds of General Formula (I))

24 kg of aqueous ammonia (concentration 25 wt %) is added to a reactor, and 20 kg of formic acid (concentration 85 wt %) is added dropwise slowly to the aqueous ammonia under continual agitation and the temperature of 100° C. or less. After the addition is finished, the reaction mixture is allowed to react at such temperature for 1 hour. Then the unnecessary water is removed from the mixture while the vacuum degree is controlled to below 600 mmHg and the temperature therein is controlled to below 100° C., so as to obtain compounds C-4. Its viscosity is about 150 centipoise, pH=9.5, and its decomposition temperature is higher than 100° C.

Example C-5 (not Belonging to the Compounds of General Formula (I))

23 kg of aqueous ammonia (concentration 25 wt %) and 1.5 kg of dimethylamine are added to a reactor; 20 kg of formic acid (concentration 85 wt %) is added dropwise slowly to the reactor with continual agitation, while the temperature of the reaction mixture is controlled to below 100° C. After the addition is completed, the reaction mixture is allowed to react at such temperature for 1 hour. The unnecessary water is removed from the mixture while the vacuum degree is controlled to below 600 mmHg and the temperature is controlled to below 100° C. The vacuum is released, and the temperature of the mixture is lowered to below 50° C. The product is discharged, to obtain compound C-5. Its viscosity is about 150 centipoise, pH=9.2, and its decomposition temperature is higher than 100° C.

Example C-6 (not Belonging to the Compounds of the General Formula (I))

23 kg of aqueous ammonia (concentration 25 wt %) and 1.5 kg of methylamine are added to a reactor. 20 kg of formic acid (concentration 85 wt %) is added dropwise slowly to the reactor with continual agitation, while the temperature of the reaction mixture is controlled to below 100° C. After the addition is ended, the reaction mixture is allowed to react at such temperature for 1 hour. The unnecessary water is removed from the mixture (for example, the water content can be lowered to about 10 wt %) while the vacuum degree is controlled to below 600 mmHg and the temperature is controlled to below 100° C. The vacuum is released, and the temperature of the mixture is lowered to below 50° C. The product is discharged, thereby obtaining compound C-6. It does not crystallize, which may be due to the fact that the methylamine added can disturb its crystallization. Its viscosity is about 150 centipoise, pH=9, and its decomposition temperature is higher than 100° C.

The above compound C-4, C-5 or C-6 immediately releases carbon dioxide gas upon contacting with isocyanate, and also releases a small amount of carbon monoxide gas, so they can overcome the drawbacks of general physical foaming agents.

Although the compounds C-1 to C-6 do not decompose at a temperture even higher than 110° C., the inventors discover by experiments that these compounds can be easily decomposed and release $CO_2$ gas during the polyurethane foaming process. The reason may be that upon contacting with isocyanate compound, the compounds first react with the NCO group to produce an unstable carbonic anhydride.

D) Preparing the Compounds of the General Formula (I) Containing Bicarbonate Radical (HO—COO$^-$)

Example D-1

10 kg of ammonium bicarbonate (molecular weight 79.06), 9.0 kg of water and 1 kg ethylene diamine are charged to a transparent quartz glass reactor, agitation is started to dissolve ammonium bicarbonate (allowing the presence of some insoluble ammonium bicarbonate), the reactor is purged with nitrogen gas, and then the reactor is sealed. 20 kg of propylene oxide is added batchwise to the reactor with continual agitation while the temperature of the reaction system is controlled to a range of 45-65° C. and its pressure is controlled to not more than 0.6 MPa. The resultant reaction mixture is allowed to react for 10 hours under the controlled temperature. Then, the temperature of the reaction system is reduced to 50° C., and the unnecessary water and unreacted propylene oxide are removed from the reaction mixture under a vacuum degree below 600 mmHg. After cooling to below 40° C., the vacuum is released, and the resulting product is discharged. Compounds D-1 is obtained. Its viscosity is about 250 centipoise, pH=8, and its decomposition temperature is in a range of 36-42° C.

The inventors discover unexpectedly that, when the compound D-1 is mixed with polyether polyol and/or polyester polyol, for example to formulate foaming composition ("white material"), the decomposition temperature of compound D-1 dissolved in the white material can be increased to 45-65° C., which makes the compound D-1 have appropriate decomposition temperature, and hence, is suitable to be used in polyurethane foaming.

E) Preparing the Compounds of the General Formula (I) Containing Monohydrocarbyl Carbonate ($R^bO$—$COO^-$) anion Example E-1

10 kg of ammonium methyl carbonate (molecular weight 93), 9.0 kg of water and 1 kg ethylene diamine are charged to a transparent quartz glass reactor, agitation is started to dissolve ammonium salt (allowing the presence of some insoluble ammonium salt), the reactor is purged with nitrogen gas, and then the reactor is sealed. 20 kg of propylene oxide is added batchwise to the reactor with continual agitation while the temperature of the reaction system is controlled to a range of 45-65° C. and its pressure is controled to not more than 0.6 MPa. After the addition, the resultant reaction mixture is allowed to react for 10 hours with the temperature being controlled. Then the temperature of the reaction mixture is reduced to 50° C., and the unnecessary water and unreacted propylene oxide are removed from the reaction mixture under a vacuum level below 600 mmHg. After cooling to below 40° C., the vacuum is released, and the resulting product is discharged. Compounds E-1 is obtained. Its viscosity is about 350 centipoise, pH=8, and its decomposition temperature is in a range of 42-60° C.

F) Preparing the Compounds of the General Formula (I) Containing $^-OOC$—$N(R^1)$—$R^a$—$N(R^2)$—$COO^-$ or $R^{a'}(—N(R^1)—COO^-)_3$ anion Example F-1

10 kg of $NH_4OOC$—NH— $(CH_2)_5$—NH—$COONH_4$ (molecular weight 182) and 9.0 kg of water are charged to a transparent quartz glass reactor, agitation is started to dissolve ammonium salt (allowing the presence of some insoluble ammonium salt), the reactor is purged with nitrogen gas, and then the reactor is sealed. 20 kg of propylene oxide is added batchwise to the reactor with continual agitation while the temperature of the reaction system is controled to a range of 45-55° C. and its pressure is controled to not more than 0.6 MPa. The resultant reaction mixture is allowed to react for 10 hours with the temperature being controlled. Then the temperature of the reaction mixture is reduced to 50° C., and the unnecessary water and unreacted propylene oxide are removed from the reaction mixture under a vacuum level below 600 mmHg. After cooling to below 40° C., the vacuum is released, and the resulting product is discharged. Compounds F-1 is obtained. Its viscosity is about 600 centipoise, pH=9, and its decomposition temperature is in a range of 45-70° C.

Example F-2

12 kg of benzene-1,3,5-tri (ammonium carbamate) (molecular weight 306) having following formula:

and 9.0 kg of water are charged to a transparent quartz glass reactor; agitation is started to dissolve ammonium salt (allowing the presence of some insoluble ammonium salt), the reactor is purged with nitrogen gas, and then the reactor is sealed. 20 kg of propylene oxide is added batchwise to the reactor with continual agitation while the temperature of the reaction system is controled to a range of 45-60° C. and its pressure is controled to not more than 0.6 MPa. The resultant reaction mixture is allowed to react for 10 hours with the temperature being controlled. Then the temperature of the reaction system is reduced to 50° C., and the unnecessary water and unreacted propylene oxide are removed from the reaction mixture under a vacuum level below 600mHg. After cooling to below 40° C., the vacuum is released, and the resulting product is discharged. Compounds F-2 is obtained. Its viscosity is about 510 centipoise, pH=9.6, and its decomposition temperature is in a range of 45-70° C.

G) Preparing the Compounds of the General Formula (I) Containing Orthoformate Anion Example G-1

15 kg of triethyl orthoformate, 20 kg of diethanolamine and 10 kg of water are added to a reactor; and agitation is started. The reaction mixture is heated up slowly while the pressure of the reaction system is controlled to not more than 0.1 MPa. The mixture is allowed to react for 10 hours while the temperature of the reaction mixture is maintained at 80° C. After the reaction is completed, the temperature of the reaction mixture is lowered to 50° C. The ethanol byproduced is removed from the reaction mixture while the vacuum degree is controlled to not more than 600 mmHg and the temperature is controlled to below 50° C. Then the temperature of the reaction mixture is lowered to below 40° C. The resulting product is discharged to obtain compounds G-1; its viscosity is about 500 centipoise, pH=8.0, and its decomposition temperature is in a range of 45-70° C.

Example G-2

15 kg of trimethyl orthoformate, 2.0 kg of ethylene glycol, 10 kg of water and 6.0 kg of ethylene diamine are added to a reactor; and agitation is started. Then the reaction mixture is heated up slowly while the pressure of the reactio system is controlled to not more than 0.1 MPa. The mixture is allowed to react for 5 hours while the temperature of the reaction mixture is maintained at 70° C., After the reaction is completed, the temperature of the reaction mixture is lowered. The methanol byproduced is removed from the reaction mixture while the vacuum degree is controlled to not more than 600 mmHg and the temperature is controlled to below 50° C. The vacuum is released, the temperature of the reaction mixture is lowered to below 40° C., and the resulting product is discharged to obtain compounds G-2. Its viscosity is about 250 centipoise, pH=8.3, and its decomposition temperature is in a range of 45-70° C.

Example G-3

15 kg of triethyl orthoformate, 13 kg of monoethanolamine and 7.0 kg of water are added to a reactor; and agitation is started. The reaction mixture is heated up slowly with continual agitation, and the mixture is allowed to react for 8 hours while the temperature of the reaction mixture is maintained at 100° C. After the reaction is completed, the temperature of the reaction mixture is lowered. The ethanol byproduced is removed from the mixture under a reduced pressure while the vacuum degree is controlled to not more than 600 mmHg and the temperature tis controlled to below 50° C. The vacuum is released, and the temperature of the reaction mixture is lowered to below 50° C. The resulting product is discharged, so as to obtain compound G-3 wherein two ester groups in triethyl orthoformate have been hydrolyzed. Its viscosity is about 300 centipoise, pH=8.1, and its decomposition temperature is in a range of 45-70° C.

Example G-4

20 kg of ethylene glycol orthoformate, 11 kg of diethanolamine and 10 kg of aqueous ammonia are added to a reactor; and agitation is started. The reaction mixture is heated up slowly with continual agitation, and the mixture is allowed to react for 8 hours while the temperature of the reaction mixture is maintained below 100° C. After the reaction is finished, the temperature of the reaction mixture is lowered. The unnecessary water is removed from the mixture under reduced pressure while the vacuum level is controlled to below 600 mmHg and the temperature is controlled to below 50° C. The vacuum is released, the temperature of the reaction mixture is lowered to below 40° C., and the resulting product is discharged, to obtain compound G-4. Its viscosity is about 500 centipoise, pH=8, and its decomposition temperature is in a range of 45-70° C.

Application Examples

Example 1

8 parts by weight of the compound A-1 as foaming agent prepared by above example A-1, 50 parts by weight of polyether polyol 4110 (BEFAR GROUP CO., LTD, BinZhou, China), 1 part by weight of foam stabilizer DC3201 (Air Products and Chemicals, Inc., America), 12.5 parts by weight of flame retardant TCPP (Jiangsu Yoke Technology Co., Ltd., China), and 2 parts by weight of catalyst A33 (33LV, Air Products and Chemicals, Inc., America) are mixed to obtain a transparent foaming composition, and then 95.5 parts by weight of isocyanate MDI (PM200, WANHUA CHEMISTRY GROUP CO., LTD) is added to the composition, and a polyurethane foam material is obtained by stirring and foaming.

Example 2

8 parts by weight of the compound A-2 as foaming agent prepared by above example A-2, 30 parts by weight of polyether polyol 4110, 20 parts by weight of polyester polyol CF6320 (Jiangsu Fusheng Innovative Material Technologies, Ltd., China) and 1 part by weight of foam stabilizer DC3201, 12.5 parts by weight of flame retardants TCPP, and 2 parts by weight of catalyst A33 are mixed to obtain a transparent foaming composition, and then 95.5 parts by weight of isocyanate MDI (PM200) is added to the composition, thereby obtain a polyurethane foam material by stirring and foaming.

Example 3

20 parts by weight of compound A-3 as foaming agent, 2 parts by weight of foam stabilizer DC3201, 0.5 part by weight of catalyst dibutyltin dilaurate, 0.5 part of weight of catalyst PC-5 (Air Products and Chemicals, Inc., America), 1 part by weight of catalyst PC-8 (Air Products and Chemicals, Inc., America), 1 part by weight of catalyst PT304 (Air Products and Chemicals, Inc., America), 1 part by weight of catalyst A33, 40 parts by weight of flame retardant TCPP, 20 parts by weight of polyether polyol 4110, 10 parts by weight of AKS7004 (AEKYUNG PETROCHEMICAL CO., LTD KOREA), 10 parts by weight of MN500 (Shandong Blue Star DongDa Chemical Co, Ltd., hydroxyl value mgKOH/g: 330-350) and 10 parts by weight of polyester polyol CF6320 (Jiangsu Fusheng Innovative Material Technologies, Ltd., China) are mixed homogeneously to obtain a foaming composition. 50 kg of the resulting composition is mixed with isocyanate MDI (PM200) in a volume ratio of 1:1-1.6 (i.e., the volume ratio of "white material" to MDI) in a high pressure spraying coater, and the resultant mixture is spraying coated to prepare a polyurethane foam material.

Example 4

7 parts by weight of the compound A-4 as foaming agent, 1 part by weight of catalyst PC-41 (Air Products and Chemicals, Inc., America), 0.5 part by weight of catalyst PC-8 (Air Products and Chemicals, Inc., America), 13 parts by weight of cyclopentane and 2 parts by weight of foam stabilizer DC8545 (Air Products and Chemicals, Inc., America) are added to a mixture of 50 parts by weight of polyether polyol 2010 (Jiangsu HaiAn Petrochemical Plant), 25 parts by weight of polyether polyol SA380 (Shandong INOV Polyurethane Incorporated) and 25 parts by weight of polyether polyol SA460 (Shandong INOV Polyurethane Incorporated) and are mixed homogeneously to obtain a transparent foaming composition ("white material"), and then 148.2 parts by weight of isocyanate MDI (PM200) is added to the foaming composition. The resultant mixture is stirred uniformly and is injected into a foaming mould to carry out foaming, so as to obtain a polyurethane foam material with skin.

Figure 4:
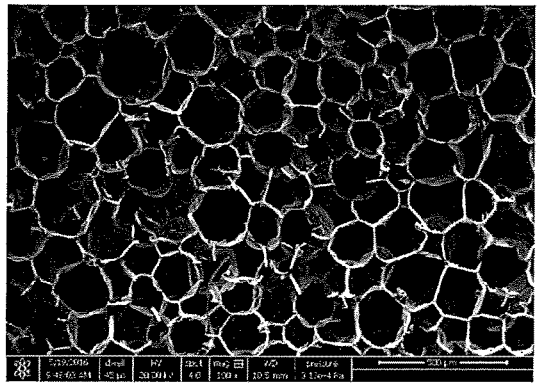
FIG. 4 is a scanning electron microscope (SEM) photograph of the foam of example 4.

Samples are taken from the polyurethane foam, and after slicing with a razor blade, the SEM was used to observe the cells of the resulting pieces by magnifying 100 times. As shown in FIG. 4, the average cell diameter is 205 microns.

Figure 5:
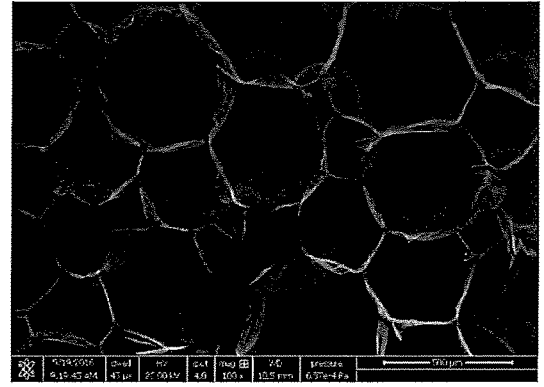
FIG. 5 is a SEM photograph of the comparitive foam 4-1 obtained by repeating the example 4.

As a comparison, example 4 is repeated except that 5 parts by weight of water and 12 parts by weight of cyclopentane (1:2.4 weight ratio) are used as the foaming agent, so as to obtain the comparative foam 4-1; the average diameter of cells is 396 micrometres, as showed in FIG. 5.

Figure 6:
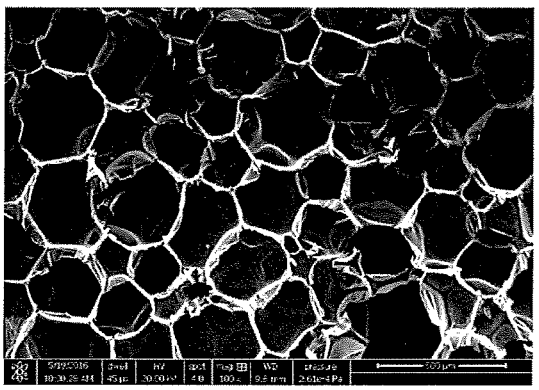
FIG. 6 is a SEM photograph of the reference foam 4-2 obtained by repeating the example 4.
Figure 7:
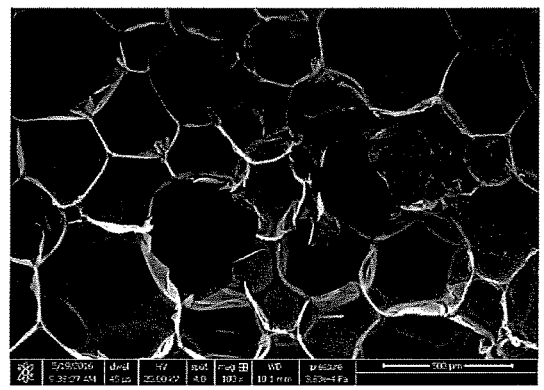
FIG. 7 is a SEM photograph of the comparitive foam 4-3 obtained by repeating the example 4.

Additionally, example 4 is repeated except that the compounds A-4 of the present invention and cyclopentane (1:1.5 weight ratio) are used as the foaming agent, so as to obtain the reference foam 4-2; the average diameter of cells is 306 micrometres, as showed in FIG. 6. As a comparison, example 4 is repeated except that a mixture of water+LBA+cyclopentane (1:1:1 weight ratio) is used as the foaming agent, so as to obtain the comparative foam 4-3; the average diameter of cells is 495 micrometres, as showed in FIG. 7. Additionally, Example 4 is repeated except that the compounds A-4 of the present invention, LBA and cyclopentane (1:1.2:1.3 weight ratio) are used as the foaming agent, so as to obtain the reference foam 4-4; the average diameter of cells is 335 micrometres, as showed in FIG. 8.

Figure 8:
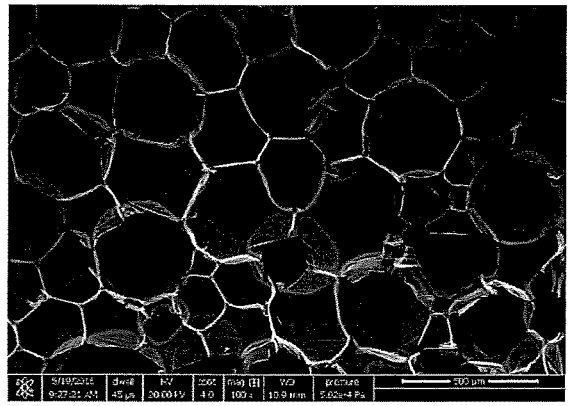
FIG. 8 is a SEM photograph of the reference foam 4-4 obtained by repeating the example 4.

It is observed from FIGS. 4, 6 and 8 that the cells of each foam material appear to be fine, uniform and dense; and the cell numbers per unit area are obviously more. It is observed from FIGS. 5 and 7 that the cell diameter of each foam material appear to be not uniform; and the cell numbers per unit area are obviously less.

Example 5

6 parts by weight of the compound A-5 as foaming agent, 1 part by weight of foam stabilizer DC3201 (Air Products and Chemicals, Inc., America), 30 parts by weight of polyether polyol 4110 (BEFAR GROUP CO., LTD, Bin-Zhou, China), 20 parts by weight of polyester polyol CF6320 (Jiangsu Fusheng Innovative Material Technologies, Ltd., China), and 0.5 part by weight of catalyst PC-41 (Air Products and Chemicals, Inc., America) are mixed to obtain a foaming composition. Then 85 parts by weight of isocyanate MDI (PM200) is added to the composition, thereby obtaining a polyurethane foam material by stirring well and foaming.

Example 6

20 parts by weight of the compound A-6 as foaming agent, 50 parts by weight of polyether polyol 2010 (Jiangsu Haian Petrochemical Plant), 25 parts by weight of polyether polyol SA380 (Shandong INOV Polyurethane Incorporated) and 25 parts by weight of polyether polyol SA460 (Shandong INOV Polyurethane Incorporated), 0.5 part by weight of catalyst PC-41 (Air Products and Chemicals, Inc., America), 0.5 part by weight of catalyst PC-8 (Air Products and Chemicals, Inc., America) are mixed homogeneously to obtain a transparent foaming composition, and then 175 parts by weight of isocyanate MDI (PM200) is added to the foaming composition. Then, the resultant mixture is stirred uniformly to carry out foaming, so as to obtain a polyurethane foam material.

Example 7

4 parts by weight of the compound A-7 as foaming agent, 10 parts by weight of HFC-365mfc, 11 parts by weight of polyether polyol 4110 (BEFAR GROUP CO., LTD, Bin-Zhou, China), 39 parts by weight of polyester polyol DM2003 (Guangdong Dymatic Chemicals, Inc., China), 1.5 parts by weight of foam stabilizer DC3201 (Air Products and Chemicals, Inc., America), 1 part by weight of catalyst JXP-508 (Air Products and Chemicals, Inc., America), 0.6 part by weight of catalyst JXP-509 (Air Products and Chemicals, Inc., America) and 1.5 parts by weight of catalyst K-15 (Air Products and Chemicals, Inc., America) are mixed homogeneously to obtain a foaming composition. Then 25 parts by weight of flame retardant TCPP and 155 parts by weight of isocyanate MDI (PM200) are added to the composition, and a polyurethane foam material is obtained by stirring and foaming.

Example 8

4 parts by weight of the compound A-1 as foaming agent, 10 parts by weight of HFC-365mfc, 15 parts by weight of polyether polyol 4110 (BEFAR GROUP CO., LTD, Bin-Zhou, China), 35 parts by weight of polyester polyol DM2003 (Guangdong Dymatic Chemicals, Inc., China), 1.5 parts by weight of foam stabilizer DC3201, 0.5 part by weight of catalyst PC-8 (Air Products and Chemicals, Inc., America), 0.5 part by weight of catalyst PC-41 (Air Products and Chemicals, Inc., America) are mixed homogeneously to obtain a foaming composition; and then 25 parts by weight of flame retardant TCPP and 160 parts by weight of isocyanate MDI (PM200) are added to the composition. A polyurethane foam material is obtained by stirring and foaming.

Example 9

7 parts by weight of the compound A-3 as foaming agent, 1 part by weight of catalyst PC-41 (Air Products and Chemicals, Inc., America), 0.5 part by weight of catalyst PC-8 (Air Products and Chemicals, Inc., America), 13 parts by weight of cyclopentane, and 2 parts by weight of foam stabilizer DC8545 (Air Products and Chemicals, Inc., America) are added to a mixture of 50 parts by weight of polyether polyol 2010 (Jiangsu Haian Petrochemical Plant), 25 parts by weight of polyether polyol SA380 (Shandong INOV Polyurethane Incorporated) and 25 parts by weight of polyether polyol SA460 (Shandong INOV Polyurethane Incorporated) and mixed homogeneously to obtain a foaming composition, then 150 parts by weight of isocyanate MDI (PM200) is added to the foaming composition; and then, the resultant mixture is stirred uniformly to carry out foaming, so as to obtain a polyurethane foam material.

Example 10

5 parts by weight of the compound A-2 as foaming agent, 8 parts by weight of HFC-365mfc, 30 parts by weight of polyether polyol 4110 (BEFAR GROUP CO., LTD, Bin-Zhou, China), 20 parts by weight of polyester polyol CF6320 (Jiangsu Fusheng Innovative Material Technologies, Ltd., China), 1 part by weight of foam stabilizer DC3201 (Air Products and Chemicals, Inc., America), 12.5parts by weight of flame retardant TCPP (Jiangsu Yoke Chemical Ltd.), 1 part by weight of catalyst A33 (33LV, Air Products and Chemicals, Inc., America), and 1 part by weight of catalyst PC-41 (Air Products and Chemicals, Inc., America) are mixed homogeneously to obtain a foaming composition; and then 102 parts by weight of isocyanate MDI (PM200) are added to the composition, so as to obtain a polyurethane foam material by stirring and foaming.

TABLE 1 properties of polyurethane foams

| Example No | Foaming agent | Foam density Kg/m$^3$ | Coefficient of heat conductivity w/m · k (10° C.) | Compression strength Kpa | Shrinkage ratio % |
|---|---|---|---|---|---|
| 1 | A-1 | 35.01 | 0.02045 | 181.0 Kpa | <1.5% |
| 2 | A-2 | 34.96 | 0.02070 | 175.3 Kpa | <1% |
| 3 | A-3 | 35.18 | 0.02035 | 175.4 | <0.5% |
| 4 | A-4 | 34.86 | 0.01910 | 155.8 | <0.5% |
| 5 | A-5 | 40.35 | 0.02088 | 201.30 | <1.5% |
| 6 | A-6 | 35.45 | 0.02047 | 178.54 | <0.3% |
| 7 | A-7 + HFC-365mfc | 35.46 | 0.02125 | 173.55 | 6% |
| 8 | A-1 + HFC-365mfc | 35.12 | 0.02158 | 180.23 | 5.5% |
| 9 | A-3 + cyclopentane | 35.27 | 0.02122 | 168.54 | 5% |
| 10 | A-2 + HFC-365mfc | 35.76 | 0.02145 | 178.44 | 5.2% |

Explanation: the tested data in above tables is obtained by testing on the foam specimens prepared by using conventional foaming box and self-made foaming mold, wherein the foam specimens are free-rised foam specimens by hand making.

The shrinkage ratio (dimensional change ratio) is determined according to China National Standards GB/T 8811-2008, except that its storage time is 5 months, the same below.

The foam product of example 4 appears to be fine, uniform and dense, as showed in FIG. 4; the foam product has a favorable heat-insulating property and can satisfy various performance requirements in the field of refrigerator and refrigerating cabinet. The product of example 5 can satisfy various performance requirements in the field of polyurethane piping insulation. The foam product of example 6 appears to be fine, uniform and dense, and can satisfy various performance requirements in the application field of LNG (liquefied natural gas) transportation cold insulation. The product of example 7 can satisfy various performance requirements in the field of polyurethane insulation board. The product of example 8 can satisfy various performance requirements in the field of polyurethane color steel plate and cold storage board.

Example 11

7 parts by weight of the compound B-1 as foaming agent prepared by above example B-1, 50 parts by weight of polyether polyol 4110 (BEFAR GROUP CO., LTD, Bin-Zhou, China), 1 part by weight of foam stabilizer DC3201 (Air Products and Chemicals, Inc., America), 12.5 parts by weight of flame retardants TCPP (Jiangsu Yoke Chemical Limited Company, China), and 2 parts by weight of catalyst A33 (33LV, Air Products and Chemicals, Inc., America) are mixed homogeneously to obtain a transparent foaming composition, then 95.5 parts by weight of isocyanate MDI (PM200) is added to the composition, and a polyurethane foam material is obtained by stirring and foaming.

Examples 12-20

Examples 12-20 respectively are conducted by repeating examples 2-10 except that the foaming agents used are as listed in the table 2.

TABLE 2 properties of polyurethane foams

| Example No | Foaming agent | Foam density Kg/m³ | Coefficient of heat conductivity w/m·k (10° C.) | Compression strength Kpa | Shrinkage ratio % |
|---|---|---|---|---|---|
| 11 | B-1 | 35.02 | 0.02047 | 181.3 | <1.5% |
| 12 | B-2 | 34.92 | 0.02072 | 174.5 | <1% |
| 13 | B-3 | 35.10 | 0.02125 | 174.4 | <0.5% |
| 14 | B-4 | 34.56 | 0.01905 | 154.7 | <0.5% |
| 15 | B-5 | 41.21 | 0.02087 | 202.05 | <0.3% |
| 16 | B-6 | 35.14 | 0.02045 | 185.02 | <0.5% |
| 17 | B-3 | 35.34 | 0.02043 | 176.34 | <0.5% |
| 18 | B-3 | 35.14 | 0.02068 | 181.22 | <1% |
| 19 | B-5 + cyclopentane | 35.36 | 0.02252 | 179.04 | 4.4% |
| 20 | B-7 | 35.37 | 0.02075 | 177.54 | <1% |

Explanation: the tested data in above tables is obtained by testing on the foam specimens prepared by using conventional foaming box and self-made foaming mold, wherein the foam specimens are free-rised foam specimens by hand making.

Figure 9:
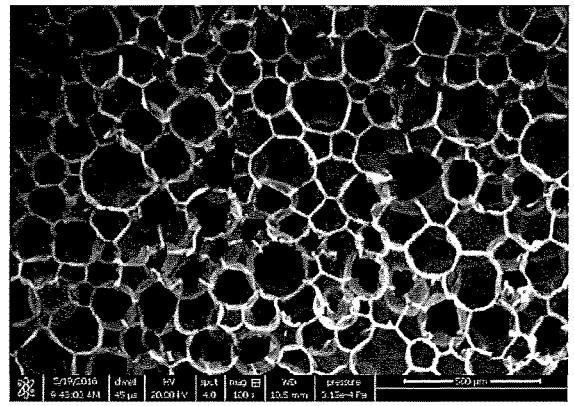
FIG. 9 is a SEM photograph of the foam of example 16.

The foam product of example 14 has a favorable heat-insulating property and can satisfy various performance requirements in the field of refrigerator and refrigerating cabinet. The product of example 15 can satisfy various performance requirements in the field of polyurethane piping insulation. The foam product of example 16 appears to be fine, uniform and dense, as showed in FIG. 9, and hence can satisfy various performance requirements in the application field of LNG (liquefied natural gas) transportation cold insulation. The product of example 17 can satisfy various performance requirements in the field of polyurethane insulation board. The product of example 18 can satisfy various performance requirements in the field of polyurethane color steel plate and cold storage board.

Example 21

4 parts by weight of the compound C-1 as foaming agent prepared by above example C-1, 50 parts by weight of polyether polyol 4110, 1 part by weight of foam stabilizer DC3201, 12.5 parts by weight of flame retardants TCPP (Jiangsu Yoke Chemical Limited Company, China), 1 part by weight of catalyst A33 (33LV, Air Products and Chemicals, Inc., America) and 1 part by weight of catalyst PC-41 (Air Products and Chemicals, Inc., America) are mixed homogeneously to obtain a transparent foaming composition, 104.5 parts by weight of isocyanate MDI (PM200) is added to the composition, and then a polyurethane foam material is obtained by stirring and foaming.

Example 22

4 parts by weight of the compound C-2 as foaming agent prepared by above example C-2, 30 parts by weight of polyether polyol 4110, 20 parts by weight of polyester polyol CF6320 (Jiangsu Fusheng New Material Limited Company, China), 12.5 parts by weight of flame retardants TCPP (JiangSu Yoke Chemical Ltd., China), 1 part by weight of foam stabilizer DC3201 (Air Products and Chemicals, Inc., America), 0.5 part by weight of catalyst PC-8 (Air Products and Chemicals, Inc., America), and 1 part by weight of catalyst PC-41 (Air Products and Chemicals, Inc., America) are mixed to obtain a transparent foaming composition, 100 parts by weight of isocyanate MDI (PM200) is added to the composition, and then a polyurethane foam material is obtained by stirring and foaming.

Example 23

3.5 parts by weight of the compound C-3 as foaming agent prepared by above example C-3, 2 parts by weight of foam stabilizer DC3201 (Air Products and Chemicals, Inc., America), 1 part by weight of catalyst PC-8 (Air Products and Chemicals, Inc., America), 1 part by weight of catalyst PC-41 (Air Products and Chemicals, Inc., America) and 13 parts by weight of cyclopentane are added to a mixture of 50 parts by weight of polyether polyol 2010 (Jiangsu Haian Petrochemical Plant), 25 parts by weight of polyether polyol SA380 (Shandong INOV Polyurethane Incorporated) and 25 parts by weight of polyether polyol SA460 (Shandong INOV Polyurethane Incorporated) and are mixed homogeneously to obtain a transparent foaming composition, 145 parts by weight of isocyanate MDI (PM200) is added to the foaming composition; and then, the resultant mixture is stirred uniformly and is injected into a foaming mould to carry out foaming, so as to obtain a polyurethane foam material with skin.

Examples 24-26

Examples 24-26 respectively are conducted by repeating examples 21-23 except that the foaming agents used are those listed in the table 2. The ratio of closed cells is >97%.

TABLE 3 properties of polyurethane foams

| Example No | Foaming agent | Foam density Kg/m$^3$ | Coefficient of heat conductivity w/m · k (10° C.) | Compression strength Kpa | Shrinkage ratio % |
|---|---|---|---|---|---|
| 21 | C-1 | 35.01 | 0.02145 | 181.0 | <2% |
| 22 | C-2 | 34.95 | 0.02160 | 175.3 | <1.5% |
| 23 | C-3 | 34.88 | 0.02035 | 185.4 | <1.5% |
| 24 | C-4 | 33.02 | 0.02045 | 182.1 | <1.2% |
| 25 | C-5 | 33.45 | 0.02060 | 180.5 | <1.0% |
| 26 | C-6 | 33.67 | 0.02032 | 185.3 | <1.0% |

Explanation: the tested data in above tables is obtained by testing on the foam specimens prepared by using conventional foaming box and self-made foaming mold, wherein the foam specimens are free-rised foam specimens by hand making.

Example 27

17 parts by weight of the compound D-1 as foaming agent prepared by above example D-1, 100 parts by weight of polyether polyol 4110 (BEFAR GROUP CO., LTD, Bin-Zhou, China), 2 parts by weight of foam stabilizer DC3201 (Air Products and Chemicals, Inc., America), 2 parts by weight of catalyst A33 (33LV) and 2 parts by weight of catalyst PC-41 (Air Products and Chemicals, Inc., America) are mixed homogeneously to obtain a transparent foaming composition, 160 parts by weight of isocyanate MDI (PM200) is added to the composition, and then a polyurethane foam material is obtained by stirring and foaming.

Example 28

25 parts by weight of the compound E-1 as foaming agent, 50 parts by weight of polyether polyol 2010 (Jiangsu Haian Petrochemical Plant), 25 parts by weight of polyether polyol SA380 (Shandong INOV Polyurethane Incorporated), 25 parts by weight of polyether polyol SA460 (Shandong INOV Polyurethane Incorporated), 2 parts by weight of foam stabilizer DC3201 (Air Products and Chemicals, Inc., America), 0.5 part by weight of catalyst PC-8 (Air Products and Chemicals, Inc., America) and 1 part by weight of catalyst PC-41 (Air Products and Chemicals, Inc., America) are mixed homogeneously to obtain a transparent foaming composition, 155 parts by weight of isocyanate MDI (PM200) is added to the foaming composition, and then the resultant mixture is stirred uniformly to carry out foaming, so as to obtain a polyurethane foam material.

Example 29

15 parts by weight of the compound F-1 as foaming agent, 10 parts by weight of cyclopentane, 2 parts by weight of foam stabilizer DC3201 (Air Products and Chemicals, Inc., America), 1 part by weight of catalyst PC-8 (Air Products and Chemicals, Inc., America), 1.5 parts by weight of catalyst PC-41 (Air Products and Chemicals, Inc., America) are added to a mixture of 50 parts by weight of polyether polyol 2010 (Jiangsu Haian Petrochemical Plant), 25 parts by weight of polyether polyol SA380 (Shandong INOV Polyurethane Incorporated) and 25 parts by weight of polyether polyol SA460 (Shandong INOV Polyurethane Incorporated) and are mixed homogeneously to obtain a transparent foaming composition, 150 parts by weight of isocyanate MDI (PM200) is added to the foaming composition; and then, the resultant mixture is stirred uniformly and injected into a foaming mould to carry out foaming, so as to obtain a polyurethane foam material having skin.

Comparative Example 1

The example 28 is repeated except that only 15 parts by weight of cyclopentane are used as foaming agent.

TABLE 4 properties of polyurethane foams

| Example No | Foaming agent | Foam density Kg/m$^3$ | Coefficient of heat conductivity w/m · k (10° C.) | Compression strength Kpa | Shrinkage ratio % |
|---|---|---|---|---|---|
| 27 | D-1 | 35.00 | 0.02200 | 161.0 | 2.5% |
| 28 | E-1 | 36.98 | 0.02188 | 155.9 | 2.3% |
| 29 | F-1 | 36.83 | 0.02036 | 165.4 | 3% |
| Comparative example 1 | Cyclopentane | 35.85 | 0.02440 | 145.4 | 7% |

Explanation: the tested data in above tables is obtained by testing on the foam specimens prepared by using conventional foaming box and self-made foaming mold, wherein the foam specimens are free-rised foam specimens by hand making.

Example 30

12 parts by weight of the compound G-1 as foaming agent prepared by above example G-1, 50 parts by weight of polyether polyol 4110, 1 part by weight of foam stabilizer DC3201, 12.5 parts by weight of flame retardants TCPP (Jiangsu Yoke Chemical Limited Company, China), 1 part by weight of catalyst A33 (33LV, Air Products and Chemicals, Inc., America) and 1 part by weight of catalyst PC-41 (Air Products and Chemicals, Inc., America) are mixed homogeneously to obtain a foaming composition, 104.5 parts by weight of isocyanate MDI (PM200) is added to the composition, and then a polyurethane foam material is obtained by stirring and foaming.

Example 31

7.5 parts by weight of the compound G-2 as foaming agent prepared by above example G-2, 30 parts by weight of polyether polyol 4110, 20 parts by weight of polyester polyol CF6320 (Jiangsu Fusheng New Material Limited Company, China), 12.5 parts by weight of flame retardants TCPP (Jiangsu Yoke Chemical Ltd., China), 1 part by weight of foam stabilizer DC3201 (Air Products and Chemicals, Inc., America), 0.5 part by weight of catalyst PC-8 (Air Products and Chemicals, Inc., America), and 1 part by weight of catalyst PC-41 (Air Products and Chemicals, Inc., America) are mixed to obtain a foaming composition, isocyanate MDI (PM200) is added to the composition, and then a polyurethane foam material is obtained by stirring and foaming.

Example 32

9 parts by weight of the compound G-3 as foaming agent prepared by above example G-3, 2 parts by weight of foam stabilizer DC3201 (Air Products and Chemicals, Inc., America), 1 part by weight of catalyst PC-8 (Air Products and Chemicals, Inc., America), 1 part by weight of catalyst PC-41 (Air Products and Chemicals, Inc., America), 13 parts by weight of cyclopentane are added to a mixture of 50 parts by weight of polyether polyol 2010 (Jiangsu Haian Petrochemical Plant), 25 parts by weight of polyether polyol SA380 (Shandong INOV Polyurethane Incorporated) and 25 parts by weight of polyether polyol SA460 (Shandong INOV Polyurethane Incorporated) and are mixed homogeneously to obtain a foaming composition, 145 parts by weight of isocyanate MDI (PM200) is added to the foaming composition; and then the resultant mixture is stirred uniformly and is injected into a foaming mould to carry out foaming, so as to obtain a polyurethane foam material having skin.

Example 33

9.5 parts by weight of the compound G-4 as foaming agent prepared by above example G-4, 2 parts by weight of foam stabilizer DC3201 (Air Products and Chemicals, Inc., America), 1 part by weight of catalyst PC-8 (Air Products and Chemicals, Inc., America), 1 part by weight of catalyst PC-41 (Air Products and Chemicals, Inc., America) and 13 parts by weight of cyclopentane are added to a mixture of 50 parts by weight of polyether polyol 2010 (Jiangsu Haian Petrochemical Plant), 25 parts by weight of polyether polyol SA380 (Shandong INOV Polyurethane Incorporated) and 25 parts by weight of polyether polyol SA460 (Shandong INOV Polyurethane Incorporated) and are mixed homogeneously to obtain a foaming composition, 145 parts by weight of isocyanate MDI (PM200) is added to the foaming composition, and then, the resultant mixture is stirred uniformly and is injected into a foaming mould to carry out foaming, so as to obtain a polyurethane foam material having skin.

TABLE 5 properties of polyurethane foams

| Example No | Foaming agent | Foam density Kg/m³ | Coefficient of heat conductivity w/m·k (10° C.) | Compression strength Kpa | Shrinkage ratio % |
|---|---|---|---|---|---|
| 30 | G-1 | 35.03 | 0.02131 | 185.0 | <1.5% |
| 31 | G-2 | 34.83 | 0.02130 | 174.4 | <1.2% |
| 32 | G-3 | 34.67 | 0.02135 | 184.5 | <1.2% |
| 33 | G-4 | 33.56 | 0.02122 | 183.3 | <1% |

Explanation: the tested data in above tables is obtained by testing on the foam specimens prepared by using conventional foaming box and self-made foaming mold, wherein the foam specimens are free-rised foam specimens by hand making.

The properties of the chemical foaming agent (CFA) of the present invention
1. The Testing of Storage Stability and Foaming Characteristics of the Foaming Composition ("White Material")
①. The Stability Testing of the White Material Prepared by Combination of CFA-CP (Cyclopentane)

A white material (i.e., the white material of above example 9) containing CFA-CP mixed system is formulated according to the required parameters of the white material used for refrigerators, the reactivity of the white material is determined after the white material being stored in an oven uncder 50° C., and then the reactivity of the white material is determined by sampling from the white material at interval of a few days. The resulting experimental results are listed in the following table 5:

TABLE 5 the reactivity of the white material

| Date | Reaction time (s) |
|---|---|
| 2015 Aug. 28 | CT: 9 GT: 55 |
| 2015 Aug. 29 | CT: 9 GT: 55 |
| 2015 Aug. 31 | CT: 8 GT: 54 |
| 2015 Sep. 3 | CT: 9 GT: 55 |
| 2015 Sep. 6 | CT: 8 GT: 56 |
| 2015 Sep. 12 | CT: 9 GT: 54 |
| 2015 Sep. 14 | CT: 9 GT: 53 |
| 2015 Sep. 16 | CT: 8 GT: 56 |
| 2015 Sep. 18 | CT: 9 GT: 55 |
| 2015 Sep. 21 | CT: 8 GT: 54 |
| 2015 Sep. 24 | CT: 9 GT: 56 |
| 2015 Sep. 28 | CT: 9 GT: 54 |
| 2015 Oct. 5 | CT: 9 GT: 56 |
| 2015 Oct. 9 | CT: 10 GT: 54 |
| 2015 Oct. 15 | CT: 9 GT: 55 |
| 2015 Oct. 19 | CT: 9 GT: 56 |

In the above table, CT represents cream time (rise time); GT represents gel time.

It is indicated from above table that the reactivity of the white material containing the CFA-CP combination nearly does not change with the time for storing the white material, and it is generally believed that if the white material can be stored under 50° C. for 51 days, it can be stored at normal temperature for more than half a year.

Besides the reactivity, the coefficients of heat conductivity of the resulting foam materials prepared by mixing of the CFA-CP system in various samples are nearly the same (over time); the following several foam materials are prepared (under the same conditons to those in example 9) by sampling from the white material at different time interval and their characteristics such as coefficient of heat conductivity are tested, the results are as follows:

| Date | Density kg/m³ | Coefficient of heat conductivity (10° C.) λ w/m·k |
|---|---|---|
| 2015 Aug. 28 | 35 | 0.01917 |
| 2015 Sep. 12 | 35 | 0.01923 |
| 2015 Sep. 24 | 35 | 0.01906 |
| 2015 Oct. 15 | 35 | 0.01911 |

It is indicated from above table that the densities of foams prepared from different samples which are sampled from the same white material at different storage time are nearly the same and hence these results can illustrate that the foaming efficiencies of these different samples are the same (i.e., keep steady) and the coefficients of heat conductivity of resulting foam materials are also nearly the same.

②. The Stability Experiments of the White Material Prepared by Only Using CFA as Foaming Agent The example 5 is repeated except that, the white material prepared by only using CFA as foaming agent according to a conventional formulation of white material is stored at room temperature for 3 months, the reactivity of white material samples sampled from the storing white material at interval of one month and the coefficients of heat conductivity of resulting foam materials are tested, and the results are listed as follows:

| Date | Reaction time | Coefficient of heat conductivity (10° C.) λ w/m · k |
| --- | --- | --- |
| 2013 Nov. 27 | CT: 9 GT: 25 TFT: 32 | 0.02085 |
| 2014 Jan. 24 | CT: 9 GT: 24 TFT: 32 | 0.02123 |
| 2014 Feb. 26 | CT: 9 GT: 24 TFT: 35 | 0.02093 |
| 2014 Mar. 27 | CT: 9 GT: 25 TFT: 36 | 0.02140 |

The TFT in above table indicates the tack-free time of foaming composition.

It is observed from above table that both the reactivity of white material containing the CFA of present invention and the coefficient of heat conductivity of the resulting foam do not change with the time for storing the white material.

③ the Dimension Stability Comparison Between the Foam Prepared by CFA Free Foaming and the Foam Perpared by Using Water Foaming Under the Condition of Low Foam Density The above example 5 is repeated except that the amount of foaming agent is change into 15 parts by weight of compound A-4, and at the same time, as a comparison, the above example 5 is repeated except that only water is used as foaming agent, so as to prepare the white materials and the foam materials respectively. With the same density of the foam obtained, it is observed whether the stability of the two foams change with time. FIGS. 10 and 12 are respectively the initial appearance of the foams of the present invention, and FIGS. 11 and 13 are respectively the initial appearance of the comparative foams prepared by using water as foaming agent, wherein the preparation date of these foams is 16 Apr. 2015 and the densities of all the foams are 22 kg/m³. The foam samples were placed in laboratory until 29 Sep. 2015, over five months in total, and the appearance of these foam samples is observed. FIG. 14 is the photograph of the foam product samples of the present invention, and we can find out that there is hardly any change in appearance and dimension, whereas FIG. 15 is the photograph of the comparative foam samples and clearly shows shrinkage. In general, the specialists in the field of polyurethane believe that, the shrinkage of the foam prepared by using water as foaming agent is inevitable when the foam density is 25 kg/m³ more or less, and this also is the greatest difference between the using of CFA and the using of water. In other words, if the water foaming process is used in the fields such as the spray coating of building's external wall, then the resultant foam material will shrink with time, and the coefficient of heat conductivity will be deteriorated.

Other Applications

1. Use of the Foaming Agent of the Present Invention in the Preparation of Polystyrene Expanded Material Example 34

100 parts by weight of polystyrene resin powder, 6 parts by weight of the foaming agent B-1 of the present invention, calcium carbonate having an average particle size of 175 micrometres, 0.3 part by weight of zinc stearate, 0.3 part by weight of toner (Weichang brand, produced and sold by Shenzhen Weichang pigment limited company in Shenzhen, China) are charged into a mixer to carry out mixing under a temperature in a range of 30-40° C., to obtain a polystyrene expanding composition, and the composition is extruded by a single screw extruder (the length-diameter ratio of its screw is 28:1) and molded. The temperatures of various sections of the extruder are: 85° C.-95° C. in the first section, 95° C.-105° C. in the second section, 105° C.-115° C. in the third section, 115° C.-125° C. in the fourth section. The mould temperature is in the range of 125° C.-130° C. The rotation speed of the screw is in the range of 5 rpm-9 rpm. The apparent density of the molded material is 587 kg/m³. The SEM photograph of its sample is showed in FIG. 16 (magnification of 100 times). It is observed from the photograph that the diameters of cells are relatively uniform.

2. Use of the Foaming Agent of the Present Invention in the Preparation of Polyvinyl Choride Expanded Material Example 35

85 parts by weight of polyvinyl chloride resin, 5 parts by weight of the foaming agent A-1 of the present invention, 0.5 part by weight of polyethylene wax, calcium carbonate having an average particle size of 175 micrometres, 0.3 part by weight of zinc stearate, 0.3 part by weight of toner (Weichang brand, produced and sold by Shenzhen Weichang Pigment Limited Company in Shenzhen, China) are charged into a mixer to carry out mixing under a temperature in a range of 30-40° C., to obtain a polyvinyl choride expanding composition, and the composition is extruded by a single screw extruder (the length-diameter ratio of its screw is 28:1) and molded. The temperatures of various sections of the extruder are: 145° C.-150° C. in the first section, 155° C.-165° C. in the second section, 175° C.-185° C. in the third section, 180° C.-195° C. in the fourth section. The mould temperature is in the range of 195° C.-205° C. The rotation speed of the screw is in the range of 5 rpm-9 rpm. The specific gravity of the molded material is 0.55 g/cm³.

3. The Preparation of Hydrazino Alkanolamine Salt Compounds and their Use as Foaming Agent Example 36 (Preparation Example)

Figure 17:
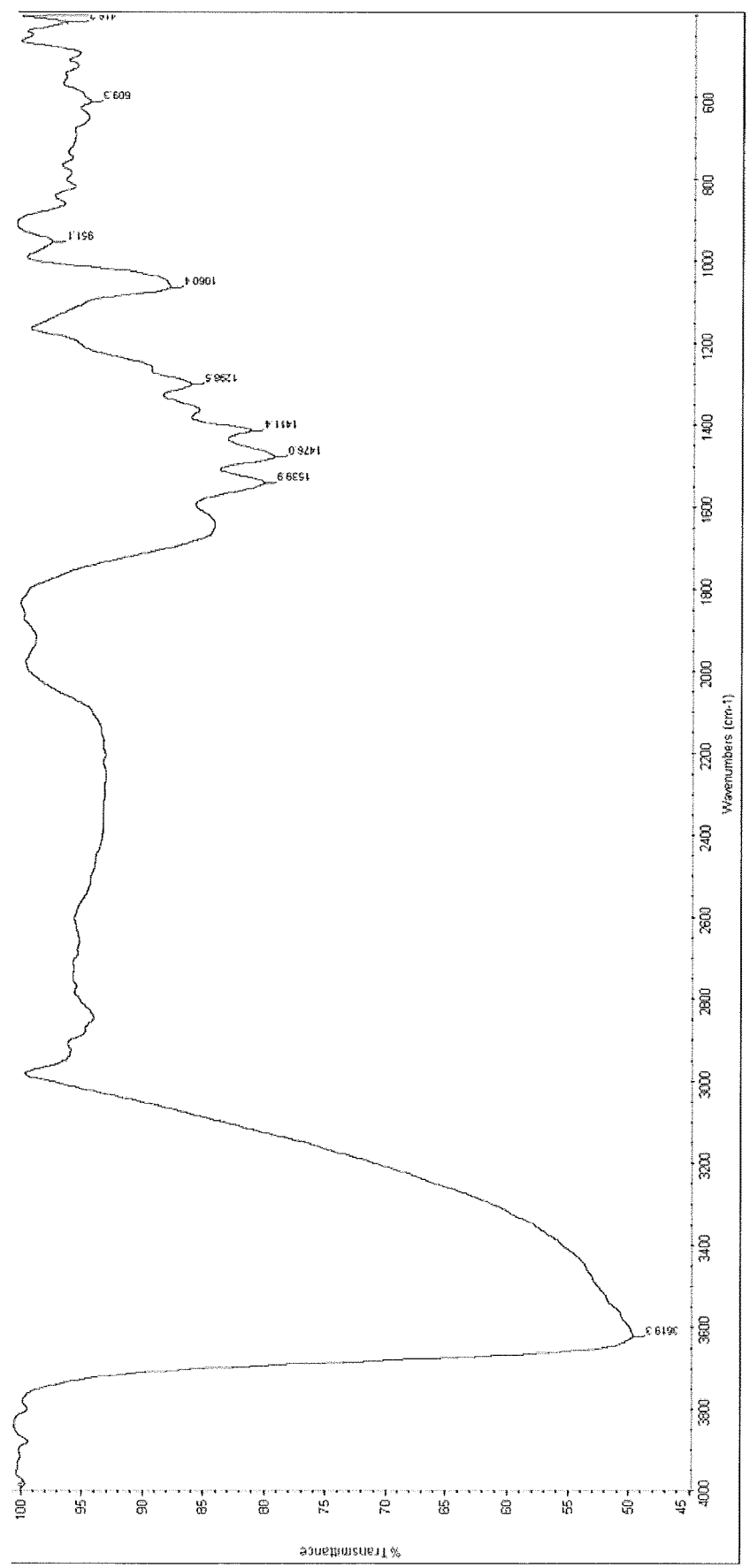
FIG. 17 is an infrared spectrogram of compound (i.e., hydrazino alkanolamine salt) of example 36.

730 g of 80% hydrazine hydrate and 450 g of water are charged into a stainless steel autoclave equiped with cooling jacket, agitation is started to intensively mix the hydrazine hydrate and water. The reaction system is treated and protected by nitrogen gas and then is heated up, and the temperature is controlled to a range of 45-70° C. and the pressure is controlled to not more than 0.3 MPa. 1200 g (in total) of propylene oxide (molecular weight 58.08) is incorporated slowly and batchwise into the reaction system, and after the incorporation is completed, the reaction system is stirred and reacted for 1 hour under the temperature of 45-70° C. and the pressure below 0.3 MPa. The temperature of the reaction system is then reduced to 50° C., and the unnecessary water and the unreacted propylene oxide are removed from the reaction system under reduced pressure of 600 mmHg. Agitation is started. 800-1200 g of carbon dioxide is passed into the autoclave, and the reaction system is reacted at the temperature of 45-60° C. and under the pressure of not more than 0.3 MPa for 4-8 hours. After cooling to below 40° C., the resulting product is discharged, so obtain compounds, i.e., hydrazino alkanolamine salt compound, pH=8.9. The decomposition temperature of the compound (s) is in a range of 45-70° C. The compound(s) quickly release carbon dioxide gas by heating to 55° C. The infrared spectrogram of the compound(s) is showed in FIG. 17.

Example 37 (Application Example)

20 parts by weight of the compounds as foaming agent prepared by above example 36, 30 parts by weight of polyether polyol 4110, 20 parts by weight of polyester polyol CF6320 (Jiangsu Fusheng Innovative Material Technologies, Ltd., China), 12.5 parts by weight of flame retardants TCPP (Jiangsu Yoke Chemical Ltd.), 1 part by weight of foam stabilizer DC3201 (Air Products and Chemicals, Inc., America), 0.5 part by weight of catalyst PC-8 (Air Products and Chemicals, Inc., America), 1 part by weight of catalyst PC-41 (Air Products and Chemicals, Inc., America) are mixed to obtain a transparent foaming composition, isocyanate MDI (PM200) is added to the composition, and then a polyurethane foam material is obtained by stirring and foaming.

Example 38 (Preparation Example)

730 g of 80% hydrazine hydrate and 450 g of water are charged into a stainless steel autoclave equiped with cooling jacket, agitation is started to intensively mix the hydrazine hydrate and water. The resultant reaction system is treated and protected by nitrogen gas and then is heated up, and the temperature is controlled to a range of 45-70° C. and the pressure is controlled to not more than 0.3 MPa. 910 g (in total) of ethylene oxide (molecular weight 58.08) is incorporated slowly and batchwise into the reaction system, and after the incorporation is ended, the reaction system is stirred for 1 hour under the temperature of 45-70° C. and the pressure below 0.3 MPa. The temperature of the reaction system is reduced to 50° C., and the unnecessary water and the unreacted ethylene oxide are removed from the reaction system under reduced pressure of 600 mmHg. Agitation is started. 800-1200 g of carbon dioxide is passed into the autoclave, and the reaction system is reacted at the temperature of 45-60° C. and under the pressure of not more than 0.3 MPa for 4 hours. After cooling to below 40° C., the resulting product is discharged, so obtain compounds, pH=8.8. The decomposition temperature of the compound (s) is in a range of 45-70° C. The compound(s)quickly release carbon dioxide gas by heating to 56° C.

Example 39 (Application Example)

17 parts by weight of the compounds as foaming agent prepared by above example 38, 30 parts by weight of polyether polyol 4110, 20 parts by weight of polyester polyol CF6320 (Jiangsu Fusheng Innovative Material Technologies, Ltd., China), 12.5 parts by weight of flame retardants TCPP (Jiangsu Yoke Chemical Ltd., China), 1 part by weight of foam stabilizer DC3201 (Air Products and Chemicals, Inc., America), 0.5 part by weight of catalyst PC-8 (Air Products and Chemicals, Inc., America), 1 part by weight of catalyst PC-41 (Air Products and Chemicals, Inc., America) are mixed to obtain a transparent foaming composition, isocyanate MDI (PM200) is added to the composition, and then a polyurethane foam material is obtained by stirring and foaming.

4. Use of Polyalkylene Polyamine Carbonate as the Foaming Agent in the Preparation of Polystyrene Expanded Material Example 40

100 parts by weight of polystyrene resin powder, 6 parts by weight of diethylene triamine carbonate, calcium carbonate having an average particle size of 175 micrometres, 0.3 part by weight of zinc stearate, 0.3 part by weight of toner (Weichang brand, produced and sold by Shenzhen Weichang Pigment Limited Company in Shenzhen, China) are charged into a mixer to carry out mixing under a temperature in a range of 30-40° C., to obtain a polystyrene expanding composition, and the composition is extruded by a single screw extruder (the length-diameter ratio of its screw is 28:1) and molded; wherein the temperatures of various sections of the extruder are: 85° C.-95° C. in the first section, 95° C.-105° C. in the second section, 105° C.-115° C. in the third section, 115° C.-125° C. in the fourth section. The mould temperature is in the range of 125° C.-130° C. The rotation speed of the screw is in the range of 5 rpm-9 rpm. The apparent density of the molded material is 536 kg/m$^3$. The product is similar to that of example 34, and it is observed from its SEM photograph (magnification of 100 times) that diameters of cell are relatively uniform.

5. Use of Polyalkylene Polyamine Carbonate as the Foaming Agent in the Preparation of Polyvinyl Choride Expanded Material Example 41

85 parts by weight of polyvinyl chloride resin, 5 parts by weight of dipropylene triamine carbonate, 0.5 part by weight of polyethylene wax, calcium carbonate having an average particle size of 175 micrometres, 0.3 part by weight of zinc stearate, 0.3 part by weight of toner (Weichang brand, produced and sold by Shenzhen Weichang pigment limited company in Shenzhen, China) are charged into a mixer to carry out mixing under a temperature in a range of 30-40° C., to obtain a polyvinyl choride expanding composition, and the composition is extruded by a single screw extruder (the length-diameter ratio of its screw is 28:1) and molded; wherein the temperatures of various sections of the extruder are: 145° C.-150° C. in the first section, 155° C.-165° C. in the second section, 175° C.-185° C. in the third section, 180° C.-195° C. in the fourth section. The mould temperature is in the range of 195° C.-205° C. The rotation speed of the screw is in the range of 5 rpm-9 rpm. The specific gravity of the molded material is 0.53 g/cm$^3$.

The invention claimed is:
1. A foaming agent which comprises alkanolamine salt compounds of the following general formula (I) or a mixture of alkanolamine salt compounds of the following general formula (I):

$$A^{n-}[B^{m+}]p \qquad (I)$$

wherein $A^{n-}$ is carbonate $CO_3^{2-}$, and n=2;
$B^{m+}$ is an organic amine (B) cation having m of $-^+NR^3R^4H$ groups and/or $-^+NR^3H-$groups;

wherein m=1, 2, 3, 4, or 5; p=2/m; and wherein, $R^3$ and $R^4$ are independently chosen from the group consisting of: H and R;

provided that: the alkanolamine salt compounds of the general formula (I) have at least one R group linked to its N atom(s);

wherein the R group is $HOCH_2CH_2—$, $HOCH_2CH(CH_3)—$, or $HOCH(CH_3)CH_2—$;

wherein a water content in the foaming agent is 5-30 wt % based on a total weight of the foaming agent, a total content of the compounds of the general formula (I) and water in the foaming agent is 99-100 wt %, based on the total weight of the foaming agent, and a pH of the foaming agent is 8-10;

wherein the foaming agent is prepared by a reaction of a first material with a second material in the presence of water, wherein the first material is one or more compounds selected from the group consisting of the following compounds:

ammonium carbamate, $(NH_4)_2CO_3$, and organic amine compound (M) salt of carbonic acid;

the second material is one or more selected from ethylene oxide, and propylene oxide;

wherein the organic amine compound (M) is an organic amine compound selected from the group consisting of following compounds:

methylamine, ethylamine, propylamine, or butylamine;

dimethylamine, diethylamine, methyl ethyl amine, dipropyl amine, or methyl propyl amine;

ethylene diamine, N-methyl-ethylene diamine, N,N'-dimethyl ethylene diamine, 1,3-propylene diamine; butanediamine, pentanediamine, or hexanediamine;

diethylene triamine, triethylenetetraamine, or tetraethylenepentamine;

1,3,5-triamino cyclohexane; and monoethanolamine, monopropanol amine, monoisopropanolamine, or monobutanolamine.

2. The foaming agent according to claim 1, wherein: the water content in the foaming agent is from 10 wt % to 30 wt %, based on the total weight of the foaming agent; and/or the pH of the foaming agent is 9-10.

3. The foaming agent according to claim 1, wherein: the water content in the foaming agent is 15 -30 wt %, based on the total weight of the foaming agent; and/or the pH of the foaming agent is 9-9.5.

4. The foaming agent according to claim 1, wherein: the water content in the foaming agent is 15-25 wt %, based on the total weight of the foaming agent.

5. The foaming agent according to claim 1, wherein the mole ratio of the first material to the second material is 1:1.6-1:5.

6. The foaming agent according to claim 5, wherein the mole ratio of the first material to the second material is 1:3-1:4.

7. The foaming agent according to claim 1, wherein the mass content of alkali metals and alkaline earth metals in the foaming agent is 0-200 ppm; and/or the alkanolamine salt compounds of the general formula (I) contain, on average, 2-5 of R groups per molecule.

8. A method for preparing the foaming agent as claimed in claim 1, said method comprises:

reacting a first material with a second material in water, wherein the first material is one or more compounds selected from the group consisting of the following compounds:

ammonium carbamate, $(NH_4)_2CO_3$, and organic amine compound (M) salt of carbonic acid;

the second material is one or more selected from ethylene oxide and propylene oxide;

wherein the organic amine compound (M) is an organic amine compound selected from the group consisting of following compounds:

methylamine, ethylamine, propylamine, or butylamine;

dimethylamine, diethylamine, methyl ethyl amine, dipropyl amine, or methyl propyl amine;

ethylene diamine, N-methyl-ethylene diamine, N,N'-dimethyl ethylene diamine, 1,3-propylene diamine; butanediamine, pentanediamine, or hexanediamine;

diethylene triamine, triethylenetetraamine, or tetraethylenepentamine;

1,3,5-triamino cyclohexane; and monoethanolamine, monopropanol amine, monoisopropanolamine, or monobutanolamine.

9. The method according to claim 8, wherein the mole ratio of the first material to the second material is 1:1.6-1:5.

* * * * *